US011164659B2

(12) United States Patent
Fan et al.

(10) Patent No.: US 11,164,659 B2
(45) Date of Patent: Nov. 2, 2021

(54) METHODS FOR EXPRESSION PROFILE CLASSIFICATION

(71) Applicant: Becton, Dickinson and Company, Franklin Lakes, NJ (US)

(72) Inventors: Jue Fan, Menlo Park, CA (US); Jesse Zhang, Menlo Park, CA (US); Jing Hu, Menlo Park, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 637 days.

(21) Appl. No.: 15/806,223

(22) Filed: Nov. 7, 2017

(65) Prior Publication Data

US 2018/0137242 A1 May 17, 2018

Related U.S. Application Data

(60) Provisional application No. 62/446,227, filed on Jan. 13, 2017, provisional application No. 62/419,291, filed on Nov. 8, 2016.

(51) Int. Cl.
*G16B 40/30* (2019.01)
*G06F 16/28* (2019.01)
(Continued)

(52) U.S. Cl.
CPC ......... *G16B 40/30* (2019.02); *G06F 16/2246* (2019.01); *G06F 16/283* (2019.01);
(Continued)

(58) Field of Classification Search
CPC ............................. G06F 16/2246; G16B 40/00
See application file for complete search history.

(56) References Cited

U.S. PATENT DOCUMENTS 4,510,244 A 4/1985 Parks et al.
4,725,536 A 2/1988 Fritsch et al.
(Continued)

FOREIGN PATENT DOCUMENTS

DE 102008025656 12/2009
EP 0 799 897 10/1997
(Continued)

OTHER PUBLICATIONS

D'haeseleer, Dec. 2005, How does gene expression clustering work?, Nature Biotechnology, pp. 1499-1501.
(Continued)

*Primary Examiner* — Mark D Featherstone
*Assistant Examiner* — Tony Wu
(74) *Attorney, Agent, or Firm* — Knobbe, Martens, Olson & Bear, LLP

(57) ABSTRACT

Disclosed herein are methods and systems for identifying targets for distinguishing cell types. In some embodiments, the method comprises: hierarchically clustering expression profiles of cells to generate a dendrogram with each leaf representing the expression profile of a different individual cell. The dendrogram can be pruned by eliminating invalid splits (and their children). The remaining leaves in the dendrogram can be merged, independent of their locations in the dendrogram, based on their distances to one another to generate clusters of expression profiles. The method can identify targets for distinguishing cell types based on targets that are expressed differentially in the clusters.

30 Claims, 60 Drawing Sheets

(51) Int. Cl.
*G06F 16/22* (2019.01)
*G16B 40/00* (2019.01)
*G16B 25/00* (2019.01)
*G16B 99/00* (2019.01)
*G16B 25/10* (2019.01)

(52) U.S. Cl.
CPC ............ *G16B 25/00* (2019.02); *G16B 25/10* (2019.02); *G16B 40/00* (2019.02); *G16B 99/00* (2019.02)

(56) References Cited

U.S. PATENT DOCUMENTS

| | | | |
|---|---|---|---|
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 | 2/2017 | Fan et al. |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,708,657 B2 | 7/2017 | Asbury et al. |
| 9,708,659 B2 | 7/2017 | Fodor et al. |
| 9,787,810 B1 | 8/2017 | Fodor et al. |
| 9,951,386 B2 | 4/2018 | Hindson et al. |
| 2002/0072058 A1 | 6/2002 | Voelker et al. |
| 2002/0168665 A1 | 11/2002 | Okawa |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0170373 A1 | 8/2005 | Monforte |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0078941 A1* | 4/2006 | Santin ............... C12Q 1/6886 435/6.18 |
| 2006/0141493 A1* | 6/2006 | West ............... G16B 20/00 435/6.11 |
| 2006/0211030 A1 | 9/2006 | Brenner |
| 2006/0211036 A1* | 9/2006 | Chou ............... C12Q 1/6886 435/6.16 |
| 2006/0263709 A1 | 11/2006 | Matsumura et al. |
| 2006/0263789 A1 | 11/2006 | Kincaid |

(56) References Cited

U.S. PATENT DOCUMENTS

| | | |
|---|---|---|
| 2007/0020640 A1 | 1/2007 | Mccloskey et al. |
| 2007/0065823 A1 | 3/2007 | Dressman et al. |
| 2007/0117134 A1 | 5/2007 | Kou |
| 2007/0172873 A1 | 7/2007 | Brenner et al. |
| 2007/0178478 A1 | 8/2007 | Dhallan et al. |
| 2008/0010304 A1* | 1/2008 | Vempala ............... G06K 9/6224 |
| 2008/0070303 A1 | 3/2008 | West et al. |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0170075 A1* | 7/2009 | Petrovics ............... C12Q 1/6886 |
| | | 435/6.14 |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0145893 A1* | 6/2010 | Semizarov ............. C12Q 1/6886 |
| | | 706/12 |
| 2010/0255471 A1 | 10/2010 | Clarke |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0156675 A1 | 6/2012 | Lueerssen et al. |
| 2012/0163681 A1 | 6/2012 | Lohse |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0143186 A1* | 5/2014 | Bala ..................... G06N 5/025 |
| | | 706/12 |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0344013 A1* | 11/2014 | Karty ................. G06Q 30/0201 |
| | | 705/7.29 |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0066385 A1 | 3/2015 | Schnall-levin et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0298091 A1 | 10/2015 | Weitz |
| 2015/0299784 A1* | 10/2015 | Fan ..................... C12Q 1/6876 |
| | | 506/4 |
| 2015/0307874 A1 | 10/2015 | Jaitin |
| 2015/0376609 A1 | 12/2015 | Hindson et al. |
| 2016/0026758 A1 | 1/2016 | Jabara et al. |
| 2016/0046986 A1 | 2/2016 | Eltoukhy et al. |
| 2016/0244828 A1 | 8/2016 | Mason |
| 2016/0257993 A1 | 9/2016 | Fu et al. |
| 2016/0289669 A1 | 10/2016 | Fan et al. |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 12/2016 | Fodor et al. |
| 2016/0376648 A1 | 12/2016 | Fodor et al. |
| 2017/0073730 A1 | 3/2017 | Betts et al. |
| 2017/0154421 A1 | 6/2017 | Fu et al. |
| 2017/0204406 A1 | 7/2017 | Kato et al. |
| 2017/0247689 A1 | 8/2017 | Brown |
| 2017/0344866 A1 | 11/2017 | Fan et al. |
| 2018/0137242 A1 | 5/2018 | Fan et al. |
| 2018/0276332 A1 | 9/2018 | Fan et al. |
| 2019/0095578 A1 | 3/2019 | Shum |
| 2019/0218276 A1* | 7/2019 | Regev ................. C07K 16/1036 |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 07/087310 | 8/2007 |
| WO | WO 07/087312 | 8/2007 |
| WO | WO 08/096318 | 8/2008 |

(56) References Cited

FOREIGN PATENT DOCUMENTS

| WO | WO 09/148560 | 12/2009 |
|---|---|---|
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/177570 | 11/2015 |
| WO | WO 15/200869 | 12/2015 |
| WO | WO 16/118915 | 7/2016 |
| WO | WO 16/149418 | 9/2016 |
| WO | WO 16/162309 | 10/2016 |
| WO | WO 17/205691 | 11/2017 |

OTHER PUBLICATIONS

Sorlie et al., Sep. 11, 2001, Gene expression patterns of breast carcinomas distinguish tumor subclasses with clinical implications, Proceedings National Academy of Sciences PNAS, 98(19):10869-10874.
International Search Report and Written Opinion dated Feb. 22, 2018 in PCT/US2017/060451.
International Search Report and Written Opinion dated Jan. 18, 2018 in PCT/US2017/060447.
Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pp.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bogdanova et al., Jan. 2008, Normalization of full-length enriched cDNA, Molecular Biosystems, 4(3):205-212.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 17:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing, 19(3):1-12.
Butkus, Feb. 6, 2014, Cellular research set to launch first gene expression platform using 'molecular indexing' technology, genomeweb.com, 5 pp.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.

(56) References Cited

OTHER PUBLICATIONS

Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43), 15275-15278.
Fan et al., Feb. 6, 2015, Combinatorial labeling of single cells for gene expression cytometry. Science, 347(6222):1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-271.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.

Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al., 2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.

(56) References Cited

OTHER PUBLICATIONS

Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantities difference between two complex genomes. Nature Biotech, 20(9):936-939.
Marcus et a., 2006, Microfluidic single-cell mRNA isolation and analysis, Ana. Chem. 78:3084-3089.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.
Nadai et al., 2008, Protocol for nearly full-length sequencing of HIV-1 RNA from plasma, PLoS ONE, 3(1):e1420.

Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Patanjali et al., Mar. 1991, Construction of a uniform-abundance (normalized) CNDA library, Proceedings of the National Academy of Sciences, 88(5):1943-1947.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.

(56) References Cited

OTHER PUBLICATIONS

Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.
Smith et al., 2010, Highly-multiplexed barcode sequencing: an efficient method for parallel analysis of pooled samples. Nucleic Acids Research, 38(13):e142.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Stratagene 1998 Catalog, Gene Characterization Kits, p. 39.
Takahashi et al., Mar. 2006, Novel technique of quantitative nested real-time PCR assay for *Mycobacterium tuberculosis* DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.

Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office Action dated Oct. 11, 2016 in U.S. Appl. No. 15/224,460.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.

(56) References Cited

OTHER PUBLICATIONS

Office Action dated Jun. 7, 2017 in U.S. Appl. No. 14/381,488.
International Search Report and Written Opinion dated Sep. 6, 2013 in PCT/US13/028103.
Office Action dated Feb. 17, 2017 in Canadian patent application No. 2,865,575.
Office Action dated Jun. 6, 2016 in Chinese patent application No. 201380022187.9.
Office Action dated Dec. 27, 2016 in Chinese patent application No. 201380022187.9.
Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Search Report and Written Opinion dated Mar. 1, 2016 in Singapore patent application No. 11201405274W.
Written Opinion dated May 26, 2017 in Singapore patent application No. 11201405274W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US/14/053301.
Examination Report dated Apr. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
Office Action dated May 13, 2016 in U.S. Appl. No. 14/508,911.
Office Action dated Mar. 24, 2017 in U.S. Appl. No. 15/409,355.
International search report and written opinion dated Dec. 19, 2014 for PCT Application No. US2014/059542.
International Search Report and Written Opinion dated Jun. 20, 2016 in PCT/US16/14612.
Office Action dated Jan. 19, 2017 in U.S. Appl. No. 15/055,445.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
International Search Report and Written Opinion dated Sep. 28, 2016 in PCT/US16/028694.
International Search Report and Written Opinion dated Sep. 27, 2016 in PCT/US16/034473.
International Search Report and Written Opinion dated Jan. 31, 2017 in PCT/US16/050694.
International Search Report and Written Opinion dated Aug. 7, 2017 in PCT/US2017/034576.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
Di Carlo et al., Dec. 1, 2008, Dynamic single-cell analysis for quantitative biology, Analytical Chemistry, 78(23):7918-7925.
Lau et al., Sep. 21, 2017, Single molecule counting and assessment of random mulecular tagging errors with transposable giga-scale error-correcting barcodes, BMC Genomics, 18(1):1-13.
Smith et al., Jan. 18, 2017, UMI-tools: modeling sequencing errors in unique molecular identifiers to improve quantification accuracy, Genome Research, 27(3):491-499.
Third Party Observation dated Jun. 14, 2018 in Japanese patent application No. 2016-537867 (with English Translation).
Official Action dated Jul. 30, 2018 in Japanese patent application No. 2016-537867 (with English Translation).
Office Action dated May 8, 2020 in U.S. Appl. No. 15/806,174.
Examination Report dated Apr. 2, 2020 in European patent application No. 17805040.7.
Office Action dated Apr. 15, 2020 in U.S. Appl. No. 15/806,223.
International Search Report and Written Opinion dated Jul. 18, 2018 in PCT/US2018/023387.
International Search Report and Written Opinion dated Feb. 28, 2019 in PCT/US2018/052365.
Peng et al. Aug. 7, 2015 Supplementary Material BMC Bioinformatics 16:589.
Shiroguchi et al. (2012) Supplemental Material PNAS 109 4.
Tung et al., Jan. 3, 2017, Batch effects and the effective design of single-cell gene expression studies. Nature Scientific Reports, 7:39921, 15 pp.
Zorita et al., Jan. 31, 2015 Starcode: sequence clustering based on all pairs search. Bioinformatics, 13(12):1913-1919.
Office Action dated Jul. 20, 2020 in U.S. Appl. No. 15/605,874.
Office Action dated Jan. 6, 2021 in U.S. Appl. No. 15/605,874.
Examination report dated Dec. 22, 2020 in European patent application No. 17728398.3.
Written Opinion dated Oct. 7, 2020 in Singapore patent application No. 11201903158R.
Written Opinion dated Oct. 8, 2020 in Singapore patent application No. 11201903139S.
Examination Report dated Nov. 5, 2020 in European patent application No. 18716453.8.

\* cited by examiner

Pre-clustering

After splitting step

After merging step

After merging step using community detection

FIG. 9S
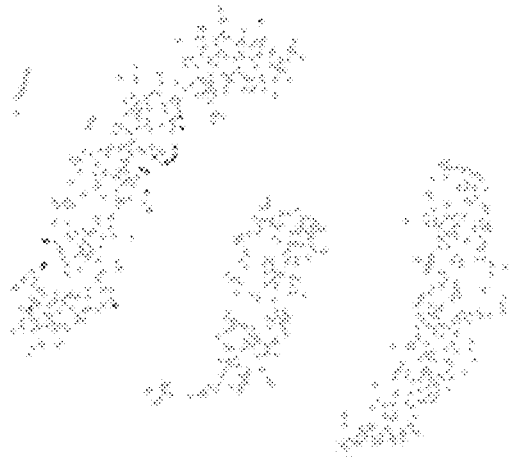 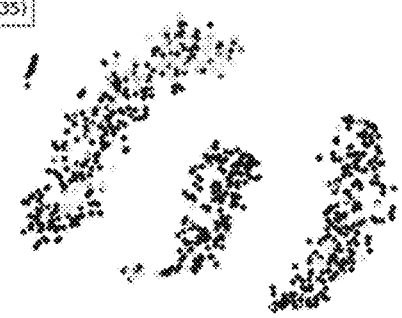
FIG. 9T
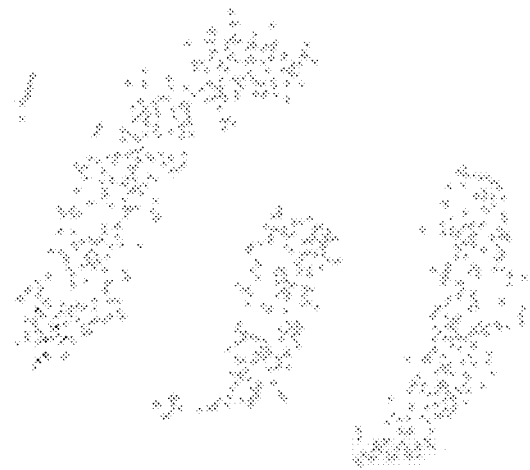 
FIG. 9U
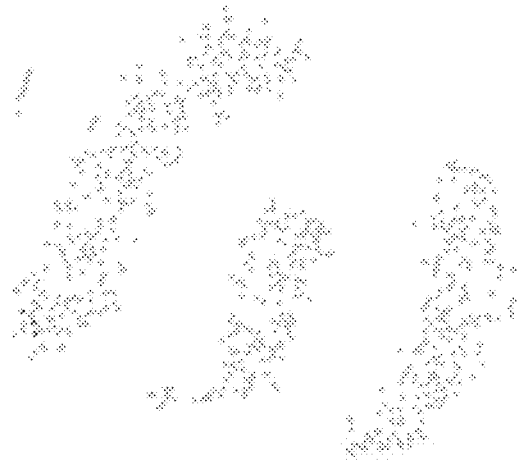 

RRP7A (0): 15.35

NDUFAF2 (0): 11.80

MRPL12 (0): 11.66

TRAPPC3 (0): 11.16

WRB (0): 10.70

TMA16 (0): 10.47

ORMDL2 (0): 10.09

DCTD (0): 10.06

ACTR6 (0): 9.95

EXOSC5 (0): 9.88

XPNPEP1 (0): 9.88

OPHS (0): 9.71

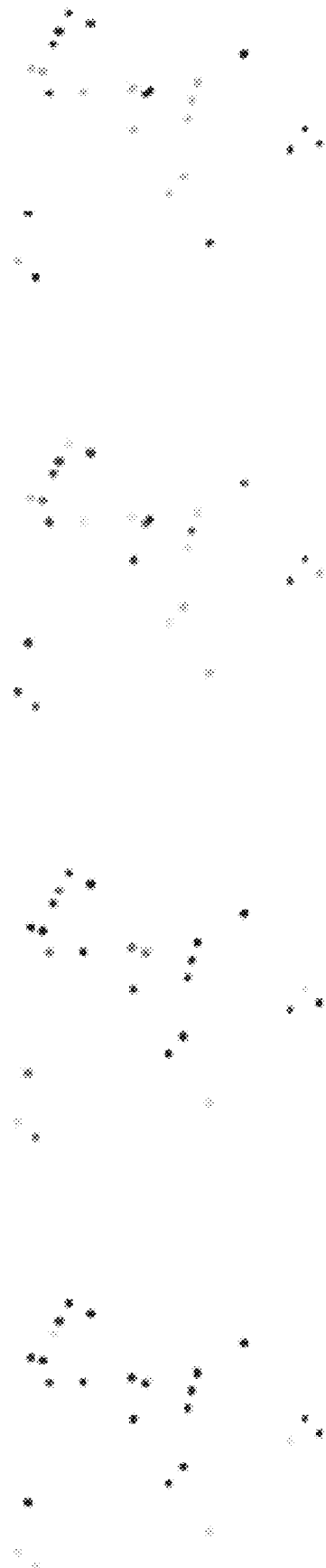

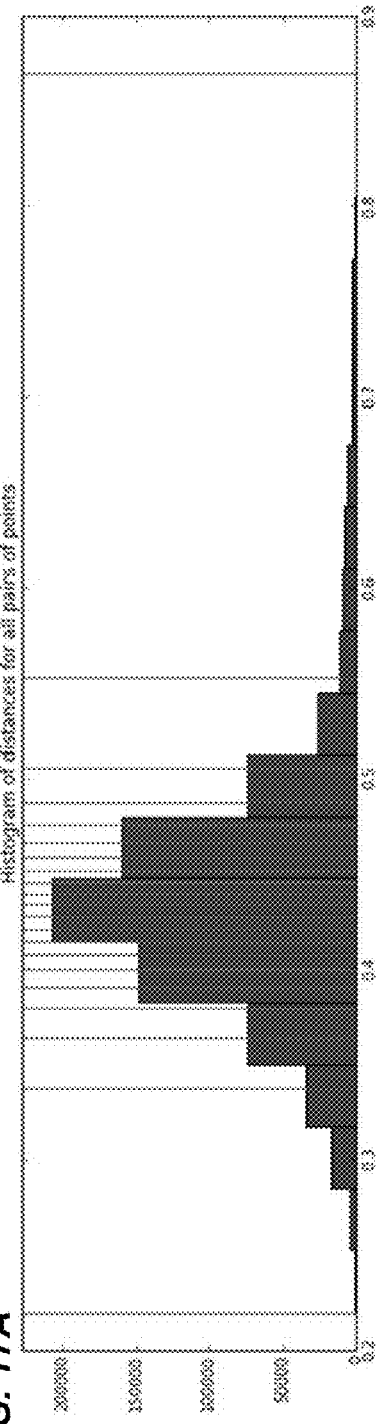
FIG. 17A
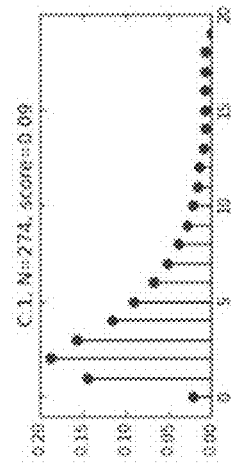
FIG. 17B
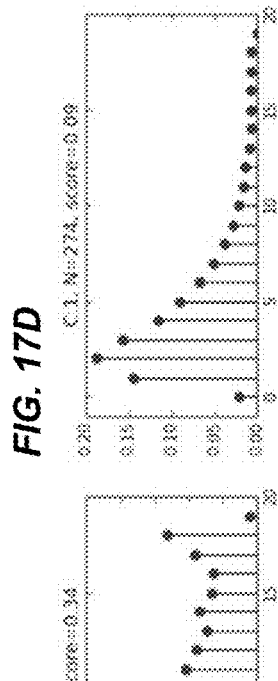
FIG. 17C
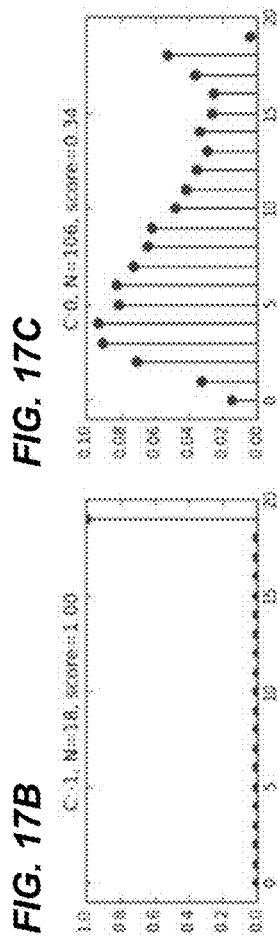
FIG. 17E
FIG. 17F
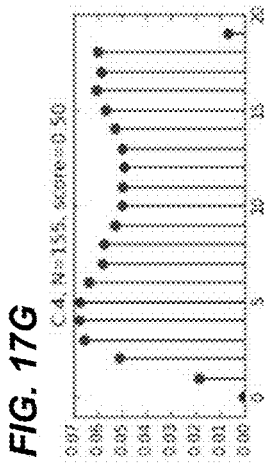
FIG. 17D
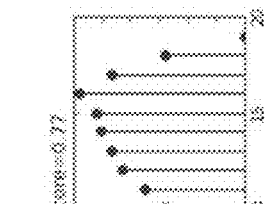
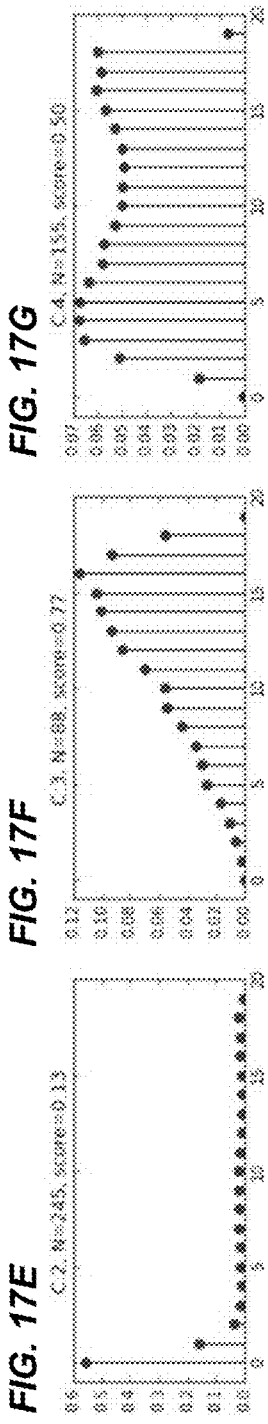
FIG. 17G

| FIG. 18A | FIG. 18B | FIG. 18C | FIG. 18D | FIG. 18E |
|---|---|---|---|---|

*FIG. 18*

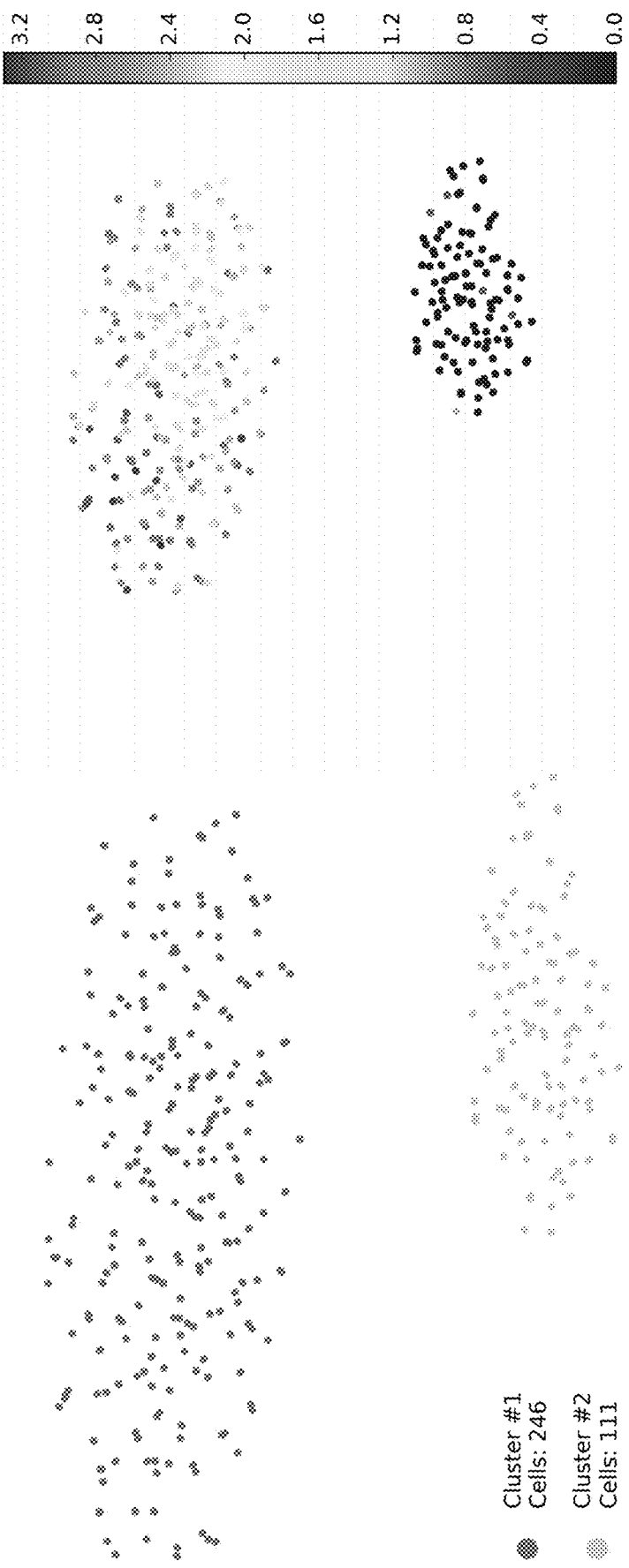

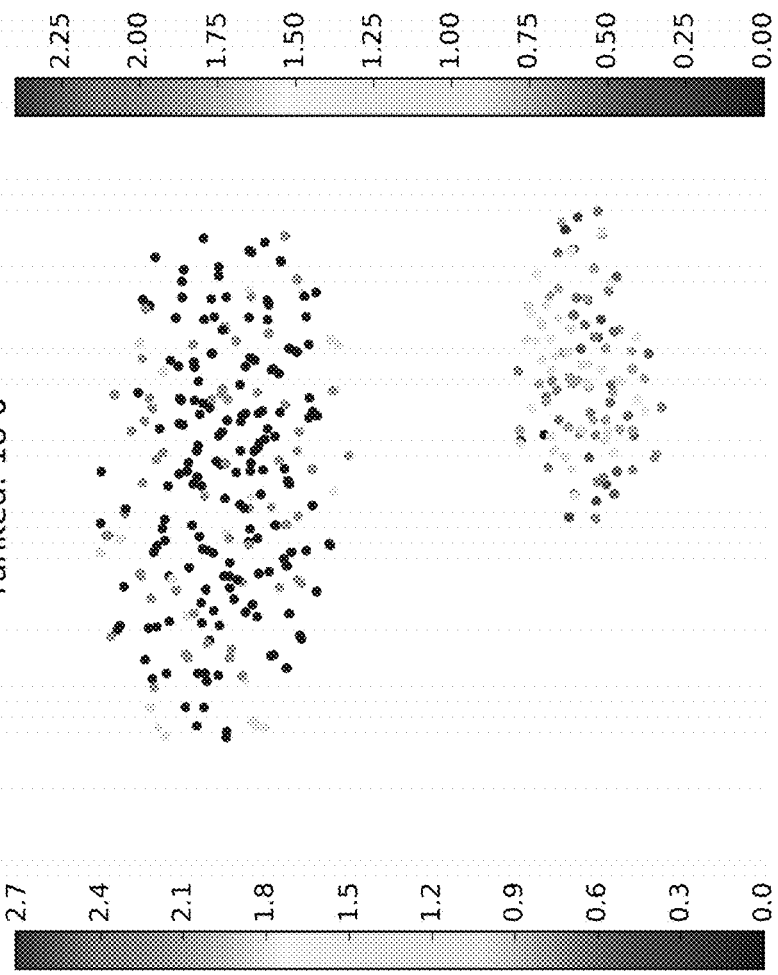
FIG. 21C  FIG. 21D

| FIG. 23A | FIG. 23B | FIG. 23C | FIG. 23D | FIG. 23E |

FIG. 23

METHODS FOR EXPRESSION PROFILE CLASSIFICATION

RELATED APPLICATIONS

The present application claims priority under 35 U.S.C. § 119(e) to U.S. Provisional Application No. 62/419,291, filed on Nov. 8, 2016; and U.S. Provisional Application No. 62/446,227, filed on Jan. 13, 2017. The content of each of these related applications is herein expressly incorporated by reference in its entirety.

COPYRIGHT AND TRADEMARK NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Field

The present disclosure relates generally to the field of classifying expression profiles and more particularly identifying targets to distinguish cell types.

Description of the Related Art

Methods and techniques such as barcoding (e.g., stochastic barcoding) are useful for cell analysis. For example, barcoding can be used to decipher gene expression profiles of single cells to determine their states using, for example, reverse transcription, polymerase chain reaction (PCR) amplification, and next generation sequencing (NGS). However, the large quantity of data generated by these methods and techniques need to be further analyzed to identify markers for distinguishing cell types and to determine the types of cells analyzed.

SUMMARY

Disclosed herein are methods for identifying targets to distinguish cell types. In some embodiments, the method comprises: (a) receiving a target counts data structure, wherein the target counts data structure comprises expression profiles of a plurality of cells, and wherein the expression profiles of the plurality of cells comprises a number of each target of a plurality of targets for each cell of the plurality of cells; (b) hierarchically clustering expression profiles of the plurality of cells based on the target counts data structure and distances between the expression profiles of the plurality of cells to generate a dendrogram representing the expression profiles of plurality of cells, wherein the dendrogram comprises a plurality of nodes, wherein the plurality of nodes comprise a root node, a plurality of leaf nodes, and a plurality of non-root, non-leaf nodes, wherein each leaf node of the plurality of leaf nodes represents an expression profile of a different cell of the plurality of cells, and wherein the root node represents expression profiles of the plurality of cells; (c) while traversing through each node of the plurality of nodes of the dendrogram from the root node of the dendrogram to the plurality of leaf nodes of the dendrogram: (1) determining whether a splitting of the node into child nodes of the node is valid or invalid (e.g., the differences between the child nodes are not significant); and (2) if the splitting of the node into the child nodes of the node is invalid, adding the node to a merging cluster set; (d) iteratively, for each first node in the merging cluster set, if a distance between the first node in the merging cluster set and a second node in the merging cluster set that is closest to the first node is within a merging distance threshold, merging the first node with the second node to generate a merged node comprising expression profiles represented by the first node and the second node; and (e) for each node in the merging cluster set, identifying targets for distinguishing cell types based on expression profiles of the plurality of targets of cells represented by the node.

In some embodiments, the target counts data structure comprises a target counts matrix. Each row or each column of the target counts matrix can comprise a number of each target of a plurality of targets for a different individual cell of the plurality of cells.

In some embodiments, each of the plurality of leaf nodes and the plurality of non-root, non-leaf nodes can be associated with a parent node, and each of the root node and the plurality of non-root, non-leaf nodes can be associated with a left child node and a right child node and represents expression profiles represented by the left child node and the right child node of the node.

In some embodiments, the method comprises, prior to receiving the target counts data structure in (a): (f) barcoding the plurality of targets in the plurality of cells using a plurality of barcodes to create a plurality of barcoded targets, wherein each of the plurality of barcodes comprises a cell label and a molecular label, wherein barcoded targets created from targets of different cells have different cell labels, and wherein barcoded targets created from targets of one cell of the plurality of cells have different molecular labels; (g) obtaining sequencing data of the plurality of barcoded targets; and (h) for each of the plurality of cells: (1) counting the number of molecular labels with distinct sequences associated with each target of the plurality of targets in the sequencing data for the cell; and (2) estimating the number of each target of the plurality of targets for the cell based on the number of molecular labels with distinct sequences associated with the target in the sequencing data counted in (h)(1). For example, the method can comprise, prior to receiving the target counts data structure in (a): step(s) (f) stochastically barcoding the plurality of targets in the plurality of cells using a plurality of stochastic barcodes to create a plurality of stochastically barcoded targets, wherein each of the plurality of stochastic barcodes comprises a cell label and a molecular label, wherein stochastically barcoded targets created from targets of different cells have different cell labels, and wherein stochastically barcoded targets created from targets of one cell of the plurality of cells have different molecular labels; and/or (g) obtaining sequencing data of the plurality of stochastically barcoded targets. Receiving the target counts data structure can comprise: generating a target counts data structure from the number of each target of the plurality of targets for the cell estimated in (h)(2), wherein the expression profile of the cell of the plurality of cells comprises the number of each target of the plurality of targets for the cell estimated in (h)(2).

In some embodiments, the method comprises prior to hierarchically clustering the expression profiles of the plurality of cells based on the target counts data structure and the distances between the expression profiles of the plurality of cells to generate the dendrogram representing the expression profiles of the plurality of cells in (b): (i) determining a distance data structure of elements of the target counts matrix, wherein the distance data structure comprises distances between the expression profiles of the plurality of cells. The distance data structure can comprise a distance matrix. Each diagonal element of the distance matrix can have a value of zero. Hierarchically clustering the expression profiles of the plurality of cells based on the target counts data structure and the distances between the expression profiles of the plurality of cells to generate the dendrogram representing the expression profiles of the plurality of cells in (b) can comprise hierarchically clustering the expression profiles of the plurality of cells based on the target counts data structure and the distance data structure. The distances between the expression profiles of the plurality of cells can comprise pairwise correlation distances between the expression profiles of the plurality of cells.

In some embodiments, prior to determining the distance data structure of elements of the target counts data structure in (i), log-transforming the target counts data structure into a log-transformed target counts data structure, wherein determining the distance data structure of elements of the target counts data structure comprises determining the distance data structure of the log-transformed target counts data structure, and wherein hierarchically clustering the expression profiles of the plurality of cells based on the target counts data structure and the distances between the expression profiles of the plurality of cells in (b) comprises: hierarchically clustering the expression profiles of the plurality of cells based on the log-transformed target counts data structure and the distance data structure to generate the dendrogram. Log-transforming the target counts data structure into the log-transformed target counts data structure can comprise increasing the value of each element of the target counts data structure by an increment (such as one).

In some embodiments, hierarchically clustering the expression profiles of the plurality of cells based on the target counts data structure and the distances between the expression profiles of the plurality of cells in (b) comprises: assigning each expression profile of the plurality of cells to a different leaf node; and iteratively combining a first node and a second node of the plurality of nodes to generate a parent node of the first node and the second node if the second node is the closest node of the plurality of nodes to the first node. The distance between the first node and the second node is the maximum distance between any cell with an expression profile represented by the first node and any cell with an expression profile represented by the second node.

In some embodiments, the method comprises: at each node when traversing the plurality of nodes of the dendrogram: if the splitting is valid, continuing traversing from the node to the left child node and the right child node of the node; and if the splitting is invalid, discontinuing traversing from the node to the left child node and the right child node of the node. At least one of an intra-node correlation of the first node and an intra-node correlation of the second node can be higher than an inter-node correlation of the first node and the second node. A measure or an indication of an intra-node correlation of the first node and an intra-node correlation of the second node can be higher than an inter-node correlation of the first node and the second node. The measure of the intra-node correlation of the first node and the intra-node correlation of the second node can be based on at least one of: an intra-node maximum correlation of the first node and the second node, an intra-node average correlation of the first node and the second node, an intra-node median correlation of the first node and the second node, an intra-node minimum correlation of the first node and the second node, and any combinations thereof. The intra-node correlation of the first node can be based on at least one of: an intra-node maximum correlation of the first node, an intra-node average correlation of the first node, an intra-node median correlation of the first node, an intra-node minimum correlation of the first node, and any combinations thereof. The intra-node correlation of the second node can be based on at least one of: an intra-node maximum correlation of the second node, an intra-node average correlation of the second node, an intra-node median correlation of the second node, an intra-node minimum correlation of the second node, and any combinations thereof. The inter-node correlation of the first node and the second node can be based on at least one of: an inter-node maximum correlation of the first node and the second node, an inter-node average correlation of the first node and the second node, an inter-node median correlation of the first node and the second node, an inter-node minimum correlation of the first node and the second node, and any combinations thereof.

In some embodiments, determining whether the splitting of the node with the child nodes of the node is valid or invalid comprises: determining the splitting to be valid if the distance between the left child node and the right child node is above a splitting threshold, and otherwise invalid. The distance between the left child node and the right child node can be determined based on a statistical test performed on each target of the plurality of targets between expression profiles represented by the left child node and the right child node. The statistical test can comprise a Welch's t-test. The distance between the left child node and the right child node can be determined based on the maximum p-value of the statistical test performed on the each target of the plurality of targets between each expression profile represented by the left child node and each expression profile represented by the right child node.

In some embodiments, determining whether the splitting of the node with the child nodes of the node is valid or invalid comprises: determining the splitting to be valid if at least one of an intra-node correlation of the first node and an intra-node correlation of the second node is higher than an inter-node correlation of the first node and the second node, and invalid if otherwise. In some embodiments, determining whether the splitting of the node with the child nodes of the node is valid or invalid comprises: determining the splitting to be valid if a measure or an indication of an intra-node correlation of the first node and an intra-node correlation of the second node is higher than an inter-node correlation of the first node and the second node, and invalid if otherwise. The measure of the intra-node correlation of the first node and the intra-node correlation of the second node can be based on at least one of: an intra-node maximum correlation of the first node and the second node, an intra-node average correlation of the first node and the second node, an intra-node median correlation of the first node and the second node, an intra-node minimum correlation of the first node and the second node, and any combinations thereof. The intra-node correlation of the first node can be based on at least one of: an intra-node maximum correlation of the first node, an intra-node average correlation of the first node, an intra-node median correlation of the first node, an intra-node minimum correlation of the first node, and any combinations thereof. The intra-node correlation of the second node can be based on at least one of: an intra-node maximum correlation of the second node, an intra-node average correlation of the second node, an intra-node median correlation of the second node, an intra-node minimum correlation of the second node, and any combinations thereof. The inter-node correlation of the first node and the second node can be based on at least one of: an inter-node maximum correlation of the first node and the second node, an inter-node average correlation of the first node and the second node, an inter-node median correlation of the first node and the second node, an inter-node minimum correlation of the first node and the second node, and any combinations thereof.

In some embodiments, the method comprises: at each node when traversing the plurality of nodes of the dendrogram: (3) adding the node to the merging cluster set if the node represents an expression profile of a single cell. In some embodiments, the method can comprise at each node when traversing the plurality of nodes of the dendrogram: assigning a node label to the node. If the node represents an expression profile of a single cell, the node label of the node comprises a single cell designation, otherwise, if the node is the left child node of the parent node, the node label of the node comprises the node label of the parent node and a left designation, and otherwise, the node label of the node comprises the node label of the parent node and a right designation.

In some embodiments, for each node in the merging cluster set, identifying the targets for distinguishing the cell types based on the expression profiles of the plurality of targets of the cells represented by the node comprises: determining a difference, between expression profiles represented by the node and expression profiles represented by another node in the merging cluster set, in the numbers of molecular labels with distinct sequences associated with the targets for distinguishing the cell types is greater than a significance threshold.

In some embodiments, the method comprises, prior to merging the first node with the second node to generate the merged node in (d): merging each third node in the merging cluster set representing an expression profile of a single cell with a fourth node in the merging cluster set if a distance between the third node and the fourth node is within a node distance threshold. In some embodiments, the method comprises classifying the plurality of cells based on the nodes in the merging cluster set that represent expression profiles of the cells. The method can comprise designing a whole transcriptome assay based on the targets for distinguishing cell types identified. In some embodiments, the method can comprise designing a targeted transcriptome assay based on the targets for distinguishing cell types identified.

Disclosed herein are methods for identifying targets for distinguishing cell types. In some embodiments, the method comprises: (a) receiving expression profiles of a plurality of cells, wherein the expression profiles comprise a number of each target of a plurality of targets for each cell of the plurality of cells; (b) hierarchically clustering the expression profiles of the plurality of cells based on the target counts matrix and distances between the expression profiles of the plurality of cells to generate a dendrogram representing the expression profiles of plurality of cells, wherein the dendrogram comprises a plurality of nodes, wherein the plurality of nodes comprise a root node, a plurality of leaf nodes, and a plurality of non-root, non-leaf nodes, wherein each leaf node of the plurality of leaf nodes represents an expression profile of a different cell of the plurality of cells, and wherein the root node represents expression profiles of the plurality of cells; (c) while traversing through each node of the plurality of nodes of the dendrogram from the root node of the dendrogram to the plurality of leaf nodes of the dendrogram: (1) determining whether two sub-branches of the node (for example, represented by the child nodes of the node) are significantly different; and (2) if the two sub-branches of the node are significantly different, splitting the node into two cluster sets (for example, by traversing to the two sub-branches of the node). In some embodiments, the method comprises, (3) if the splitting of the node into the child nodes of the node is invalid, adding the node to a merging cluster set. In some embodiments, the method comprises: (d) iteratively, for each first node in the merging cluster set, if a distance between the first node in the merging cluster set and a second node in the merging cluster set that is closest to the first node is within a merging distance threshold, merging the first node with the second node to generate a merged node in the merging cluster set; and (e) for each node in the merging cluster set, identifying targets for distinguishing cell types based on expression profiles of the plurality of targets of cells represented by the node.

Disclosed herein are methods for identifying targets for distinguishing cell types. In some embodiments, the method comprises: (a) receiving expression profiles of a plurality of cells, wherein the expression profiles comprise a number of each target of a plurality of targets for each cell of the plurality of cells; (b) clustering the expression profiles of the plurality of cells to generate a plurality of clusters of expression profiles based on the distances between the expression profiles of the plurality of cells, wherein each cluster has one or more associations with one or both of (1) a parent cluster and (2) two or more child clusters, wherein the parent cluster represents expression profiles of one or more cells of the plurality of cells represented by the cluster, and wherein the cluster represents expression profiles represented by the two or more child clusters; (c) for each cluster with two or more child clusters, if associations between the cluster with the two or more child clusters are invalid (e.g., the differences between the two or more child clusters are not significant), adding the cluster to a merging cluster set; (d) iteratively, for each first cluster in the merging cluster set, if a distance between the first cluster in the merging cluster set and a second cluster in the merging cluster set that is closest to the first cluster is within a merging distance threshold, merging the first cluster and the second cluster to generate a merged cluster, wherein the merged cluster comprises expression profiles of the first cluster and the second cluster; and (e) for each cluster in the merging cluster set, identifying targets for distinguishing cell types based on expression profiles of the plurality of targets of cells represented by the cluster.

In some embodiments, receiving expression profiles of the plurality of cells comprises receiving a target counts data structure. The target counts data structure can comprise a target counts matrix. Each row or each column of the target counts matrix can comprise an expression profile of a different individual cell of the plurality of cells. Clustering the expression profiles of the plurality of cells into the plurality of clusters of expression profiles based on the distances between the expression profiles of the plurality of cells can comprise: hierarchically clustering the expression profiles of the plurality of cells to generate a dendrogram representing the expression profiles of the plurality of cells based on the distances between the expression profiles of the plurality of cells. The dendrogram can comprise the plurality of clusters. The plurality of clusters can comprise a root cluster, a plurality of leaf clusters, and a plurality of non-root, non-leaf clusters. A leaf cluster can represent an expression profile of a cell. A non-root, non-leaf cluster can represent expression profiles of cells represented by the child clusters of the non-root, non-leaf clusters. The root cluster can represent expression profiles of its child clusters.

Each of the plurality of leaf clusters and the plurality of non-root, non-leaf clusters can have an association with a parent cluster. Each of the root cluster and the plurality of non-root, non-leaf clusters can have associations with a left child cluster and a right child cluster and represents expression profiles represented by the left child cluster and the right child cluster of the cluster. The root cluster can represent the expression profiles of the plurality of cells.

In some embodiments, for each cluster with two or more child clusters, if associations between the cluster with the two or more child clusters are invalid, adding the cluster to a merging cluster set comprises: while traversing through each cluster of the dendrogram from the root cluster of the dendrogram to the plurality of leaf clusters of the dendrogram: (1) determining whether associations of the cluster with child clusters of the cluster are valid or invalid; and (2) if the associations are invalid, adding the cluster to a merging cluster set.

In some embodiments, the method comprises: prior to receiving the expression profiles of the plurality of cells in (a): (f) barcoding the plurality of targets in the plurality of cells using a plurality of barcodes to create a plurality of barcoded targets, wherein each of the plurality of barcodes comprises a cell label and a molecular label, wherein barcoded targets created from targets of different cells have different cell labels, and wherein barcoded targets created from targets of one cell of the plurality of cells have different molecular labels; (g) obtaining sequencing data of the plurality of barcoded targets; and (h) for each of the plurality of cells: (1) counting the number of molecular labels with distinct sequences associated with each target of the plurality of targets in the sequencing data for the cell; and (2) estimating the number of each target of the plurality of targets for the cell based on the number of molecular labels with distinct sequences associated with the target in the sequencing data counted in (h)(1). For example, the method can comprise: prior to receiving the expression profiles of the plurality of cells in (a): step(s) (f) stochastically barcoding the plurality of targets in the plurality of cells using a plurality of stochastic barcodes to create a plurality of stochastically barcoded targets, wherein each of the plurality of stochastic barcodes comprises a cell label and a molecular label, wherein stochastically barcoded targets created from targets of different cells have different cell labels, and wherein stochastically barcoded targets created from targets of one cell of the plurality of cells have different molecular labels; and/or (g) obtaining sequencing data of the plurality of stochastically barcoded targets In some embodiments, the expression profile of the cell of the plurality of cells comprises the number of each target of the plurality of targets for the cell estimated in (h)(2). In some embodiments, the method comprises, prior to clustering expression profiles of the plurality of cells to generate the plurality of clusters of expression profiles based on the distances between the expression profiles of the plurality of cells in (b): (i) determining a distance data structure of the expression profiles of the plurality of cells. The distance data structure can comprise a distance matrix of the expression profiles of the plurality of cells. Each diagonal element of the distance matrix has a value of zero. Clustering the expression profiles of the plurality of cells to generate the plurality of clusters of expression profiles based on the distances between the expression profiles of the plurality of cells in (b) can comprise: clustering the expression profiles of the plurality of cells to generate the plurality of clusters of expression profiles based on the distance matrix. The distances between the expression profiles of the plurality of cells can be pairwise correlation distances between the expression profiles of the plurality of cells.

In some embodiments, the method comprises, prior to determining the distance data structure in (i), log-transforming the target counts data structure into a log-transformed target counts data structure, wherein determining the distance data structure of elements of the target counts data structure comprises determining the distance data structure of the log-transformed target counts data structure, and wherein clustering the expression profiles of the plurality of cells to generate the plurality of clusters of expression profiles based on the distances between the expression profiles of the plurality of cells in (b) comprises clustering the expression profiles of the plurality of cells based on the log-transformed target counts data structure and the distance data structure to generate the plurality of clusters. Log-transforming the target counts data structure into the log-transformed target counts data structure can comprise increasing the value of each element of the target counts data structure by an increment. The increment can be one.

In some embodiments, clustering the expression profiles of the plurality of cells based on distances between the expression profiles of the plurality of cells in (b) comprises: assigning each expression profile of the plurality of cells to a different leaf cluster in the plurality of clusters; and iteratively combining a first cluster and a second cluster of the plurality of clusters to generate a parent cluster of the first cluster and the second cluster if the second cluster is the closest cluster of the plurality of cluster to the first cluster. The distance between the first cluster and the second cluster can be the maximum distance between any expression profile represented by the first cluster and any expression profile represented by the second cluster.

In some embodiments, an intra-cluster correlation of the first cluster and an intra-cluster correlation of the second cluster are higher than an inter-cluster correlation of the first cluster and the second cluster. A measure or an indication of an intra-cluster correlation of the first cluster and an intra-cluster correlation of the second cluster is higher than an inter-cluster correlation of the first cluster and the second cluster. The measure of the intra-cluster correlation of the first cluster and the intra-cluster correlation of the second cluster can be based on at least one of: an intra-cluster maximum correlation of the first cluster and the second cluster, an intra-cluster average correlation of the first cluster and the second cluster, an intra-cluster median correlation of the first cluster and the second cluster, an intra-cluster minimum correlation of the first cluster and the second cluster, and any combinations thereof. The intra-cluster correlation of the first cluster can be based on at least one of: an intra-cluster maximum correlation of the first cluster, an intra-cluster average correlation of the first cluster, an intra-cluster median correlation of the first cluster, an intra-cluster minimum correlation of the first cluster, and any combinations thereof. The intra-cluster correlation of the second cluster can be based on at least one of: an intra-cluster maximum correlation of the second cluster, an intra-cluster average correlation of the second cluster, an intra-cluster median correlation of the second cluster, an intra-cluster minimum correlation of the second cluster, and any combinations thereof. The inter-cluster correlation of the first cluster and the second cluster can be based on at least one of: an inter-cluster maximum correlation of the first cluster and the second cluster, an inter-cluster average correlation of the first cluster and the second cluster, an inter-cluster median correlation of the first cluster and the second cluster, an inter-cluster minimum correlation of the first cluster and the second cluster, and any combinations thereof.

In some embodiments, the method comprises, at each cluster when traversing the plurality of clusters of the dendrogram: if the associations are valid, continuing traversing from the cluster to the left child cluster and the right child cluster of the cluster; and if the associations are invalid, discontinuing traversing from the cluster to the left child cluster and the right child cluster of the cluster. Determining whether the associations of the cluster with the child clusters of the cluster are valid or invalid can comprise: determining the associations to be valid if the distance between the left child cluster and the right child cluster is above an association threshold, and otherwise invalid.

In some embodiments, the distance between the left child cluster and the right child cluster can be determined based on a statistical test performed on each target of the plurality of targets between expression profiles represented by the left child cluster and the right child cluster. The statistical test can comprise a Welch's t-test. The distance between the left child cluster and the right child cluster can be determined based on the maximum p-value of the statistical test performed on the each target of the plurality of targets between expression profile represented by the left child cluster and each expression profile represented by the right child cluster.

In some embodiments, determining whether the associations of the cluster with the child clusters of the cluster are valid or invalid can comprise: determining the associations to be valid if at least one of an intra-cluster correlation of the first cluster and an intra-cluster correlation of the second cluster is higher than an inter-cluster correlation of the first cluster and the second cluster, and otherwise invalid. In some embodiments, determining whether the associations of the cluster with the child clusters of the cluster are valid or invalid can comprise: determining the associations to be valid if a measure or an indication of an intra-cluster correlation of the first cluster and an intra-cluster correlation of the second cluster is higher than an inter-cluster correlation of the first cluster and the second cluster. The measure of the intra-cluster correlation of the first cluster and the intra-cluster correlation of the second cluster can be based on at least one of: an intra-cluster maximum correlation of the first cluster and the second cluster, an intra-cluster average correlation of the first cluster and the second cluster, an intra-cluster median correlation of the first cluster and the second cluster, an intra-cluster minimum correlation of the first cluster and the second cluster, and any combinations thereof. The intra-cluster correlation of the first cluster can be based on at least one of: an intra-cluster maximum correlation of the first cluster, an intra-cluster average correlation of the first cluster, an intra-cluster median correlation of the first cluster, an intra-cluster minimum correlation of the first cluster, and any combinations thereof. The intra-cluster correlation of the second cluster can be based on at least one of: an intra-cluster maximum correlation of the second cluster, an intra-cluster average correlation of the second cluster, an intra-cluster median correlation of the second cluster, an intra-cluster minimum correlation of the second cluster, or and combinations thereof. The inter-cluster correlation of the first cluster and the second cluster can be based on at least one of: an inter-cluster maximum correlation of the first cluster and the second cluster, an inter-cluster average correlation of the first cluster and the second cluster, an inter-cluster median correlation of the first cluster and the second cluster, an inter-cluster minimum correlation of the first cluster and the second cluster, and any combinations thereof.

In some embodiments, the method comprises, at each cluster when traversing the plurality of clusters of the dendrogram: (3) adding the cluster to the merging cluster set if the cluster represents an expression profile of a single cell. The method can comprise, at each cluster when traversing the plurality of clusters of the dendrogram: assigning a cluster label to the cluster. In some embodiments, if the cluster represents an expression profile of a single cell, the cluster label of the cluster comprises a single cell designation, otherwise, if the cluster is the left child cluster of the parent cluster, the cluster label of the cluster comprises the cluster label of the parent cluster and a left designation, and otherwise, the cluster label of the cluster comprises the cluster label of the parent cluster and a right designation.

In some embodiments, for each cluster in the merging cluster set, identifying the targets for distinguishing the cell types based on the expression profiles of the plurality of targets of the cells represented by the cluster comprises: determining a difference, between expression profiles represented by the cluster and expression profiles represented by another cluster in the merging cluster set, in numbers of molecular labels with distinct sequences associated with the targets for distinguishing the cell types is greater than a significance threshold.

In some embodiments, the method comprises, prior to merging the first cluster with the second cluster to generate the merged cluster in (d): merging each third cluster in the merging cluster set representing an expression profile of a single cell with a fourth cluster in the merging cluster set if a distance between the third cluster and the fourth cluster is within a cluster distance threshold. The method can comprise classifying the plurality of cells based on the clusters in the merging cluster set that represent expression profiles of the cells. The method can comprise designing a whole transcriptome assay based on the targets for distinguishing cell types identified or designing a targeted transcriptome assay based on the targets for distinguishing cell types identified.

Disclosed herein are systems for identifying targets for distinguishing cell types. In some embodiments, the system comprises: a hardware processor; and non-transitory memory having instructions stored thereon, which when executed by the hardware processor cause the processor to perform any of the methods disclosed herein. Disclosed herein are computer readable media for identifying targets for distinguishing cell types. In some embodiments, the computer readable medium comprises code for performing any of the methods disclosed herein.

Disclosed herein are embodiments of a system for identifying targets for distinguishing cell types. In some embodiments, the system comprises: non-transitory memory configured to store executable instructions, and a hardware processor in communication with the non-transitory memory, the hardware processor programmed by executable instructions to: (a) receive a target counts data structure, wherein the target counts data structure comprises expression profiles of a plurality of cells, and wherein the expression profiles of the plurality of cells comprises a number of each target of a plurality of targets for each cell of the plurality of cells; (b) hierarchically cluster expression profiles of the plurality of cells based on the target counts data structure and distances between the expression profiles of the plurality of cells to generate a dendrogram representing the expression profiles of plurality of cells, wherein the dendrogram comprises a plurality of nodes, wherein the plurality of nodes comprise a root node, a plurality of leaf nodes, and a plurality of non-root, non-leaf nodes, wherein each leaf node of the plurality of leaf nodes represents an expression profile of a different cell of the plurality of cells, and wherein the root node represents expression profiles of the plurality of cells; (c) while traversing through each node of the plurality of nodes of the dendrogram from the root node of the dendrogram to the plurality of leaf nodes of the dendrogram: (1) determine whether a splitting of the node into child nodes of the node is valid or invalid; and (2) if the splitting of the node into the child nodes of the node is invalid, add the node to a merging cluster set; (d) iteratively, for each first node in the merging cluster set, if a distance between the first node in the merging cluster set and a second node in the merging cluster set that is closest to the first node is within a merging distance threshold, merge the first node with the second node to generate a merged node comprising expression profiles represented by the first node and the second node; and (e) for each node in the merging cluster set, identify targets for distinguishing cell types based on expression profiles of the plurality of targets of cells represented by the node.

In some embodiments, the target counts data structure comprises a target counts matrix. Each row or each column of the target counts matrix can comprise a number of each target of a plurality of targets for a different individual cell of the plurality of cells. Each of the plurality of leaf nodes and the plurality of non-root, non-leaf nodes can be associated with a parent node, and each of the root node and the plurality of non-root, non-leaf nodes can be associated with a left child node and a right child node and represents expression profiles represented by the left child node and the right child node of the node.

In some embodiments, the hardware processor can be programmed to, prior to receiving the target counts data structure in (a): (f) cause barcode the plurality of targets in the plurality of cells using a plurality of barcodes to create a plurality of barcoded targets, wherein each of the plurality of barcodes comprises a cell label and a molecular label, wherein barcoded targets created from targets of different cells have different cell labels, and wherein barcoded targets created from targets of one cell of the plurality of cells have different molecular labels; (g) obtain sequencing data of the plurality of barcoded targets; and (h) for each of the plurality of cells: (1) count the number of molecular labels with distinct sequences associated with each target of the plurality of targets in the sequencing data for the cell; and (2) estimate the number of each target of the plurality of targets for the cell based on the number of molecular labels with distinct sequences associated with the target in the sequencing data counted in (h)(1). To receive the target counts data structure, the hardware processor can be programmed to: generate a target counts data structure from the number of each target of the plurality of targets for the cell estimated in (h)(2), wherein the expression profile of the cell of the plurality of cells comprises the number of each target of the plurality of targets for the cell estimated in (h)(2).

In some embodiments, the hardware processor can be programmed to, prior to hierarchically clustering the expression profiles of the plurality of cells based on the target counts data structure and the distances between the expression profiles of the plurality of cells to generate the dendrogram representing the expression profiles of the plurality of cells in (b): (i) determine a distance data structure of elements of the target counts data structure, wherein the distance data structure comprises distances between the expression profiles of the plurality of cells. The distance data structure comprises a distance matrix. Each diagonal element of the distance matrix has a value of zero.

In some embodiments, to hierarchically cluster the expression profiles of the plurality of cells based on the target counts data structure and the distances between the expression profiles of the plurality of cells to generate the dendrogram representing the expression profiles of the plurality of cells in (b), the hardware processor can be programmed to: hierarchically cluster the expression profiles of the plurality of cells based on the target counts data structure and the distance data structure. The distances between the expression profiles of the plurality of cells can comprise pairwise correlation distances between the expression profiles of the plurality of cells.

In some embodiments, the hardware processor can be programmed to, prior to determining the distance data structure of elements of the target counts data structure in (i), log-transform the target counts data structure into a log-transformed target counts data structure. To determine the distance data structure of elements of the target counts data structure, the hardware processor can be programmed to: determine the distance data structure of the log-transformed target counts data structure. To hierarchically cluster the expression profiles of the plurality of cells based on the target counts data structure and the distances between the expression profiles of the plurality of cells in (b), the hardware processor can be programmed to: hierarchically cluster the expression profiles of the plurality of cells based on the log-transformed target counts data structure and the distance data structure to generate the dendrogram. To log-transform the target counts data structure into the log-transformed target counts data structure, the hardware processor can be programmed to: increase the value of each element of the target counts data structure by an increment. The increment can be one.

To hierarchically cluster the expression profiles of the plurality of cells based on the target counts data structure and the distances between the expression profiles of the plurality of cells in (b), the hardware processor can be programmed to: assign each expression profile of the plurality of cells to a different leaf node; and iteratively combine a first node and a second node of the plurality of nodes to generate a parent node of the first node and the second node if the second node is the closest node of the plurality of nodes to the first node. The distance between the first node and the second node can be the maximum distance between any cell with an expression profile represented by the first node and any cell with an expression profile represented by the second node.

In some embodiments, at least one of an intra-node correlation of the first node and an intra-node correlation of the second node can be higher than an inter-node correlation of the first node and the second node. A measure or an indication of an intra-node correlation of the first node and an intra-node correlation of the second node can be higher than an inter-node correlation of the first node and the second node. The measure of the intra-node correlation of the first node and the intra-node correlation of the second node can be based on at least one of: an intra-node maximum correlation of the first node and the second node, an intra-node average correlation of the first node and the second node, an intra-node median correlation of the first node and the second node, an intra-node minimum correlation of the first node and the second node, and any combinations thereof. The intra-node correlation of the first node can be based on at least one of: an intra-node maximum correlation of the first node, an intra-node average correlation of the first node, an intra-node median correlation of the first node, an intra-node minimum correlation of the first node, and any combinations thereof. The intra-node correlation of the second node can be based on at least one of: an intra-node maximum correlation of the second node, an intra-node average correlation of the second node, an intra-node median correlation of the second node, an intra-node minimum correlation of the second node, and any combinations thereof. The inter-node correlation of the first node and the second node can be based on at least one of: an inter-node maximum correlation of the first node and the second node, an inter-node average correlation of the first node and the second node, an inter-node median correlation of the first node and the second node, an inter-node minimum correlation of the first node and the second node, and any combinations thereof.

In some embodiments, the hardware processor can be programmed to, at each node when traversing the plurality of nodes of the dendrogram: if the splitting is valid, continue traversing from the node to the left child node and the right child node of the node; and if the splitting is invalid, discontinue traversing from the node to the left child node and the right child node of the node. To determine whether the splitting of the node with the child nodes of the node is valid or invalid, the hardware processor can be programmed to: determine the splitting to be valid if the distance between the left child node and the right child node is above a splitting threshold, and otherwise invalid. The distance between the left child node and the right child node can be determined based on a statistical test performed on each target of the plurality of targets between expression profiles represented by the left child node and the right child node. The statistical test can comprise a Welch's t-test. The distance between the left child node and the right child node can be determined based on the maximum p-value of the statistical test performed on the each target of the plurality of targets between each expression profile represented by the left child node and each expression profile represented by the right child node.

In some embodiments, the hardware processor can be programmed to, at each node when traversing the plurality of nodes of the dendrogram: (3) add the node to the merging cluster set if the node represents an expression profile of a single cell. In some embodiments, at each node when traversing the plurality of nodes of the dendrogram, the hardware processor can be programmed to: assign a node label to the node. If the node represents an expression profile of a single cell, the node label of the node can comprise a single cell designation, otherwise, if the node is the left child node of the parent node, the node label of the node can comprise the node label of the parent node and a left designation, and otherwise, the node label of the node can comprise the node label of the parent node and a right designation.

In some embodiments, for each node in the merging cluster set, identifying the targets for distinguishing the cell types based on the expression profiles of the plurality of targets of the cells represented by the node, the hardware processor can be programmed to: determine a difference, between expression profiles represented by the node and expression profiles represented by another node in the merging cluster set, in the numbers of molecular labels with distinct sequences associated with the targets for distinguishing the cell types is greater than a significance threshold.

In some embodiments, the hardware processor can be programmed to: prior to merging the first node with the second node to generate the merged node in (d): merge each third node in the merging cluster set representing an expression profile of a single cell with a fourth node in the merging cluster set if a distance between the third node and the fourth node is within a node distance threshold. The hardware processor can be programmed to: classify the plurality of cells based on the nodes in the merging cluster set that represent expression profiles of the cells. The hardware processor can be programmed to: design a whole transcriptome assay based on the targets for distinguishing cell types identified. The hardware processor can be programmed to: design a targeted transcriptome assay based on the targets for distinguishing cell types identified.

Disclosed herein are embodiments of a system for identifying targets for distinguishing cell types. In some embodiments, the system comprises: non-transitory memory configured to store executable instructions, and a hardware processor in communication with the non-transitory memory, the hardware processor programmed by executable instructions to: (a) receive expression profiles of a plurality of cells, wherein the expression profiles comprise a number of each target of a plurality of targets for each cell of the plurality of cells; (b) cluster the expression profiles of the plurality of cells to generate a plurality of clusters of expression profiles based on the distances between the expression profiles of the plurality of cells, wherein each cluster has one or more associations with one or both of (1) a parent cluster and (2) two or more child clusters, wherein the parent cluster represents expression profiles of one or more cells of the plurality of cells represented by the cluster, and wherein the cluster represents expression profiles represented by the two or more child clusters; (c) for each cluster with two or more child clusters, if associations between the cluster with the two or more child clusters are invalid, add the cluster to a merging cluster set; (d) iteratively, for each first cluster in the merging cluster set, if a distance between the first cluster in the merging cluster set and a second cluster in the merging cluster set that is closest to the first cluster is within a merging distance threshold, merge the first cluster and the second cluster to generate a merged cluster, wherein the merged cluster comprises expression profiles of the first cluster and the second cluster; and (e) for each cluster in the merging cluster set, identify targets for distinguishing cell types based on expression profiles of the plurality of targets of cells represented by the cluster.

In some embodiments, the hardware processor can be programmed to: receive expression profiles of the plurality of cells comprises receiving a target counts data structure. The target counts data structure can comprise a target counts matrix. Each row or each column of the target counts matrix can comprise an expression profile of a different individual cell of the plurality of cells.

In some embodiments, to cluster the expression profiles of the plurality of cells into the plurality of clusters of expression profiles based on the distances between the expression profiles of the plurality of cells, the hardware processor can be programmed to: hierarchically cluster the expression profiles of the plurality of cells to generate a dendrogram representing the expression profiles of the plurality of cells based on the distances between the expression profiles of the plurality of cells, wherein the dendrogram comprises the plurality of clusters, wherein the plurality of clusters comprise a root cluster, a plurality of leaf clusters, and a plurality of non-root, non-leaf clusters. Each of the plurality of leaf clusters and the plurality of non-root, non-leaf clusters can have an association with a parent cluster. Each of the root cluster and the plurality of non-root, non-leaf clusters can have associations with a left child cluster and a right child cluster and represents expression profiles represented by the left child cluster and the right child cluster of the cluster. The root cluster can represent the expression profiles of the plurality of cells. For each cluster with two or more child clusters, if associations between the cluster with the two or more child clusters are invalid, adding the cluster to a merging cluster set, the hardware processor can be programmed to, while traversing through each cluster of the dendrogram from the root cluster of the dendrogram to the plurality of leaf clusters of the dendrogram: (1) determine whether associations of the cluster with child clusters of the cluster are valid or invalid; and (2) if the associations are invalid, add the cluster to a merging cluster set.

In some embodiments, the hardware processor can be programmed to, prior to receiving the expression profiles of the plurality of cells in (a): (f) barcode the plurality of targets in the plurality of cells using a plurality of barcodes to create a plurality of barcoded targets, wherein each of the plurality of barcodes comprises a cell label and a molecular label, wherein barcoded targets created from targets of different cells have different cell labels, and wherein barcoded targets created from targets of one cell of the plurality of cells have different molecular labels; (g) obtain sequencing data of the plurality of barcoded targets; and (h) for each of the plurality of cells: (1) count the number of molecular labels with distinct sequences associated with each target of the plurality of targets in the sequencing data for the cell; and (2) estimate the number of each target of the plurality of targets for the cell based on the number of molecular labels with distinct sequences associated with the target in the sequencing data counted in (h)(1). The expression profile of the cell of the plurality of cells can comprise the number of each target of the plurality of targets for the cell estimated in (h)(2).

In some embodiments, the hardware processor can be programmed to, prior to clustering the expression profiles of the plurality of cells to generate the plurality of clusters of expression profiles based on the distances between the expression profiles of the plurality of cells in (b): (i) determine a distance data structure of the expression profiles of the plurality of cells. The distance data structure can comprise a distance matrix of the expression profiles of the plurality of cells. Each diagonal element of the distance matrix can have a value of zero. To cluster the expression profiles of the plurality of cells to generate the plurality of clusters of expression profiles based on the distances between the expression profiles of the plurality of cells in (b), the hardware processor can be programmed to: cluster the expression profiles of the plurality of cells to generate the plurality of clusters of expression profiles based on the distance matrix. The distances between the expression profiles of the plurality of cells can be pairwise correlation distances between the expression profiles of the plurality of cells.

In some embodiments, the hardware processor can be programmed to, prior to determining the distance data structure in (i), log-transform the target counts data structure into a log-transformed target counts data structure. To determine the distance data structure of elements of the target counts data structure, the hardware processor can be programmed to: determine the distance data structure of the log-transformed target counts data structure. To cluster the expression profiles of the plurality of cells to generate the plurality of clusters of expression profiles based on the distances between expression profiles of the plurality of cells in (b), the hardware processor can be programmed to: cluster the expression profiles of the plurality of cells based on the log-transformed target counts data structure and the distance data structure to generate the plurality of clusters. To log-transform the target counts data structure into the log-transformed target counts data structure, the hardware processor can be programmed to: increase the value of each element of the target counts data structure by an increment. The increment can be one.

In some embodiments, to cluster the expression profiles of the plurality of cells based on distances between the expression profiles of the plurality of cells in (b), the hardware processor can be programmed to: assign each expression profile of the plurality of cells to a different leaf cluster in the plurality of clusters; and iteratively combine a first cluster and a second cluster of the plurality of clusters to generate a parent cluster of the first cluster and the second cluster if the second cluster is the closest cluster of the plurality of cluster to the first cluster. The distance between the first cluster and the second cluster can be the maximum distance between any expression profile represented by the first cluster and any expression profile represented by the second cluster In some embodiments, an intra-cluster correlation of the first cluster and an intra-cluster correlation of the second cluster are higher than an inter-cluster correlation of the first cluster and the second cluster. A measure or an indication of an intra-cluster correlation of the first cluster and an intra-cluster correlation of the second cluster can be higher than an inter-cluster correlation of the first cluster and the second cluster. The measure of the intra-cluster correlation of the first cluster and the intra-cluster correlation of the second cluster can be based on at least one of: an intra-cluster maximum correlation of the first cluster and the second cluster, an intra-cluster average correlation of the first cluster and the second cluster, an intra-cluster median correlation of the first cluster and the second cluster, an intra-cluster minimum correlation of the first cluster and the second cluster, and any combinations thereof. The intra-cluster correlation of the first cluster can be based on at least one of: an intra-cluster maximum correlation of the first cluster, an intra-cluster average correlation of the first cluster, an intra-cluster median correlation of the first cluster, an intra-cluster minimum correlation of the first cluster, and any combinations thereof. The intra-cluster correlation of the second cluster can be based on at least one of: an intra-cluster maximum correlation of the second cluster, an intra-cluster average correlation of the second cluster, an intra-cluster median correlation of the second cluster, an intra-cluster minimum correlation of the second cluster, and any combinations thereof. The inter-cluster correlation of the first cluster and the second cluster can be based on at least one of: an inter-cluster maximum correlation of the first cluster and the second cluster, an inter-cluster average correlation of the first cluster and the second cluster, an inter-cluster median correlation of the first cluster and the second cluster, an inter-cluster minimum correlation of the first cluster and the second cluster, and any combinations thereof.

In some embodiments, the hardware processor can be programmed to, at each cluster when traversing the plurality of clusters of the dendrogram: if the associations are valid, continue traversing from the cluster to the left child cluster and the right child cluster of the cluster; and if the associations are invalid, discontinue traversing from the cluster to the left child cluster and the right child cluster of the cluster. To determine whether the associations of the cluster with the child clusters of the cluster are valid or invalid, the hardware processor can be programmed to: determine the associations to be valid if the distance between the left child cluster and the right child cluster is above an association threshold, and otherwise invalid. The distance between the left child cluster and the right child cluster can be determined based on a statistical test performed on each target of the plurality of targets between expression profiles represented by the left child cluster and the right child cluster. The statistical test can comprise a Welch's t-test. The distance between the left child cluster and the right child cluster can be determined based on the maximum p-value of the statistical test performed on the each target of the plurality of targets between expression profile represented by the left child cluster and each expression profile represented by the right child cluster.

In some embodiments, the hardware processor can be programmed to, at each cluster when traversing the plurality of clusters of the dendrogram: (3) add the cluster to the merging cluster set if the cluster represents an expression profile of a single cell. The hardware processor can be programmed to: at each cluster when traversing the plurality of clusters of the dendrogram: assigning a cluster label to the cluster. If the cluster represents an expression profile of a single cell, the cluster label of the cluster comprises a single cell designation, otherwise, if the cluster is the left child cluster of the parent cluster, the cluster label of the cluster comprises the cluster label of the parent cluster and a left designation, and otherwise, the cluster label of the cluster comprises the cluster label of the parent cluster and a right designation.

In some embodiments, for each cluster in the merging cluster set, identifying the targets for distinguishing the cell types based on the expression profiles of the plurality of targets of the cells represented by the cluster, the hardware processor can be programmed to: determine a difference, between expression profiles represented by the cluster and expression profiles represented by another cluster in the merging cluster set, in numbers of molecular labels with distinct sequences associated with the targets for distinguishing the cell types is greater than a significance threshold. The hardware processor can be programmed to comprising, prior to merging the first cluster with the second cluster to generate the merged cluster in (d): merge each third cluster in the merging cluster set representing an expression profile of a single cell with a fourth cluster in the merging cluster set if a distance between the third cluster and the fourth cluster is within a cluster distance threshold.

In some embodiments, the hardware processor can be programmed to: classify the plurality of cells based on the clusters in the merging cluster set that represent expression profiles of the cells. The hardware processor can be programmed to: design a whole transcriptome assay based on the targets for distinguishing cell types identified. The hardware processor can be programmed to: design a targeted transcriptome assay based on the targets for distinguishing cell types identified.

BRIEF DESCRIPTION OF THE DRAWINGS

FIGS. 14A-14D are non-limiting exemplary plots of expression profiles in a two dimensional space showing how the second cycle of merges shown in FIG. 13 was decided.

FIGS. 17A-17G are non-limiting exemplary plots visualizing the distances between clusters.

FIGS. 18 and 18A-18E show a non-limiting exemplary dendrogram.

FIGS. 21A-21J are non-limiting exemplary plots showing the results of the first split.

FIGS. 23 and 23A-23E show a non-limiting exemplary dendrogram showing expression profiles classified into two clusters.

DETAILED DESCRIPTION

Figure 1:
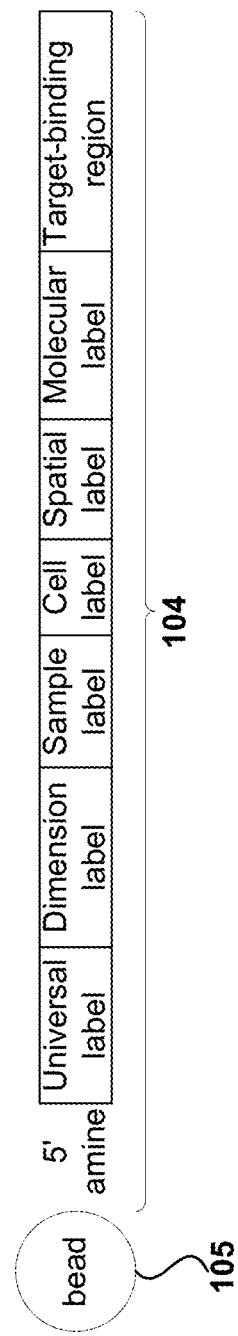
FIG. 1 illustrates a non-limiting exemplary barcode (e.g., a stochastic barcode).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids or targets, for example messenger ribonucleotide acid (mRNA) molecules, is clinically important for determining, for example, the genes that are expressed in a cell at different stages of development or under different environmental conditions. However, it can be very challenging to determine the absolute number of nucleic acid molecules (e.g., mRNA molecules), especially when the number of molecules is very small. One method to determine the absolute number of molecules in a sample is digital polymerase chain reaction (PCR). Barcodes (e.g., stochastic barcodes) with unique molecular labels (MLs, also referred to as molecular indexes (MIs)) can be used to count the numbers of molecules. Barcodes with molecular labels that are unique for each cell label can be used to count the numbers of molecules in each cell. Non-limiting exemplary assays for barcoding (e.g., stochastic barcoding) include the Precise™ assay (Cellular Research, Inc. (Palo Alto, Calif.)), the Resolve™ assay (Cellular Research, Inc. (Palo Alto, Calif.)), or the Rhapsody™ assay (Cellular Research, Inc. (Palo Alto, Calif.)).

The Rhapsody™ assay can utilize a non-depleting pool of barcodes (e.g., stochastic barcodes) with large number, for example 6561 to 65536, unique molecular labels on poly(T) oligonucleotides to hybridize to all poly(A)-mRNAs in a sample during the RT step. In addition to molecular labels, cell labels of barcodes can be used to identify each single cell in each well of a microwell plate. A barcode (e.g., a stochastic barcode) can comprise a universal PCR priming site. During RT, target gene molecules react randomly with barcodes. Each target molecule can hybridize to a barcode resulting to generate barcoded complementary ribonucleotide acid (cDNA) molecules (e.g., stochastically barcoded cDNA molecules). After labeling, barcoded cDNA molecules from microwells of a microwell plate can be pooled into a single tube for PCR amplification and sequencing. Raw sequencing data can be analyzed to produce the numbers of barcodes (e.g., stochastic barcodes) with unique molecular labels.

Disclosed herein are methods for identifying targets to distinguish cell types. In some embodiments, the method comprises: (a) receiving a target counts data structure, wherein the target counts data structure comprises expression profiles of a plurality of cells, and wherein the expression profiles of the plurality of cells comprises a number of each target of a plurality of targets for each cell of the plurality of cells; (b) hierarchically clustering expression profiles of the plurality of cells based on the target counts data structure and distances between the expression profiles of the plurality of cells to generate a dendrogram representing the expression profiles of plurality of cells, wherein the dendrogram comprises a plurality of nodes, wherein the plurality of nodes comprise a root node, a plurality of leaf nodes, and a plurality of non-root, non-leaf nodes, wherein each leaf node of the plurality of leaf nodes represents an expression profile of a different cell of the plurality of cells, and wherein the root node represents expression profiles of the plurality of cells; (c) while traversing through each node of the plurality of nodes of the dendrogram from the root node of the dendrogram to the plurality of leaf nodes of the dendrogram: (1) determining whether a splitting of the node into child nodes of the node is valid or invalid (e.g., the differences between the child nodes are not significant); and (2) if the splitting of the node into the child nodes of the node is invalid, adding the node to a merging cluster set; (d) iteratively, for each first node in the merging cluster set, if a distance between the first node in the merging cluster set and a second node in the merging cluster set that is closest to the first node is within a merging distance threshold, merging the first node with the second node to generate a merged node comprising expression profiles represented by the first node and the second node; and (e) for each node in the merging cluster set, identifying targets for distinguishing cell types based on expression profiles of the plurality of targets of cells represented by the node.

Disclosed herein systems for identifying targets to distinguish cell types. In some embodiments, the system comprises: a hardware processor; and non-transitory memory having instructions stored thereon, which when executed by the hardware processor cause the processor to perform any of the methods disclosed herein. Disclosed herein are computer readable media for identifying targets for distinguishing cell types. In some embodiments, the computer readable medium comprises code for performing any of the methods disclosed herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used here, the term, "spatial label" can refer to a label which can be associated with a position in space.

As used herein, the term "stochastic barcode" can refer to a polynucleotide sequence comprising labels. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "gene-specific stochastic barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thrmosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Disclosed herein are systems and methods for identifying targets for distinguishing cell types. In some embodiments, the method comprises: (a) receiving a target counts data structure (e.g., a target counts matrix) comprising expression profiles; (b) hierarchically clustering the expression profiles of the plurality of cells to generate a dendrogram representing the expression profiles; (c) while traversing through each node of the dendrogram from the root node of the dendrogram to the leaf nodes of the dendrogram: (1) determining whether a splitting of the node into child nodes of the node is valid or invalid (e.g., the differences between the child nodes are not significant); and (2) if the splitting of the node into the child nodes of the node is invalid, adding the node to a merging cluster set; (d) iteratively, for each first node in the merging cluster set, if a distance between the first node in the merging cluster set and a second node in the merging cluster set that is closest to the first node is within a merging distance threshold, merging the first node with the second node to generate a merged node comprising expression profiles represented by the first node and the second node; and (e) for each node in the merging cluster set, identifying targets for distinguishing cell types based on expression profiles of the plurality of targets of cells represented by the node.

Barcodes

Barcoding, such as stochastic barcoding, has been described in, for example, US20150299784, WO2015031691, and Fu et al, Proc Natl Acad Sci U.S.A. 2011 May 31; 108(22):9026-31 and Fan et al., *Science* (2015) 347(6222):1258367; the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be, for example, an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequence (e.g., a molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20 or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was stochastically barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, or 10 or more times. The dimension label can be reversibly activatable, for example, at least 1, 2, 3, 4, 5, 6, 7, 8, 9, or 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., bead), but different for different solid supports (e.g., beads). In some embodiments, at least 60%, 70%, 80%, 85%, 90%, 95%, 97%, 99% or 100% of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space.

The spatial label can be identical for all barcodes attached to a given solid support (e.g., bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or at most, $10^2$, $10^3$, $10^4$, $10^5$, $10^6$, $10^7$, $10^8$, or $10^9$, unique barcode sequences. The unique molecular label sequences can be attached to a given solid support (e.g., bead).

A barcode can be, or be about, 1, 2, 3, 4, 5, 10, 15, 20, 25, 30, 35, 40, 45, 50, or a number or a range between any two of these values, nucleotides in length. A barcode can be at least, or at most, 1, 2, 3, 4, 5, 10, 15, 20, 25, 30, 35, 40, 45, 50, 100, 200, or 300 nucleotides in length.

Molecular Labels

A stochastic barcode can comprise one or more molecular labels. Molecular labels can include barcode sequences. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. Stochastic barcodes with the unique molecular label sequences can be attached to a given solid support (e.g., bead).

For stochastic barcoding using a plurality of stochastic barcodes, the ratio of the number of different molecular label sequences and the number of occurrence of any of the targets can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A barcode can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, ora number or a range between any two of these nucleotides in length. A universal adaptor primer can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequence, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10X Genomics (San Francisco, Calif.). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combinations thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of crosslink bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
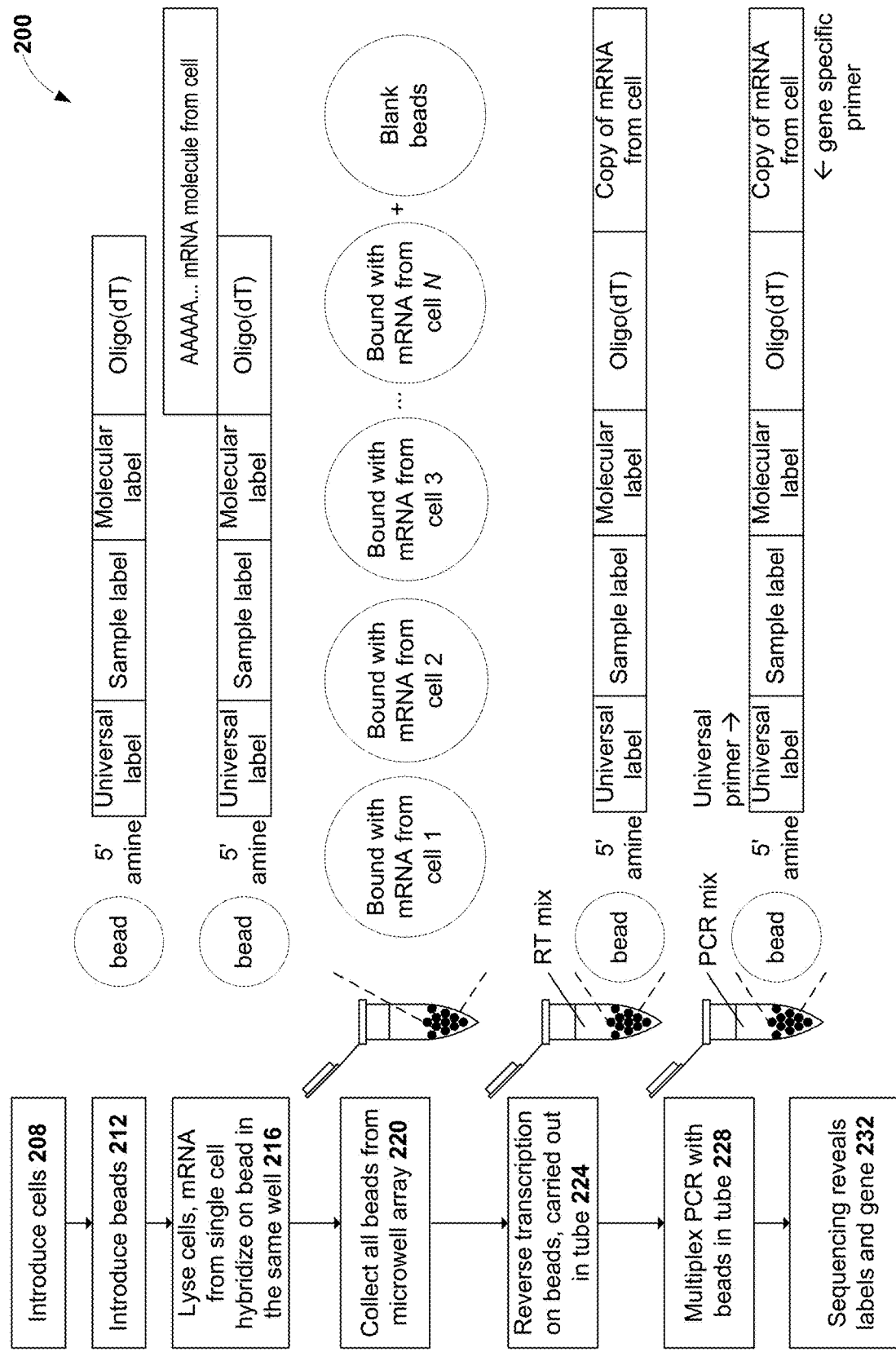
FIG. 2 shows a non-limiting exemplary workflow of barcoding and digital counting (e.g., stochastic barcoding and digital counting).

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode sequences of different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, stochastically barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized" are used interchangeably, and can refer to covalent or non-covalent means for attaching barcodes to a solid support. Any of a variety of different solid supports can be used as solid supports for attaching pre-synthesized barcodes or for in situ solid-phase synthesis of barcodes.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example beads). Each of the particles can comprise a plurality of oligonucleotides (e.g., barcodes). Each of the plurality of oligonucleotides can comprise a barcode sequence (e.g., a molecular label), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell label sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different barcode sequences (e.g., molecular labels). In some embodiments, the number of barcode sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameters of beads can be, or be about, 0.1, 0.5, 1, 2, 3, 4, 5, 6, 7, 8, 9, 10, 20, 30, 40, 50 micrometer, or a number or a range between any two of these values.

The diameters of the bead can be related to the diameter of the wells of the substrate. In some embodiments, the diameters of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameters of the bead can be at least, or at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameters of the beads can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameters of the beads can be at least, or at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be a biological molecule. For example a solid support can be a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose barcodes (e.g., stochastic barcodes) of the disclosure to targets. For example, a biological molecule can comprise barcodes that are inaccessible due to folding of the biological molecule. Upon modification of the biological molecule (e.g., acetylation), the biological molecule can change conformation to expose the barcodes. The timing of the modification can provide another time dimension to the method of barcoding of the disclosure.

In some embodiments, the biological molecule comprising barcode reagents of the disclosure can be located in the cytoplasm of a cell. Upon activation, the biological molecule can move to the nucleus, whereupon barcoding can take place. In this way, modification of the biological molecule can encode additional space-time information for the targets identified by the barcodes.

Substrates and Microwell Array

As used herein, a substrate can refer to a type of solid support. A substrate can refer to a solid support that can comprise barcodes and stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead). A microwell can comprise combinatorial barcode reagents of the disclosure.

Methods of Barcoding

The disclosure provides for methods for estimating the number of distinct targets at distinct locations in a physical sample (e.g., tissue, organ, tumor, cell). The methods can comprise placing the barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. In some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be crosslinked to the barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7% or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e. a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cell label and/or barcode sequence (e.g., molecular label). The amplification reactions can comprise amplifying at least a portion of a sample tag, a cell label, a spatial label, a barcode (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled-amplicon (e.g., a stochastically labeled-amplicon). The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction.

The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded fragments. The barcodes sequences of different barcodes (e.g., the molecular labels of different stochastic barcodes) can be different from one another. Generating an indexed library of the barcoded targets (e.g., stochastically barcoded targets) includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, barcode sequences (e.g., molecular labels), and sequences of nucleotide fragments of the one or more copies of the targets, for example at block 232 of FIG. 2.

Figure 3:
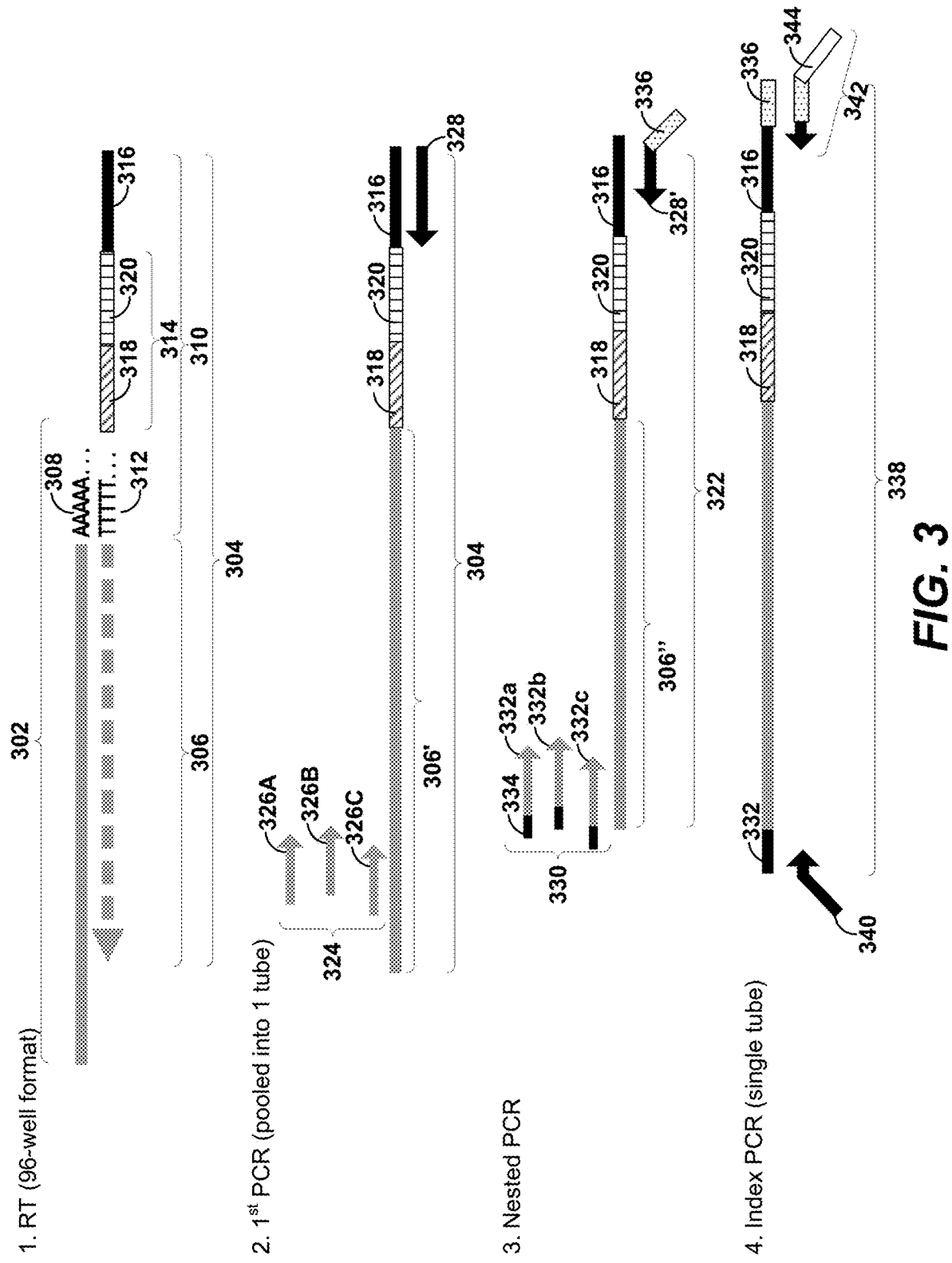
FIG. 3 is a schematic illustration showing a non-limiting exemplary process for generating an indexed library of the barcoded targets (e.g., stochastically barcoded targets) from a plurality of targets.

FIG. 3 is a schematic illustration showing a non-limiting exemplary process of generating an indexed library of the barcoded targets (e.g., stochastically barcoded targets), for example mRNAs. As shown in step 1, the reverse transcription process can encode each mRNA molecule with a unique barcode sequence (e.g., molecular label), a cell label, and a universal PCR site. For example, RNA molecules 302 can be reverse transcribed to produce labeled cDNA molecules 304, including a cDNA region 306, by the hybridization (e.g., stochastic hybridization) of a set of barcodes (e.g., stochastic barcodes) 310) to the poly(A) tail region 308 of the RNA molecules 302. Each of the barcodes 310 can comprise a target-binding region, for example a poly(dT) region 312, a barcode sequence or a molecular label 314, and a universal PCR region 316.

In some embodiments, the cell label can include 3 to 20 nucleotides. In some embodiments, the barcode sequence (e.g., molecular label) can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. For example, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Clustering Expression Profiles Using a Dendrogram

Disclosed herein are methods for identifying targets to distinguish cell types. In some embodiments, the method comprises: (a) receiving a target counts data structure, wherein the target counts data structure comprises expression profiles of a plurality of cells, and wherein the expression profiles of the plurality of cells comprises a number of each target of a plurality of targets for each cell of the plurality of cells; (b) hierarchically clustering expression profiles of the plurality of cells based on the target counts data structure and distances between the expression profiles of the plurality of cells to generate a dendrogram representing the expression profiles of plurality of cells, wherein the dendrogram comprises a plurality of nodes, wherein the plurality of nodes comprise a root node, a plurality of leaf nodes, and a plurality of non-root, non-leaf nodes, wherein each leaf node of the plurality of leaf nodes represents an expression profile of a different cell of the plurality of cells, and wherein the root node represents expression profiles of the plurality of cells; (c) while traversing through each node of the plurality of nodes of the dendrogram from the root node of the dendrogram to the plurality of leaf nodes of the dendrogram: (1) determining whether a splitting of the node into child nodes of the node is valid or invalid (e.g., the differences between the child nodes are not significant); and (2) if the splitting of the node into the child nodes of the node is invalid, adding the node to a merging cluster set; (d) iteratively, for each first node in the merging cluster set, if a distance between the first node in the merging cluster set and a second node in the merging cluster set that is closest to the first node is within a merging distance threshold, merging the first node with the second node to generate a merged node comprising expression profiles represented by the first node and the second node; and (e) for each node in the merging cluster set, identifying targets for distinguishing cell types based on expression profiles of the plurality of targets of cells represented by the node.

Figure 4:
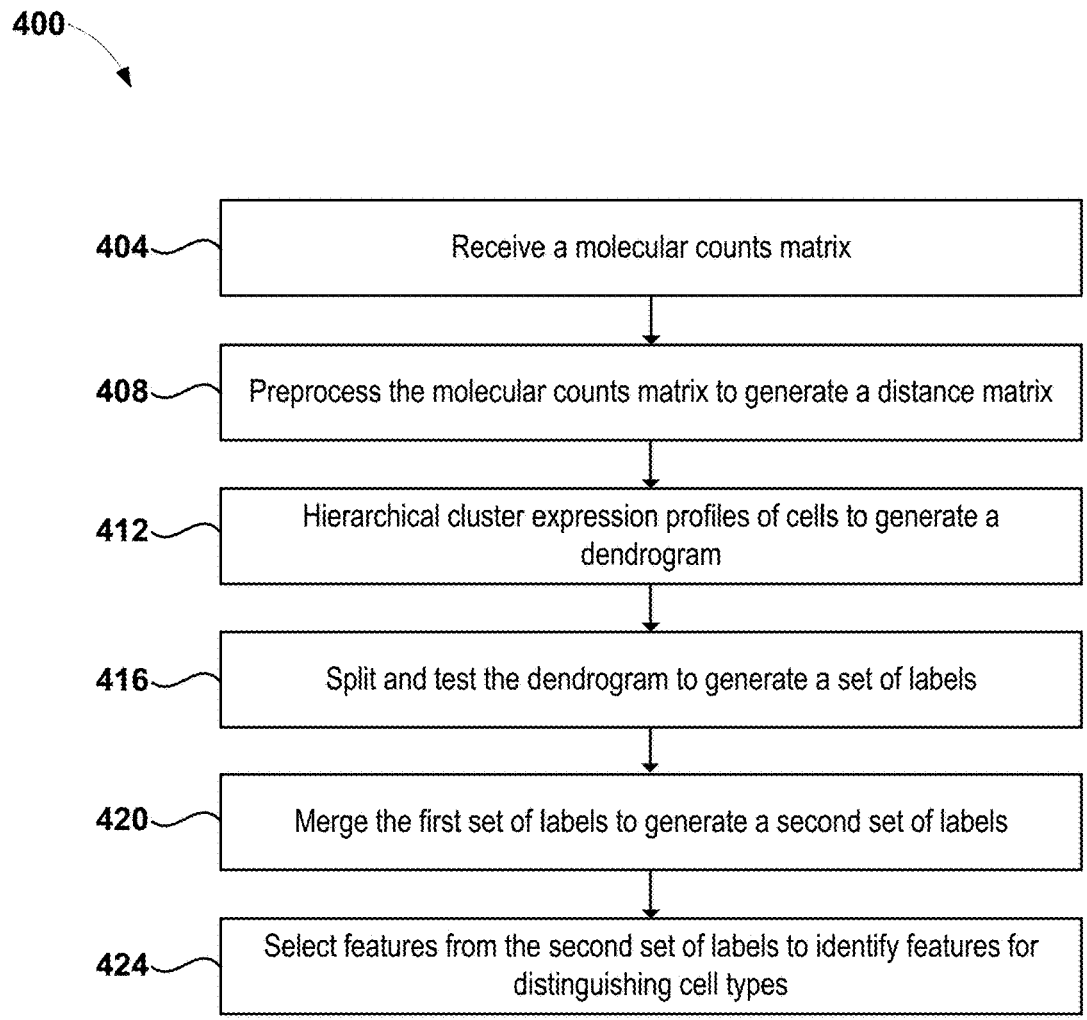
FIG. 4 is a flowchart showing a non-limiting exemplary method of identifying targets for distinguishing cell types by clustering expression profiles of cells using a dendrogram.

FIG. 4 is a flowchart showing a non-limiting exemplary method 400 of identifying targets for distinguishing cell types. The method 400 maps a molecular counts data structure (e.g., a molecular counts matrix) to a set of cluster labels and a set of important genes. In some embodiments, the input can be a N-by-M matrix of molecular counts or an array where the i,jth entry describes the number of molecules for gene j that were observed using the reads from cell i. The algorithm can generate two outputs. The first output can be a set of N labels, one for each cell (cells of the same label can be inferred as to being "similar"). The second output can be a set of genes that can be used for distinguishing the clusters from one another.

Figure 5:
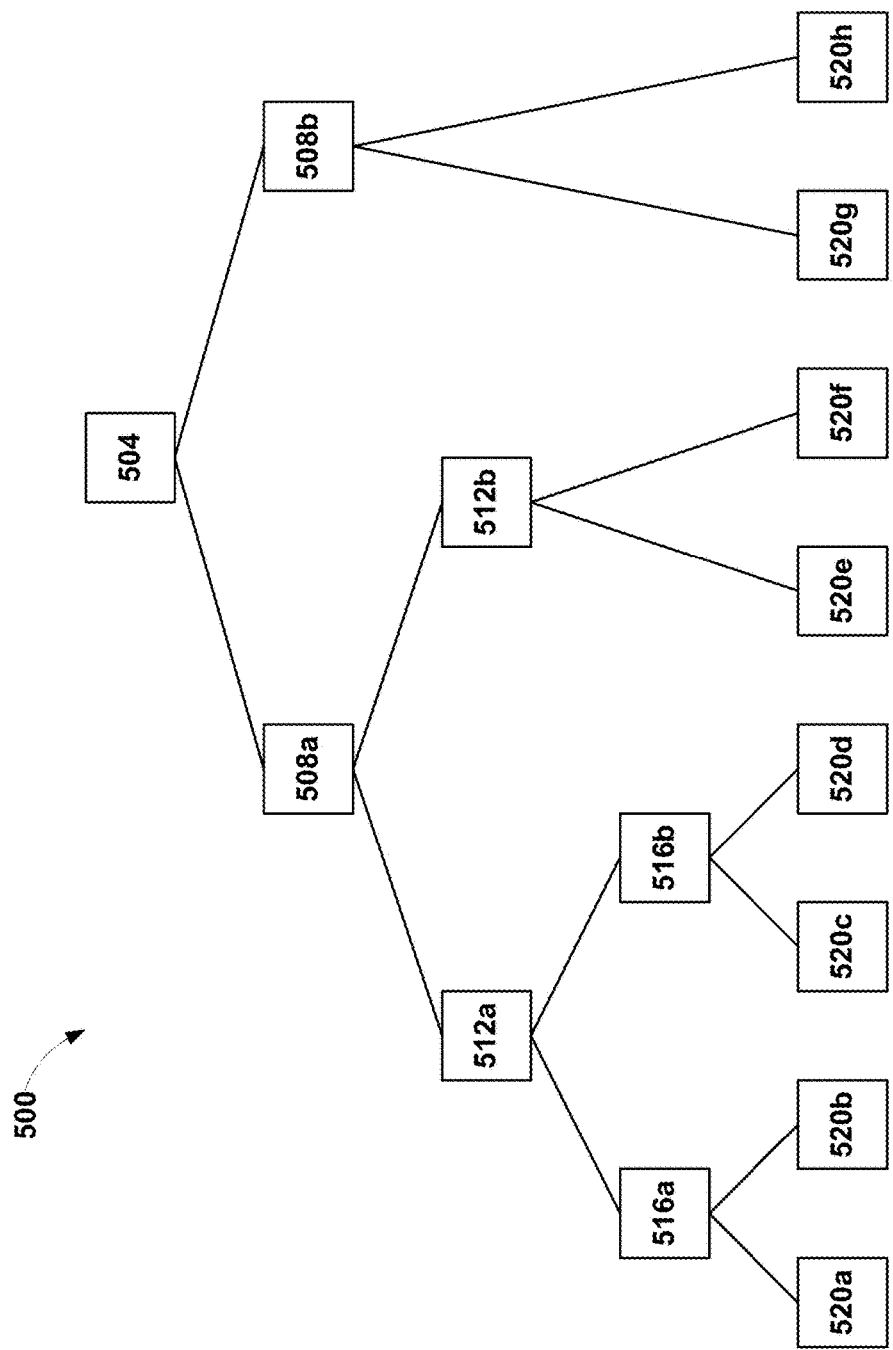
FIG. 5 is a schematic illustration of an exemplary dendrogram.

The method 400 generates the two outputs using a dendrogram splitting, testing, and merging approach. After preprocessing the data and generating a distance data structure (e.g., a distance matrix) D, the algorithm can hierarchically cluster D to produce a dendrogram. The algorithm can include two phases. During the splitting and testing phase, the method 400 starts from the top of the dendrogram (e.g., the root node 504 of the tree or dendrogram 500 in FIG. 5). The dendrogram 500 includes the root node 504, a plurality of leaf nodes 520a-520h, and a plurality of non-root, non-leaf nodes 508a-508b, 512a-512b, and 516a-516b. At each node of the dendrogram (except for leaf nodes, such as leaf nodes 520a-520h), the tree is split into two subtrees (e.g., the root node 504 is split into two subtrees 508a, 508b). The split corresponds to a cluster (e.g., containing expression profiles of two or more cells) being split into two candidate subclusters (e.g., each containing the expression profile of at least one cell). The quality of the split can be scored. If the subclusters are deemed to be sufficiently different, the algorithm continues to run on each subtree. If not, the algorithm terminates for this portion of the dendrogram. This phase produces a set of labels for the dataset. During the merging phase, the method 400 uses the labels generated during the splitting and testing phase to determine if any of these clusters should be combined to form one cluster. In some embodiments, the splitting and testing phase tends to produce small clusters of a few samples each. The merging phase can "clean up" the smaller clusters by merging them with larger clusters.

At block 404, the method 400 can include receiving a molecular counts data structure (e.g., a molecular counts matrix). The matrix can comprise only whole, nonnegative entries and tends to be large and sparse. In some embodiments, the input can be a N-by-M matrix of molecular counts or an array where the i,jth entry describes the number of molecules for gene j that were observed using the reads from cell i.

At block 408, the method 400 can include preprocessing the molecular counts data structure to generate a distance data structure (e.g., a distance matrix). In some embodiments, the input data structure is log-transformed. The value 1 is added to each entry before a natural log is taken. Correlation distance can be used to describe the pairwise dissimilarity d between each pair of cells. For cells $c_i$ and $c_j$, the correlation distance between the two cells can be determined using Eq. [1].

$$d(c_i, c_j) = 1 - \frac{(c_i - \bar{c}_i) \cdot (c_j - \bar{c}_j)}{\|c_i - \bar{c}_i\|_2 \|c_j - \bar{c}_j\|_2}, \quad \text{Eq. [1]}$$

where $\bar{c}_i$ denotes the mean of all the elements of $c_i$. The output of the preprocessing step can be a square, symmetric matrix D of distances with 0's along the diagonal.

At block 412, the method 400 can include hierarchical clustering expression profiles of cells to generate a dendrogram. Hierarchically clustering the expression profiles of cells to generate the dendrogram can comprise iteratively merging the two closest clusters of the dendrogram. All clusters can be initiated as individual points with pairwise distances described as above. Computing the distance D between clusters was done using complete linkage. For clusters A and B, the distance between the two clusters can be determined using Eq. [2]:

$$D(A, B) = \max_{a \in A, b \in B} d(a, b). \quad \text{Eq. [2]}$$

A full dendrogram can be obtained at this block. In some embodiments, an intra-cluster correlation of cluster A and an intra-cluster correlation of cluster B are higher than an inter-cluster correlation of the cluster A and the cluster B. A measure or an indication of an intra-cluster correlation of the cluster A and an intra-cluster correlation of the cluster B is higher than an inter-cluster correlation of the cluster A and the cluster B. The measure of the intra-cluster correlation of the cluster A and the intra-cluster correlation of the cluster B can be based on at least one of: an intra-cluster maximum correlation of the cluster A and the cluster B, an intra-cluster average correlation of the cluster A and the cluster B, an intra-cluster median correlation of the cluster A and the cluster B, an intra-cluster minimum correlation of the cluster A and the cluster B, and any combinations thereof. The intra-cluster correlation of the cluster A can be based on at least one of: an intra-cluster maximum correlation of the cluster A, an intra-cluster average correlation of the cluster A, an intra-cluster median correlation of the cluster A, an intra-cluster minimum correlation of the cluster A, and any combinations thereof. The intra-cluster correlation of the cluster B can be based on at least one of: an intra-cluster maximum correlation of the cluster B, an intra-cluster average correlation of the cluster B, an intra-cluster median correlation of the cluster B, an intra-cluster minimum correlation of the cluster B, and any combinations thereof. The inter-cluster correlation of the cluster A and the cluster B can be based on at least one of: an inter-cluster maximum correlation of the cluster A and the cluster B, an inter-cluster average correlation of the cluster A and the cluster B, an inter-cluster median correlation of the cluster A and the cluster B, an inter-cluster minimum correlation of the cluster A and the cluster B, and any combinations thereof. For example, the intra-cluster median correlation of the two sub-clusters can be higher than the inter-cluster median correlation.

At block 416, the method 400 can include splitting and testing the dendrogram to generate a set of labels. Splitting and testing can be initiated at the top of the dendrogram. Given a dendrogram subtree $T_0$, the tree can be split into exactly two subtrees $T_L$ and $T_R$. A statistical test can be performed to determine whether the cells in the left subtree $T_L$ are sufficiently different from the cells in the right subtree $T_R$. In some embodiments, the statistical test involves performing a Welch's t-test on each gene for the two populations. t-statistics of infinity can occur if the variance is estimated to be 0 in both populations; these cases can be ignored. If the minimum p-value amongst all tests is lower than a certain threshold (conservatively corrected for false detection rate), then the split may be deemed valid, and the algorithm is performed again on the two subtrees. If the minimum p-value is not below the threshold, the method 400 terminates for subtree $T_0$. If $T_L$ contains exactly 1 sample (i.e., $T_L$ is a singleton), $T_L$ can be ignored and the algorithm repeats the procedure with $T_R$. If $T_R$ contains exactly 1 sample, $T_R$ can ignored and the algorithm repeats the procedure with $T_L$. If both $T_L$ and $T_R$ contain exactly 1 sample each, the algorithm terminates for subtree $T_0$.

At block 416, the method 400 can include determining cluster labels as follows. At first, all subtrees can be labeled 'r'. Each time a split happens and is not rejected due to p-value issues, all labels of cells in $T_L$ are appended with 'L' and all labels of cells in $T_R$ can be appended with 'R'. This means that when skipping over singletons, labels are still affected. The singleton automatically gets a unique label not shared with any other data point.

At block 416, the method 400 can include determining the cohesiveness of each final cluster. If all samples within a final cluster are far away from each other (i.e., no pairwise distance within the cluster is in the bottom, for example, 50 percentile of all distances), then the cluster can be disbanded. Each sample can then marked as a singleton.

At block 420, the method 400 can include merging the set of labels generated at block 416 to generate another set of labels. In some embodiments, merging can be a two-stage process. At the first stage, each singleton can be placed in the same cluster as its nearest neighbor determined using the distance data structure (e.g., distance matrix) from the preprocessing block 408. If a singleton's distance to its nearest neighbor lies within the top 10% of distances (i.e., it's far from all other cells), the singleton can be marked as an outlier and remains in its own cluster. This first step ensures that all clusters contain at least two non-outlier members. At the second step, after removing the outliers, the pairwise distances between clusters are computed using several statistical tests, resulting in a pairwise cluster distance matrix $D_c$. The distance between two clusters is estimated as the negative log of the smallest p-value obtained over independent Welch's t-tests over all genes. Starting with the overall smallest distance, the two corresponding clusters are merged. The distances of the new cluster to all existing clusters are computed and the process is repeated until all pairwise distances are above a certain distance. The package also gives a community-detection-based approach to merging by running the Louvain algorithm on $D_c$.

At block 424, the method 400 can include selecting features from the set of labels determined at block 420 to identify features for distinguishing cell types. In some embodiments, the method 400 can perform two types of feature selection using the labels generated from the merging block 420. For the first type of feature selection, during the splitting and testing block, each time a split is kept, the K genes with the K smallest p-values are saved. More genes can be kept from splits closer to the top of the dendrogram. Ultimately, a list of unique genes from the union of all the splits is outputted. For the second type of feature selection, for each cluster, several one-vs-rest tests are done using only the genes that have higher means in the cluster of interest. A table of important genes for each cluster can be outputted along with some extra information about each gene (e.g. p-value, fold change, mean expression level within the cluster).

The method 400 can include performing exploratory analysis. In some embodiments, the method 400 can utilize several functions for visualizing certain steps in the splitting and merging stages can be used. For example, these functions illustrate the cells involved in the split (or merge), the cells the end up in each subtree (or the combined cluster), and the genes that dictated this split (or merge). As another example, the method 400 can perform pairwise comparisons amongst all clusters (e.g., to determine which genes distinguish each pair of clusters) and functions for drawing the dendrogram. The method 400 can be based on the distributions of pairwise distances within clusters. In some embodiments, the method 400 can include performing parameter sweeps are also provided.

Clustering Expression Profiles

Disclosed herein are methods for identifying targets to distinguish cell types. In some embodiments, the method comprises: (a) receiving expression profiles of a plurality of cells, wherein the expression profiles comprise a number of each target of a plurality of targets for each cell of the plurality of cells; (b) clustering the expression profiles of the plurality of cells to generate a plurality of clusters of expression profiles based on the distances between the expression profiles of the plurality of cells, wherein each cluster has one or more associations with one or both of (1) a parent cluster and (2) two or more child clusters, wherein the parent cluster represents expression profiles of one or more cells of the plurality of cells represented by the cluster, and wherein the cluster represents expression profiles represented by the two or more child clusters; (c) for each cluster with two or more child clusters, if associations between the cluster with the two or more child clusters are invalid (e.g., the differences between the two or more child clusters are not significant), adding the cluster to a merging cluster set; (d) iteratively, for each first cluster in the merging cluster set, if a distance between the first cluster in the merging cluster set and a second cluster in the merging cluster set that is closest to the first cluster is within a merging distance threshold, merging the first cluster and the second cluster to generate a merged cluster, wherein the merged cluster comprises expression profiles of the first cluster and the second cluster; and (e) for each cluster in the merging cluster set, identifying targets for distinguishing cell types based on expression profiles of the plurality of targets of cells represented by the cluster.

Figure 6:
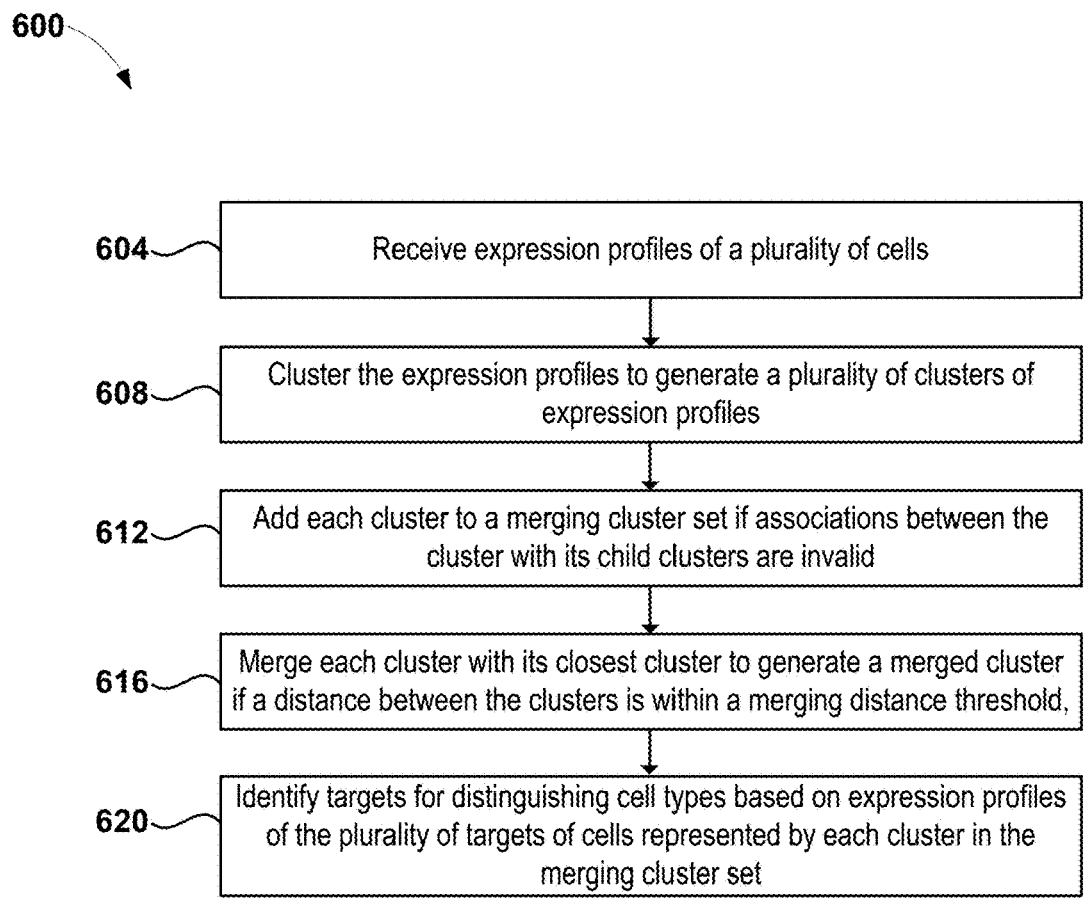
FIG. 6 is a flowchart showing a non-limiting exemplary method of identifying targets for distinguishing cell types by clustering expression profiles of cells.

FIG. 6 is a flowchart showing a non-limiting exemplary method of identifying targets to distinguish cell types by clustering expression profiles of cells. At block 604, the method 600 receives expression profiles of a plurality of cells. Each expression profile can comprises a number of each target of a plurality of targets for a different cell of the plurality of cells. In some embodiments, receiving expression profiles of the plurality of cells comprises receiving a target counts data structure (e.g., a target counts matrix). Each row of the target counts matrix can comprise an expression profile of a cell of a plurality of cells.

The number of expression profiles received can be different in different implementations. In some embodiments, the number of expression profiles received can be, or be about, 10, 20, 30, 40, 50, 60, 70, 80, 90 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of expression profiles received can be at least, or at most, 10, 20, 30, 40, 50, 60, 70, 80, 90 100, 200, 300, 400, 500, 600, 700, 800, 900, 1000, 2000, 3000, 4000, 5000, 6000, 7000, 8000, 9000, or 10000.

In some embodiments, the method 600 comprises: prior to receiving the expression profiles of the plurality of cells at block 604: stochastically barcoding the plurality of targets in the plurality of cells using a plurality of stochastic barcodes to create a plurality of stochastically barcoded targets, wherein each of the plurality of stochastic barcodes comprises a cell label and a molecular label, wherein stochastically barcoded targets created from targets of different cells have different cell labels, and wherein stochastically barcoded targets created from targets of one cell of the plurality of cells have different molecular labels; obtaining sequencing data of the plurality of stochastically barcoded targets; and for each of the plurality of cells: (1) counting the number of molecular labels with distinct sequences associated with each target of the plurality of targets in the sequencing data for the cell; and (2) estimating the number of each target of the plurality of targets for the cell based on the number of molecular labels with distinct sequences associated with the target in the sequencing data counted in (1). In some embodiments, the expression profile of the cell of the plurality of cells comprises the number of each target of the plurality of targets for the cell estimated in (2).

At block 608, the method 600 can include clustering the expression profiles of the plurality of cells to generate a plurality of clusters of expression profiles. The method 600 can generate the clusters of expression profiles based on the distances between the expression profiles of the plurality of cells. The number of expression profiles represented by each cluster can be different in different implementations. In some embodiments, the number of expression profiles represented by each cluster can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of expression profiles represented by each cluster can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000. In some embodiments, the expression profiles represented by each cluster can be, or be about, 1%, 2%, 3%, 4%, 5%, 6%, 7%, 8%, 9%, 10%, 20%, 30%, 40%, 50%, 60%, 70%, 80%, 90%, 100%, or a number or a range between any two of these values, of the number of expression profiles received at block 604. In some embodiments, the expression profiles represented by each cluster can be at least, or at most, 1%, 2%, 3%, 4%, 5%, 6%, 7%, 8%, 9%, 10%, 20%, 30%, 40%, 50%, 60%, 70%, 80%, 90%, or 100%, of the number of expression profiles received at block 604.

Each cluster can have an association with one or both of (1) a parent cluster and (2) two or more child clusters (such as 3, 4, 5, 6, 7, 8, 9, 10, or more child clusters). The parent cluster represents expression profiles of one or more cells of the plurality of cells represented by the cluster. The cluster represents expression profiles represented by its two or more child clusters.

In some embodiments, the expression profiles can be clustered as described with reference to FIG. 4, such as block 412 of FIG. 4. For example, the method 600 can include hierarchically clustering the expression profiles of the plurality of cells to generate a dendrogram representing the expression profiles of the plurality of cells based on the distances between the expression profiles of the plurality of cells. The dendrogram can comprise the plurality of clusters. The plurality of clusters can comprise a root cluster, a plurality of leaf clusters, and a plurality of non-root, non-leaf clusters. The number of leaf clusters can be, for example, the same as the number of expression profiles n. The number of non-root, non-leaf clusters can be, for example, n−2.

Each of the plurality of leaf clusters and the plurality of non-root, non-leaf clusters can have an association with a parent cluster. Each of the root cluster and the plurality of non-root, non-leaf clusters can have associations with a left child cluster and a right child cluster and represents expression profiles represented by the left child cluster and the right child cluster of the cluster. The root cluster can represent the expression profiles of the plurality of cells. In some implementations, a leaf cluster can represent an expression profile of a cell. A non-root, non-leaf cluster can represent expression profiles of cells represented by the child clusters of the non-root, non-leaf clusters. The root cluster can represent expression profiles of its child clusters.

In some embodiments, clustering the expression profiles of the plurality of cells based on distances between the expression profiles of the plurality of cells at block 608 comprises: assigning each expression profile of the plurality of cells to a different leaf cluster in the plurality of clusters; and iteratively combining a first cluster and a second cluster of the plurality of clusters to generate a parent cluster of the first cluster and the second cluster if the second cluster is the closest cluster of the plurality of cluster to the first cluster. The distance between the first cluster and the second cluster can be the maximum distance between any cell with an expression profile represented by the first cluster and any cell with an expression profile represented by the second cluster.

In some embodiments, an intra-cluster correlation of the first cluster and an intra-cluster correlation of the second cluster are higher than an inter-cluster correlation of the first cluster and the second cluster. A measure or an indication of an intra-cluster correlation of the first cluster and an intra-cluster correlation of the second cluster is higher than an inter-cluster correlation of the first cluster and the second cluster. The measure of the intra-cluster correlation of the first cluster and the intra-cluster correlation of the second cluster can be based on at least one of: an intra-cluster maximum correlation of the first cluster and the second cluster, an intra-cluster average correlation of the first cluster and the second cluster, an intra-cluster median correlation of the first cluster and the second cluster, an intra-cluster minimum correlation of the first cluster and the second cluster, and any combinations thereof. The intra-cluster correlation of the first cluster can be based on at least one of: an intra-cluster maximum correlation of the first cluster, an intra-cluster average correlation of the first cluster, an intra-cluster median correlation of the first cluster, an intra-cluster minimum correlation of the first cluster, and any combinations thereof. The intra-cluster correlation of the second cluster can be based on at least one of: an intra-cluster maximum correlation of the second cluster, an intra-cluster average correlation of the second cluster, an intra-cluster median correlation of the second cluster, an intra-cluster minimum correlation of the second cluster, and any combinations thereof. The inter-cluster correlation of the first cluster and the second cluster can be based on at least one of: an inter-cluster maximum correlation of the first cluster and the second cluster, an inter-cluster average correlation of the first cluster and the second cluster, an inter-cluster median correlation of the first cluster and the second cluster, an inter-cluster minimum correlation of the first cluster and the second cluster, and any combinations thereof.

In some embodiments, the method 600 can include, prior to clustering expression profiles of the plurality of cells to generate the plurality of clusters of expression profiles based on the distances between the expression profiles of the plurality of cells at block 608: determining a distance data structure (e.g., a distance matrix) of the expression profiles of the plurality of cells. The matrix can have a dimension of n×n, wherein n denotes the number of expression profiles received at block 604. Each diagonal element of the distance matrix has a value of zero. Clustering the expression profiles of the plurality of cells to generate the plurality of clusters of expression profiles based on the distances between the expression profiles of the plurality of cells at block 608 can comprise: clustering the expression profiles of the plurality of cells to generate the plurality of clusters of expression profiles based on the distance data structure. The distances between the expression profiles of the plurality of cells can be pairwise correlation distances between the expression profiles of the plurality of cells.

In some embodiments, the method 600 can include, prior to determining the distance data structure in (i), log-transforming the target counts data structure into a log-transformed target counts data structure (e.g., a log-transformed target counts matrix). Determining the distance structure of elements of the target counts data structure comprises determining the distance data structure of the log-transformed target counts data structure. Clustering the expression profiles of the plurality of cells to generate the plurality of clusters of expression profiles based on the distances between the expression profiles of the plurality of cells at block 608 can comprise clustering the expression profiles of the plurality of cells based on the log-transformed target counts data structure and the distance data structure to generate the plurality of clusters. Log-transforming the target counts data structure into the log-transformed target counts data structure can comprise increasing the value of each element of the target counts data structure by an increment. The increment can be, for example, 1, 2, 3, 4, 5, 6, 7, 8, 9, 10, or more.

At block 612, the method 600 can include adding each cluster of the clusters of the expression profiles with two or more child clusters to a merging cluster set if associations between the cluster and its child clusters are invalid (e.g., the differences between the child clusters are not significant). In some embodiments, if the expression profiles have been clustered at block 608 to generate a dendrogram, the method 600 can add each cluster with two or more child clusters to a merging cluster set by splitting and testing the dendrogram to generate a set of labels as described with reference to FIG. 4, such as block 416 of FIG. 4.

In some embodiments, for each cluster with two or more child clusters, if associations between the cluster with the two or more child clusters are invalid, the method 600 can add the cluster to a merging cluster set by: while traversing through each cluster of the dendrogram from the root cluster of the dendrogram to the plurality of leaf clusters of the dendrogram: (1) determining whether associations of the cluster with child clusters of the cluster are valid or invalid; and (2) if the associations are invalid, adding the cluster to a merging cluster set.

At block 616, the method 600 can include merging each cluster in the merging cluster set with its closest cluster in the merging cluster set if a distance between the two clusters is within a merging distance threshold. The merged cluster comprises expression profiles of the first cluster and the second cluster. The method 600 can merge each cluster in the merging cluster set with its closest cluster as described with reference to FIG. 4, such as block 420 of FIG. 4.

In some embodiments, the method 600 can include, at each cluster when traversing the plurality of clusters of the dendrogram: if the associations are valid, continuing traversing from the cluster to the left child cluster and the right child cluster of the cluster; and if the associations are invalid, discontinue traversing from the cluster to the left child cluster and the right child cluster of the cluster. Determining whether the associations of the cluster with the child clusters of the cluster are valid or invalid can comprise: determining the associations to be valid if the distance between the left child cluster and the right child cluster is above an association threshold, and otherwise invalid.

In some embodiments, at least one of an intra-node correlation of the first node and an intra-node correlation of the second node can be higher than an inter-node correlation of the first node and the second node. A measure or an indication of an intra-node correlation of the first node and an intra-node correlation of the second node can be higher than an inter-node correlation of the first node and the second node. The measure of the intra-node correlation of the first node and the intra-node correlation of the second node can be based on at least one of: an intra-node maximum correlation of the first node and the second node, an intra-node average correlation of the first node and the second node, an intra-node median correlation of the first node and the second node, an intra-node minimum correlation of the first node and the second node, and any combinations thereof. The intra-node correlation of the first node can be based on at least one of: an intra-node maximum correlation of the first node, an intra-node average correlation of the first node, an intra-node median correlation of the first node, an intra-node minimum correlation of the first node, and any combinations thereof. The intra-node correlation of the second node can be based on at least one of: an intra-node maximum correlation of the second node, an intra-node average correlation of the second node, an intra-node median correlation of the second node, an intra-node minimum correlation of the second node, and any combinations thereof. The inter-node correlation of the first node and the second node can be based on at least one of: an inter-node maximum correlation of the first node and the second node, an inter-node average correlation of the first node and the second node, an inter-node median correlation of the first node and the second node, an inter-node minimum correlation of the first node and the second node, and any combinations thereof.

In some embodiments, the distance between the left child cluster and the right child cluster can be determined based on a statistical test performed on each target of the plurality of targets between expression profiles represented by the left child cluster and the right child cluster. The statistical test can be, for example, a Welch's t-test. The distance between the left child cluster and the right child cluster can be determined based on the maximum p-value of the statistical test performed on the each target of the plurality of targets between expression profile represented by the left child cluster and each expression profile represented by the right child cluster.

In some embodiments, the method 600 comprises, prior to merging the first cluster with the second cluster to generate the merged cluster at block 616: merging each third cluster in the merging cluster set representing an expression profile of a single cell with a fourth cluster in the merging cluster set if a distance between the third cluster and the fourth cluster is within a cluster distance threshold. The method can comprise classifying the plurality of cells based on the clusters in the merging cluster set that represent expression profiles of the cells. The method can comprise designing a whole transcriptome assay based on the targets for distinguishing cell types identified or designing a targeted transcriptome assay based on the targets for distinguishing cell types identified.

In some embodiments, the method 600 comprises, at each cluster when traversing the plurality of clusters of the dendrogram: (3) adding the cluster to the merging cluster set if the cluster represents an expression profile of a single cell. The method can comprise, at each cluster when traversing the plurality of clusters of the dendrogram: assigning a cluster label to the cluster. In some embodiments, if the cluster represents an expression profile of a single cell, the cluster label of the cluster comprises a single cell designation, otherwise, if the cluster is the left child cluster of the parent cluster, the cluster label of the cluster comprises the cluster label of the parent cluster and a left designation, and otherwise, the cluster label of the cluster comprises the cluster label of the parent cluster and a right designation.

At block 620, the method 600 can include identifying targets for distinguishing cell types based on expression profiles of the plurality of targets of cells represented by each cluster in the merging cluster set. The method 600 can identify the targets for distinguishing cell types as described with reference to FIG. 4, such as block 424 of FIG. 4. In some embodiments, for each cluster in the merging cluster set, identifying the targets for distinguishing the cell types based on the expression profiles of the plurality of targets of the cells represented by the cluster comprises: determining a difference, between expression profiles represented by the cluster and expression profiles represented by another cluster in the merging cluster set, in numbers of molecular labels with distinct sequences associated with the targets for distinguishing the cell types is greater than a significance threshold.

Sequencing

In some embodiments, estimating the number of different barcoded targets (e.g., stochastically barcoded targets) can comprise determining the sequences of the labeled targets, the spatial label, the molecular label, the sample label, the cell label, or any product thereof (e.g. labeled-amplicons, or labeled-cDNA molecules). An amplified target can be subjected to sequencing. Determining the sequence of a barcoded target (e.g., a stochastically barcoded target) or any product thereof can comprise conducting a sequencing reaction to determine the sequence of at least a portion of a sample label, a spatial label, a cell label, a molecular label, at least a portion of the labeled target (e.g., stochastically labeled target), a complement thereof, a reverse complement thereof, or any combination thereof.

Determination of the sequence of a barcoded target or a stochastically barcoded target (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the barcoded target (e.g., stochastically barcoded target) or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the barcoded target or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can be utilized. In some embodiment, sequencing can comprise MiSeq sequencing. In some embodiment, sequencing can comprise HiSeq sequencing.

The labeled targets (e.g., stochastically labeled targets) can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the barcoded targets comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly(T) tail by capturing the mRNAs from the sample.

Determining the sequences of the spatial labels and the molecular labels of the plurality of the barcodes (e.g., stochastic barcodes) can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or a number or a range between any two of these values, of the plurality of barcodes. Determining the sequences of the labels of the plurality of barcodes, for example the sample labels, the spatial labels, and the molecular labels, can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{15}$, $10^{19}$, $10^{20}$, or a number or a range between any two of these values, of the plurality of barcodes. Sequencing some or all of the plurality of barcodes can include generating sequences with read lengths of, of about, of at least, or of at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, of nucleotides or bases.

Sequencing can comprise sequencing at least or at least about 10, 20, 30, 40, 50, 60, 70, 80, 90, 100 or more nucleotides or base pairs of the barcoded targets. For example, sequencing can comprise generating sequencing data with sequences with read lengths of 50, 75, or 100, or more nucleotides by performing polymerase chain reaction (PCR) amplification on the plurality of barcoded targets. Sequencing can comprise sequencing at least or at least about 200, 300, 400, 500, 600, 700, 800, 900, 1,000 or more nucleotides or base pairs of the barcoded targets. Sequencing can comprise sequencing at least or at least about 1500, 2000, 3000, 4000, 5000, 6000, 7000, 8000, 9000, or 10000 or more nucleotides or base pairs of the barcoded targets.

Sequencing can comprise at least about 200, 300, 400, 500, 600, 700, 800, 900, 1,000 or more sequencing reads per run. In some embodiments, sequencing comprises sequencing at least or at least about 1500, 2000, 3000, 4000, 5000, 6000, 7000, 8000, 9000, or 10000 or more sequencing reads per run. Sequencing can comprise less than or equal to about 1,600,000,000 sequencing reads per run. Sequencing can comprise less than or equal to about 200,000,000 reads per run.

Samples

In some embodiments, the plurality of targets can be comprised in one or more samples. A sample can comprise one or more cells, or nucleic acids from one or more cells. A sample can be a single cell or nucleic acids from a single cell. The one or more cells can be of one or more cell types. At least one of the one or more cell types can be brain cell, heart cell, cancer cell, circulating tumor cell, organ cell, epithelial cell, metastatic cell, benign cell, primary cell, circulatory cell, or any combination thereof.

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus such as single-stranded (+ strand or "sense") DNA viruses (e.g. parvoviruses), or double-stranded RNA viruses (e.g. reoviruses). In some embodiments, the cells are bacteria. These can include either gram-positive or gram-negative bacteria. In some embodiments, the cells are fungi. In some embodiments, the cells are protozoans or other parasites.

As used herein, the term "cell" can refer to one or more cells. In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Execution Environment

Figure 7:
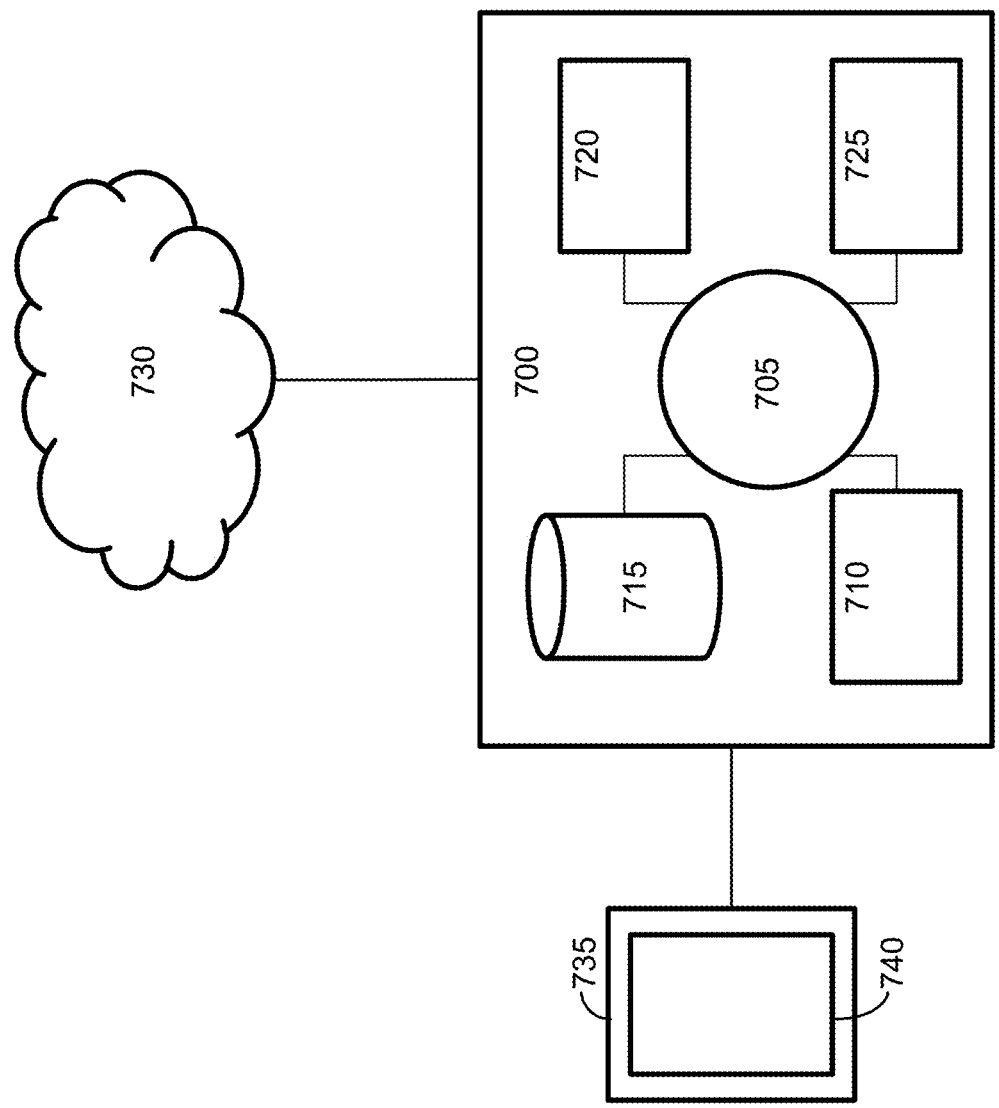
FIG. 7 is a block diagram of an illustrative computing system configured to implement methods of the disclosure.
Figure 8A:
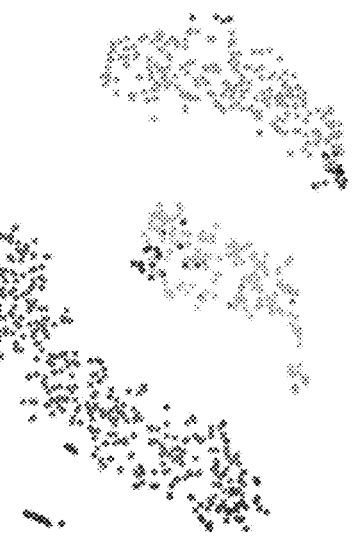
FIGS. 8A-8D show non-limiting exemplary plots of expression profiles in a two dimensional space after splitting and merging the expression profiles of single cells.
Figure 8B:
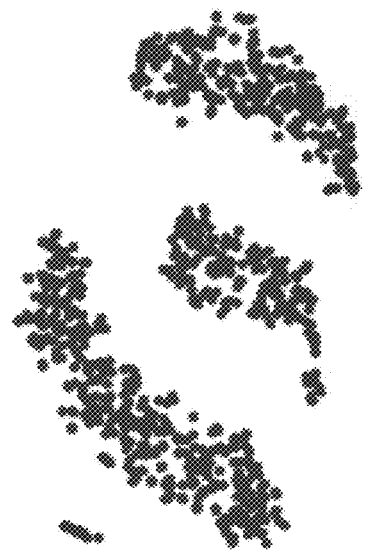
Figure 8C:
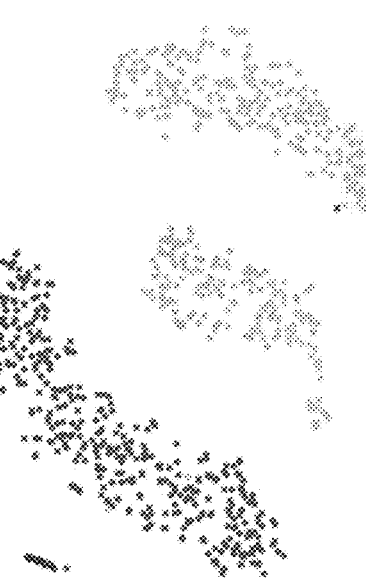
Figure 8D:
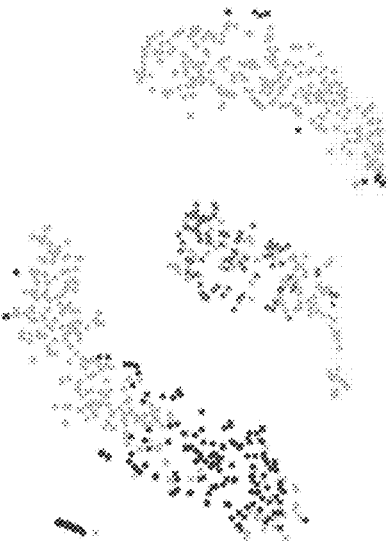

The present disclosure provides computer systems that are programmed to implement methods of the disclosure (e.g., the method 400 or the method 600). FIG. 7 shows a computer system 700 that is programmed or otherwise configured to implement any of the methods disclosed herein. The computer system 700 can be an electronic device of a user or a computer system that is remotely located with respect to the electronic device. The electronic device can be a mobile electronic device.

The computer system 700 includes a central processing unit (CPU, also "processor" and "computer processor" herein) 705, which can be a single core or multi core processor, or a plurality of processors for parallel processing. The computer system 700 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 700 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 700, can implement a peer-to-peer network, which may enable devices coupled to the computer system 700 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback. The CPU 705 can be part of a circuit, such as an integrated circuit. One or more other components of the system 700 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 700 in some cases can include one or more additional data storage units that are external to the computer system 700, such as located on a remote server that is in communication with the computer system 700 through an intranet or the Internet.

The computer system 700 can communicate with one or more remote computer systems through the network 730. For instance, the computer system 700 can communicate with a remote computer system of a user (e.g., a microbiologist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 700 via the network 730.

The computer system 700 can include or be in communication with an electronic display 735 that comprises a user interface (UI) 740 for providing, for example, an output indicative of string co-occurrence or interactions of a plurality of taxa of microorganisms, as represented by strings. Examples of UI's include, without limitation, a graphical user interface (GUI) and web-based user interface.

Methods as described herein can be implemented by way of machine (e.g., computer processor) executable code stored on an electronic storage location of the computer system 700, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 700, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

In some embodiments, some or all of the analysis functionality of the computer system 700 can be packaged in a single software package. In some embodiments, the complete set of data analysis capabilities can comprise a suite of software packages. In some embodiments, the data analysis software can be a standalone package that is made available to users independently of an assay instrument system. In some embodiments, the software can be web-based, and can allow users to share data. In some embodiments, commercially-available software can be used to perform all or a portion of the data analysis, for example, the Seven Bridges (https://www.sbgenomics.com/) software can be used to compile tables of the number of copies of one or more genes occurring in each cell for the entire collection of cells.

Methods and systems of the present disclosure can be implemented by way of one or more algorithms or methods. A method can be implemented by way of software upon execution by the central processing unit 705. Exemplary applications of algorithms or methods implemented by way of software include bioinformatics methods for sequence read processing (e.g., merging, filtering, trimming, clustering), alignment and calling, and processing of string data and optical density data (e.g., most probable number and cultivable abundance determinations).

In an exemplary embodiment, the computer system 700 can perform data analysis on the sequence datasets generated by performing single cell, stochastic barcoding assays. Examples of data analysis functionality include, but are not limited to, (i) algorithms for decoding/demultiplexing of the sample label, cell label, spatial label, and molecular label, and target sequence data provided by sequencing the stochastic barcode library created in running the assay, (ii) algorithms for determining the number of reads per gene per cell, and the number of unique transcript molecules per gene per cell, based on the data, and creating summary tables, (iii) statistical analysis of the sequence data, e.g., for clustering of cells by gene expression data, or for predicting confidence intervals for determinations of the number of transcript molecules per gene per cell, etc., (iv) algorithms for identifying sub-populations of rare cells, for example, using principal component analysis, hierarchical clustering, k-mean clustering, self-organizing maps, neural networks etc., (v) sequence alignment capabilities for alignment of gene sequence data with known reference sequences and detection of mutation, polymorphic markers and splice variants, and (vi) automated clustering of molecular labels to compensate for amplification or sequencing errors. In some embodiments, the computer system 700 can output the sequencing results in useful graphical formats, e.g., heatmaps that indicate the number of copies of one or more genes occurring in each cell of a collection of cells. In some embodiments, the computer system 700 can execute algorithms for extracting biological meaning from the sequencing results, for example, by correlating the number of copies of one or more genes occurring in each cell of a collection of cells with a type of cell, a type of rare cell, or a cell derived from a subject having a specific disease or condition.

In some embodiment, the computer system 700 can execute algorithms for comparing populations of cells across different biological samples.

EXAMPLES

Some aspects of the embodiments discussed above are disclosed in further detail in the following examples, which are not in any way intended to limit the scope of the present disclosure.

Example 1

Clustering by Recursive Dendrogram Splitting and Testing Followed by Merging

This example describes a clustering method by recursive splitting (e.g., recursive dendrogram splitting) and testing followed by merging.

Notes

In the method illustrated in this example, during the dendrogram splitting step, splits are (e.g., by default) deemed biologically relevant if the algorithm can find at least one gene that achieved a low-enough p-value (or a high enough −log 10(p-value)). In other words, the only hyper-parameter to be tuned is the score threshold parameter in some embodiments. A higher score threshold (e.g. 100) corresponds to a lower p-value (10e-100), which means that a more significant gene must be found in order for the split to be deemed valid. Higher score thresholds result in a smaller number of clusters.

If too many clusters are generated after the split step, then a user can try increasing the score threshold. If too few clusters are generated split step, then a user can try decreasing the score threshold. Multiple score thresholds can be tested on the same distance matrix. By precomputing the distance matrix, a lot of computation time can be saved.

If sweeping through different score thresholds continues to generate nonsensical results, then the issue may lie with the dendrogram generated in the first place (i.e., the distance matrix). As shown in cell [3] below, the first step of the algorithm requires going from the matrix of molecule counts to a distance matrix (the preprocessing step). It may be desirable to try a different kind of preprocessing. A user can perhaps try another distance metric, try not taking the log, or prefiltering cells and/or genes which may generate a more accurate distance metric for your application.

If the splitting step generates a lot of small clusters that seem irrelevant, then the disband percentile parameter may be decreased. This parameter decides whether or not to keep a final cluster based on how many of its pairwise distances lie within the bottom disband percentile of overall pairwise distances. Running the algorithm with a disband percentile of 20, for example, will only keep a cluster if at least one pairwise distance lies within the bottom 20% of overall distances.

To determine why a cluster is separated into two clusters, identify those two clusters and do a pairwise t-test analysis. This can be done in cell [13] in Example 2 for every pair of clusters. This function will show the markers that distinguished the two clusters. Also check out the Exploring feature of how splits were decided to see the exact step in the splitting algorithm that resulted in the split.

To determine if incorrect clusters are being merged together, decrease the score threshold parameter in the merge step. The greater the score threshold here, the more likely two different clusters will be merged together. Also check out the Exploring feature of how merges were decided to see the exact step in the merging algorithm that resulted in the merge.

To identify more outliers, try decreasing the outlier_threshold_percentile_parameter in the merging step.

Dependencies

The modules had the following dependencies:—numpy (1.10.4)—scipy (0.17.0)—matplotlib (1.5.1)—sklearn (0.17.1)—networkx (1.11)—community—rpy2 (2.8.2)

networkx, community, and rpy2 are not required by default. networkx and community are used for community detection. networkx is also used for maxed-weight-matching (as a metric of how close two sets of labels are). rpy2 is used for running sigclust, a statistical test for whether two populations should actually be one population. To run sigclust, the user may also need to have R installed along with the sigclust package.

In [1]: # Load relevant modules and libraries
% load_ext autoreload
% autoreload 2
% matplotlib inline
from dendrosplit import split,merge import pickle
import numpy as np
import matplotlib.pyplot as plt np.set_printoptions(precision=2,suppress=True)

Running the Pipeline

The input to the pipeline is an N-by-M matrix of molecular counts (natural numbers) called 'X'. 'genes' is a length-M list of gene names. 'x1' and 'x2' represent the 2-D embedding of the data using whatever method the user chose. 'x1' and 'x2' are used solely for visualizing the results of the pipeline along with intermediate steps. The algorithm requires that all columns of 'X' that sum to 0 are removed, and this cell of code takes care of that.

In [2]: # Load data
dataset='Resolve4'
pickledir='/Users/user1/Desktop/datasets/'
X,genes=pickle.load(file(pickledir+dataset+'.pickle'))
x1,x2=pickle.load(file(pickledir+dataset+'tsne.pickle'))
Remove columns of X that sum to 0
X,genes=split.filter_genes(X,genes)
Kept 19307 genes for having >0 counts across all cells A distance matrix can be first generated from the counts matrix. The cell below accomplishes this by computing the pairwise correlation distances between log-transformed samples (log(X+1)). The splitting part of the algorithm required only the counts matrix as input although a user can feed in a distance matrix as well as shown below. This part of the algorithm returned a length-N set of labels (strings) for the samples along with 'history', a data structure that tracked all intermediate information generated by the algorithm. 'history' was useful for later functions used to dissect how the algorithm generated such labels (and which features were most important for generating such labels). The labels were strings indicating where a cluster is located according to the dendrogram generated using the distance matrix. For example, 'rLLR' meant that this point belongs to the root's left subtree's left subtree's right subtree.

In [3]: # Get first set of labels. Computing the distance matrix outside the algorithm is highly recommend
D=split.log_correlation(X)
ys,shistory=split.dendrosplit((D,X), preprocessing, 'precomputed', score_threshold=10, verbose=True, disband_percentile=50)
    Potential split result: 883 and 3 dendrosplit/feature selection.py:106: RuntimeWarning: divide by zero encountered in log 10
    gene_scores=np.nan_to_num(-np. log 10(p[keep_inds]))
    Split score 1.8E+308
Potential split result: 1 and 882
Potential split result: 484 and 398
/Users/user1/anaconda2/lib/python2.7/site-packages/scipy/stats/
_distn_infrastructure.py:1748: Runtime
cond1=(scale>0) & (x>self.a) & (x<self.b)
/Users/user1/anaconda2/lib/python2.7/site-packages/scipy/stats/
_distn_infrastructure.py:1748: Runtime
cond1=(scale>0) & (x>self.a) & (x<self.b)
/Users/user 1/anaconda2/lib/python2.7/site-packages/scipy/stats/
_distn_infrastructure.py:1749: Runtime
cond2=cond0 & (x<=self.a)
    Split score 182.26
Potential split result: 481 and 3 Split score 1.8E+308
Potential split result: 1 and 480
Potential split result: 1 and 479
Potential split result: 195 and 284
    Split score 125.49
Potential split result: 177 and 18
    Split score 15.35
Potential split result: 1 and 176
Potential split result: 1 and 175
Potential split result: 1 and 174
Potential split result: 12 and 162
    Split score 18.88
Potential split result: 1 and 11
Potential split result: 1 and 10
Potential split result: 2 and 8
    Split score 6.11
Potential split result: 1 and 161
Potential split result: 1 and 160
Potential split result: 28 and 132
    Split score 12.32
Potential split result: 25 and 3
    Split score 13.94
Potential split result: 1 and 24
Potential split result: 11 and 13
    Split score 4.77
Potential split result: 1 and 2
Potential split result: 1 and 1
Disbanding (points in cluster too far from each other)
Potential split result: 122 and 10
    Split score 18.52
Potential split result: 13 and 109
    Split score 24.92
Potential split result: 6 and 7
    Split score 3.77
Potential split result: 105 and 4
    Split score 31.72
Potential split result: 15 and 90
    Split score 11.31
Potential split result: 3 and 12
    Split score 6.55
Potential split result: 17 and 73
    Split score 8.91
Potential split result: 2 and 2
    Split score 1.58
Disbanding (points in cluster too far from each other)
Potential split result: 2 and 8
    Split score 5.79
Potential split result: 1 and 17

Potential split result: 1 and 16
Potential split result: 1 and 15
Potential split result: 4 and 11
    Split score 4.57
Potential split result: 1 and 283
Potential split result: 1 and 282
Potential split result: 1 and 281
Potential split result: 271 and 10
    Split score 38.04
Potential split result: 2 and 269
    Split score 233.23
Potential split result: 1 and 1
Disbanding (points in cluster too far from each other)
Potential split result: 1 and 268
Potential split result: 265 and 3
    Split score 80.24
Potential split result: 4 and 261
    Split score 100.26
Potential split result: 1 and 3
Potential split result: 1 and 2
Potential split result: 1 and 1
Disbanding (points in cluster too far from each other)
Potential split result: 192 and 69
    Split score 9.66
Potential split result: 1 and 2
Potential split result: 1 and 1
Disbanding (points in cluster too far from each other)
Potential split result: 2 and 8
    Split score 5.12
Potential split result: 1 and 2
Potential split result: 1 and 1
Disbanding (points in cluster too far from each other)
Potential split result: 1 and 397
Potential split result: 1 and 396
Potential split result: 1 and 395
Potential split result: 392 and 3
    Split score 228.58
Potential split result: 1 and 391
Potential split result: 1 and 390
Potential split result: 1 and 389
Potential split result: 1 and 388
Potential split result: 1 and 387
Potential split result: 1 and 386
Potential split result: 32 and 354
    Split score 33.24
Potential split result: 1 and 31
Potential split result: 1 and 30
Potential split result: 21 and 9
    Split score 7.20
Potential split result: 1 and 353
Potential split result: 1 and 352
Potential split result: 1 and 351
Potential split result: 19 and 332
    Split score 32.86
Potential split result: 1 and 18
Potential split result: 3 and 15
    Split score 8.90
Potential split result: 6 and 326
    Split score 83.57
Potential split result: 1 and 5
Potential split result: 1 and 4
Potential split result: 2 and 2
    Split score 1.32
Disbanding (points in cluster too far from each other)
Potential split result: 3 and 323
    Split score 148.25
Potential split result: 1 and 2
Potential split result: 1 and 1
Disbanding (points in cluster too far from each other)
Potential split result: 314 and 9
    Split score 71.43
Potential split result: 221 and 93
    Split score 48.70
Potential split result: 1 and 220
Potential split result: 1 and 219
Potential split result: 1 and 218
Potential split result: 1 and 217
Potential split result: 215 and 2
    Split score 133.42
Potential split result: 166 and 49
    Split score 7.64
Potential split result: 1 and 1
Potential split result: 40 and 53
    Split score 9.31
Potential split result: 4 and 5
    Split score 3.20
Disbanding (points in cluster too far from each other)
Potential split result: 1 and 2
Potential split result: 1 and 1
Disbanding (points in cluster too far from each other)
Potential split result: 1 and 2
Potential split result: 1 and 1
Disbanding (points in cluster too far from each other)
# of times score function was called: 40
Total computational time was 9.532 s The merging step involved doing pairwise comparisons of all the clusters generated by the splitting procedure above. Clusters that were not different enough were merged together starting with the two most similar clusters. Like the splitting step, the merging step returned both labels (length-N) and a history of intermediate steps. The labels were integers. Outliers are labeled as '−1'. Please see below for an alternative approach to the merging step based on community detection.

In [4]: # Merge cluster labels
ym,mhistory=merge.dendromerge((D,X),ys,score_threshold=10,
preprocessing,'precomputed',verbose=True,outlier_threshold_percentile=90)
    0 of 886 samples are singletons
Outlier threshold is 0.51
821's nearest neighbor: 72 in cluster 76 (D=0.375)
661's nearest neighbor: 29 in cluster 76 (D=0.379)
729's nearest neighbor: 281 in cluster 76 (D=0.381)
559's nearest neighbor: 79 in cluster 76 (D=0.381)
690's nearest neighbor: 171 in cluster 76 (D=0.381)
564's nearest neighbor: 79 in cluster 76 (D=0.381)
776's nearest neighbor: 474 in cluster 38 (D=0.387)
860's nearest neighbor: 340 in cluster 38 (D=0.390)
816's nearest neighbor: 379 in cluster 78 (D=0.390)
787's nearest neighbor: 63 in cluster 38 (D=0.391)
737's nearest neighbor: 72 in cluster 76 (D=0.392)
874's nearest neighbor: 220 in cluster 76 (D=0.392)
743's nearest neighbor: 72 in cluster 76 (D=0.394)
877's nearest neighbor: 174 in cluster 76 (D=0.394)
753's nearest neighbor: 190 in cluster 76 (D=0.397)
774's nearest neighbor: 158 in cluster 38 (D=0.398)
565's nearest neighbor: 190 in cluster 76 (D=0.399)
785's nearest neighbor: 79 in cluster 76 (D=0.401)
706's nearest neighbor: 101 in cluster 18 (D=0.403)
829's nearest neighbor: 213 in cluster 38 (D=0.404)
701's nearest neighbor: 179 in cluster 76 (D=0.404)
770's nearest neighbor: 453 in cluster 38 (D=0.404)
630's nearest neighbor: 79 in cluster 76 (D=0.406)

866's nearest neighbor: 87 in cluster 38 (D=0.407)
795's nearest neighbor: 159 in cluster 76 (D=0.407)
865's nearest neighbor: 179 in cluster 76 (D=0.407)
869's nearest neighbor: 101 in cluster 18 (D=0.409)
830's nearest neighbor: 165 in cluster 38 (D=0.412)
851's nearest neighbor: 29 in cluster 76 (D=0.412)
782's nearest neighbor: 50 in cluster 76 (D=0.412)
627's nearest neighbor: 72 in cluster 76 (D=0.412)
848's nearest neighbor: 83 in cluster 76 (D=0.413)
883's nearest neighbor: 687 in cluster 12 (D=0.413)
793's nearest neighbor: 107 in cluster 76 (D=0.414)
631's nearest neighbor: 101 in cluster 18 (D=0.416)
720's nearest neighbor: 101 in cluster 18 (D=0.418)
885's nearest neighbor: 101 in cluster 18 (D=0.418)
813's nearest neighbor: 101 in cluster 18 (D=0.419)
788's nearest neighbor: 278 in cluster 38 (D=0.420)
748's nearest neighbor: 101 in cluster 18 (D=0.422)
762's nearest neighbor: 158 in cluster 38 (D=0.423)
804's nearest neighbor: 177 in cluster 18 (D=0.425)
854's nearest neighbor: 101 in cluster 18 (D=0.426)
605's nearest neighbor: 159 in cluster 76 (D=0.437)
849's nearest neighbor: 101 in cluster 18 (D=0.437)
835's nearest neighbor: 101 in cluster 18 (D=0.438)
790's nearest neighbor: 32 in cluster 76 (D=0.442)
744's nearest neighbor: 188 in cluster 38 (D=0.448)
822's nearest neighbor: 282 in cluster 38 (D=0.449)
723's nearest neighbor: 170 in cluster 76 (D=0.456)
884's nearest neighbor: 101 in cluster 18 (D=0.459)
563's nearest neighbor: 34 in cluster 76 (D=0.463)
867's nearest neighbor: 160 in cluster 18 (D=0.463)
771's nearest neighbor: 34 in cluster 76 (D=0.473)
826's nearest neighbor: 165 in cluster 38 (D=0.475)
777's nearest neighbor: 174 in cluster 76 (D=0.478)
759's nearest neighbor: 101 in cluster 18 (D=0.483)
855's nearest neighbor: 101 in cluster 18 (D=0.485)
702's nearest neighbor: 160 in cluster 18 (D=0.492)
750's nearest neighbor: 230 in cluster 76 (D=0.495)
704's nearest neighbor: 216 in cluster 78 (D=0.497)
711's nearest neighbor: 55 in cluster 76 (D=0.502)
708's nearest neighbor: 537 in cluster 78 (D=0.510)
791's nearest neighbor: 115 in cluster 76 (D=0.534)
722's nearest neighbor: 15 in cluster 76 (D=0.547)
700's nearest neighbor: 107 in cluster 76 (D=0.549)
846's nearest neighbor: 72 in cluster 76 (D=0.552)
876's nearest neighbor: 85 in cluster 76 (D=0.560)
868's nearest neighbor: 740 in cluster 78 (D=0.562)
569's nearest neighbor: 68 in cluster 76 (D=0.572)
817's nearest neighbor: 56 in cluster 76 (D=0.582)
798's nearest neighbor: 310 in cluster 38 (D=0.585)
717's nearest neighbor: 216 in cluster 78 (D=0.597)
879's nearest neighbor: 209 in cluster 76 (D=0.612)
727's nearest neighbor: 96 in cluster 76 (D=0.616)
828's nearest neighbor: 142 in cluster 38 (D=0.618)
840's nearest neighbor: 632 in cluster 78 (D=0.640)
747's nearest neighbor: 202 in cluster 76 (D=0.698)
842's nearest neighbor: 797 in cluster 38 (D=0.703)
442's nearest neighbor: 336 in cluster 78 (D=0.735)
Total number of outliers: 18
Singletons assigned (0.052 s)
Dc generated (13.181 s)
Before the merge: 14 clusters
Merging labels 0 (N=10) and 6 (N=15) with distance 3.60
Before the merge: 13 clusters
Merging labels 2 (N=15) and 4 (N=10) with distance 4.31
Before the merge: 12 clusters
Merging labels 1 (N=13) and 11 (N=25) with distance 4.37
Before the merge: 11 clusters
Merging labels 0 (N=25) and 10 (N=38) with distance 5.23
Before the merge: 10 clusters
Merging labels 3 (N=30) and 7 (N=95) with distance 6.04
Before the merge: 9 clusters
Merging labels 2 (N=10) and 5 (N=2) with distance 6.81
Before the merge: 8 clusters
Merging labels 4 (N=25) and 5 (N=63) with distance 7.19
Before the merge: 7 clusters
Merging labels 2 (N=18) and 5 (N=12) with distance 7.23
Before the merge: 6 clusters
Merging labels 3 (N=125) and 5 (N=30) with distance 9.76
Merging clusters took 25.977 s Merge based on community detection used the networkx and community python modules. The history data structure returned here only contains the input labels and the post-singleton-processing labels.

In [5]: ym_community=merge.dendromerge((D,X),ys, preprocessing='precomputed', verbose=True,outlier_threshold_percentile=90, perform_community_detection=True)

80 of 886 samples are singletons Outlier threshold is 0.51
821's nearest neighbor: 72 in cluster 76 (D=0.375)
661's nearest neighbor: 29 in cluster 76 (D=0.379)
729's nearest neighbor: 281 in cluster 76 (D=0.381)
559's nearest neighbor: 79 in cluster 76 (D=0.381)
690's nearest neighbor: 171 in cluster 76 (D=0.381)
564's nearest neighbor: 79 in cluster 76 (D=0.381)
776's nearest neighbor: 474 in cluster 38 (D=0.387)
860's nearest neighbor: 340 in cluster 38 (D=0.390)
816's nearest neighbor: 379 in cluster 78 (D=0.390)
787's nearest neighbor: 63 in cluster 38 (D=0.391)
737's nearest neighbor: 72 in cluster 76 (D=0.392)
874's nearest neighbor: 220 in cluster 76 (D=0.392)
743's nearest neighbor: 72 in cluster 76 (D=0.394)
877's nearest neighbor: 174 in cluster 76 (D=0.394)
753's nearest neighbor: 190 in cluster 76 (D=0.397)
774's nearest neighbor: 158 in cluster 38 (D=0.398)
565's nearest neighbor: 190 in cluster 76 (D=0.399)
785's nearest neighbor: 79 in cluster 76 (D=0.401)
706's nearest neighbor: 101 in cluster 18 (D=0.403)
829's nearest neighbor: 213 in cluster 38 (D=0.404)
701's nearest neighbor: 179 in cluster 76 (D=0.404)
770's nearest neighbor: 453 in cluster 38 (D=0.404)
630's nearest neighbor: 79 in cluster 76 (D=0.406)
866's nearest neighbor: 87 in cluster 38 (D=0.407)
795's nearest neighbor: 159 in cluster 76 (D=0.407)
865's nearest neighbor: 179 in cluster 76 (D=0.407)
869's nearest neighbor: 101 in cluster 18 (D=0.409)
830's nearest neighbor: 165 in cluster 38 (D=0.412)
851's nearest neighbor: 29 in cluster 76 (D=0.412)
782's nearest neighbor: 50 in cluster 76 (D=0.412)
627's nearest neighbor: 72 in cluster 76 (D=0.412)
848's nearest neighbor: 83 in cluster 76 (D=0.413)
883's nearest neighbor: 687 in cluster 12 (D=0.413)
793's nearest neighbor: 107 in cluster 76 (D=0.414)
631's nearest neighbor: 101 in cluster 18 (D=0.416)
720's nearest neighbor: 101 in cluster 18 (D=0.418)
885's nearest neighbor: 101 in cluster 18 (D=0.418)
813's nearest neighbor: 101 in cluster 18 (D=0.419)
788's nearest neighbor: 278 in cluster 38 (D=0.420)
748's nearest neighbor: 101 in cluster 18 (D=0.422)
762's nearest neighbor: 158 in cluster 38 (D=0.423)
804's nearest neighbor: 177 in cluster 18 (D=0.425)
854's nearest neighbor: 101 in cluster 18 (D=0.426)
605's nearest neighbor: 159 in cluster 76 (D=0.437)
849's nearest neighbor: 101 in cluster 18 (D=0.437)
835's nearest neighbor: 101 in cluster 18 (D=0.438)

790's nearest neighbor: 32 in cluster 76 (D=0.442)
744's nearest neighbor: 188 in cluster 38 (D=0.448)
822's nearest neighbor: 282 in cluster 38 (D=0.449)
723's nearest neighbor: 170 in cluster 76 (D=0.456)
884's nearest neighbor: 101 in cluster 18 (D=0.459)
563's nearest neighbor: 34 in cluster 76 (D=0.463)
867's nearest neighbor: 160 in cluster 18 (D=0.463)
771's nearest neighbor: 34 in cluster 76 (D=0.473)
826's nearest neighbor: 165 in cluster 38 (D=0.475)
777's nearest neighbor: 174 in cluster 76 (D=0.478)
759's nearest neighbor: 101 in cluster 18 (D=0.483)
855's nearest neighbor: 101 in cluster 18 (D=0.485)
702's nearest neighbor: 160 in cluster 18 (D=0.492)
750's nearest neighbor: 230 in cluster 76 (D=0.495)
704's nearest neighbor: 216 in cluster 78 (D=0.497)
711's nearest neighbor: 55 in cluster 76 (D=0.502)
708's nearest neighbor: 537 in cluster 78 (D=0.510)
791's nearest neighbor: 115 in cluster 76 (D=0.534)
722's nearest neighbor: 15 in cluster 76 (D=0.547)
700's nearest neighbor: 107 in cluster 76 (D=0.549)
846's nearest neighbor: 72 in cluster 76 (D=0.552)
876's nearest neighbor: 85 in cluster 76 (D=0.560)
868's nearest neighbor: 740 in cluster 78 (D=0.562)
569's nearest neighbor: 68 in cluster 76 (D=0.572)
817's nearest neighbor: 56 in cluster 76 (D=0.582)
798's nearest neighbor: 310 in cluster 38 (D=0.585)
717's nearest neighbor: 216 in cluster 78 (D=0.597)
879's nearest neighbor: 209 in cluster 76 (D=0.612)
727's nearest neighbor: 96 in cluster 76 (D=0.616)
828's nearest neighbor: 142 in cluster 38 (D=0.618)
840's nearest neighbor: 632 in cluster 78 (D=0.640)
747's nearest neighbor: 202 in cluster 76 (D=0.698)
842's nearest neighbor: 797 in cluster 38 (D=0.703)
442's nearest neighbor: 336 in cluster 78 (D=0.735)
Total number of outliers: 18
Singletons assigned (0.054 s)
Dc generated (12.773 s)
Graph constructed with 14 nodes and 24 edges (12.774 s)
Merging clusters took 12.775 s Altogether, these data demonstrate clustering by recursive splitting and testing followed by merging.

Example 2

Visualizing the Results of Clustering by Recursive Dendrogram Splitting and Testing Followed by Merging This example describes visualizing the results of clustering by recursive dendrogram splitting and testing followed by merging illustrated in Example 1.

The cluster labels generated after the splitting and merging steps were examined.

In [6]: plt.scatter(x1,x2,edgecolors='none')
_=plt.axis('off')
plt.title('Pre-clustering')
Clustering results using pre-merged labels (label singletons)
plt.figure( )
split.plot_labels_legend(x1,x2,split.str_labels_to_ints(ys))
plt.title('After splitting step')
Clustering results using post-merged labels
plt.figure( )
split.plot_labels_legend(x1,x2,ym)
plt.title('After merging step')
Clustering results using post-merged labels
plt.figure( )
split.plot_labels_legend(x1,x2,ym_community)
plt.title('After merging step using community detection')
Out[6]: <matplotlib.text.Text at 0x112674510>

FIGS. 8A-8D show non-limiting exemplary plots of expression profiles in a two dimensional space after splitting and merging the expression profiles of single cells.
Exploring how Splits were Decided The "print_history" function can be used to explore how the splitting step of the method handles the dataset using the "print_history" function. Line i describes the ith valid split. A split is deemed valid if both clusters generated are above the "min_clust_size" and the lowest p-value generated from the split is below the threshold.

In [7]: split.print_history(genes,shistory)
Pre-split: 886 L: 883 R: 3 Score: 1.8E+308 Top Gene: RPL31 Top Gene Score: 1.8E+308
Pre-split: 882 L: 484 R: 398 Score: 182.26 Top Gene: FTL Top Gene Score: 182.26
Pre-split: 484 L: 481 R: 3 Score: 1.8E+308 Top Gene: RPL23 Top Gene Score: 1.8E+308
Pre-split: 479 L: 195 R: 284 Score: 125.49 Top Gene: IGHM Top Gene Score: 125.49
Pre-split: 195 L: 177 R: 18 Score: 15.35 Top Gene: RRP7A Top Gene Score: 15.35
Pre-split: 174 L: 12 R: 162 Score: 18.88 Top Gene: ANXA11 Top Gene Score: 18.88
Pre-split: 160 L: 28 R: 132 Score: 12.32 Top Gene: TTF1 Top Gene Score: 12.32
Pre-split: 28 L: 25 R: 3 Score: 13.94 Top Gene: SRPK1 Top Gene Score: 13.94
Pre-split: 132 L: 122 R: 10 Score: 18.52 Top Gene: TOP2A Top Gene Score: 18.52
Pre-split: 122 L: 13 R: 109 Score: 24.92 Top Gene: CACYBP Top Gene Score: 24.92
Pre-split: 109 L: 105 R: 4 Score: 31.72 Top Gene: RPSA Top Gene Score: 31.72
Pre-split: 105 L: 15 R: 90 Score: 11.31 Top Gene: PSMD14 Top Gene Score: 11.31
Pre-split: 281 L: 271 R: 10 Score: 38.04 Top Gene: RNASEH2B Top Gene Score: 38.04
Pre-split: 271 L: 2 R: 269 Score: 233.23 Top Gene: GAS8 Top Gene Score: 233.23
Pre-split: 268 L: 265 R: 3 Score: 80.24 Top Gene: CNPY3 Top Gene Score: 80.24
Pre-split: 265 L: 4 R: 261 Score: 100.26 Top Gene: MZB1 Top Gene Score: 100.26
Pre-split: 395 L: 392 R: 3 Score: 228.58 Top Gene: CREB3L1 Top Gene Score: 228.58
Pre-split: 386 L: 32 R: 354 Score: 33.24 Top Gene: VMP1 Top Gene Score: 33.24
Pre-split: 351 L: 19 R: 332 Score: 32.86 Top Gene: EIF2B1 Top Gene Score: 32.86
Pre-split: 332 L: 6 R: 326 Score: 83.57 Top Gene: NUDTS Top Gene Score: 83.57
Pre-split: 326 L: 3 R: 323 Score: 148.25 Top Gene: TMSB4X Top Gene Score: 148.25
Pre-split: 323 L: 314 R: 9 Score: 71.43 Top Gene: C12orf57 Top Gene Score: 71.43
Pre-split: 314 L: 221 R: 93 Score: 48.70 Top Gene: RPL27A Top Gene Score: 48.70
Pre-split: 217 L: 215 R: 2 Score: 133.42 Top Gene: JUN Top Gene Score: 133.42

Figure 9A:
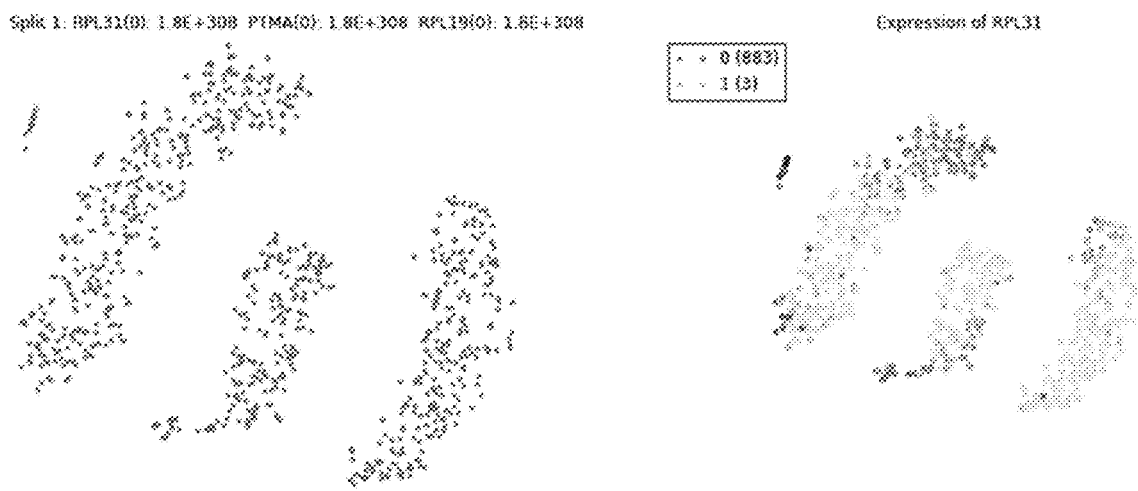
FIGS. 9A-9X are non-limiting exemplary plots of expression profiles in a two dimensional space showing how splits can be decided.
Figure 9B:
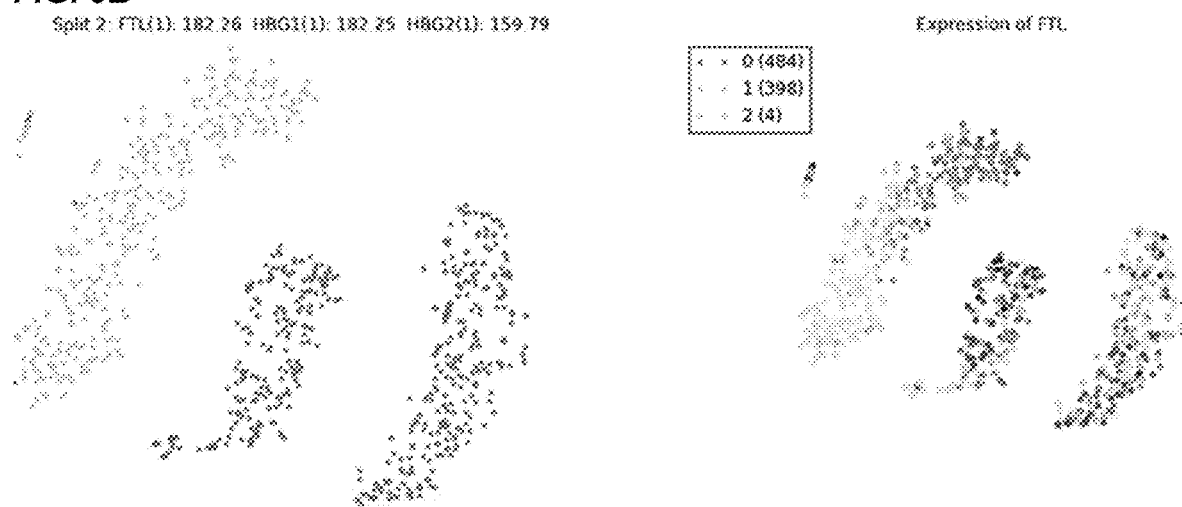
Figure 9C:
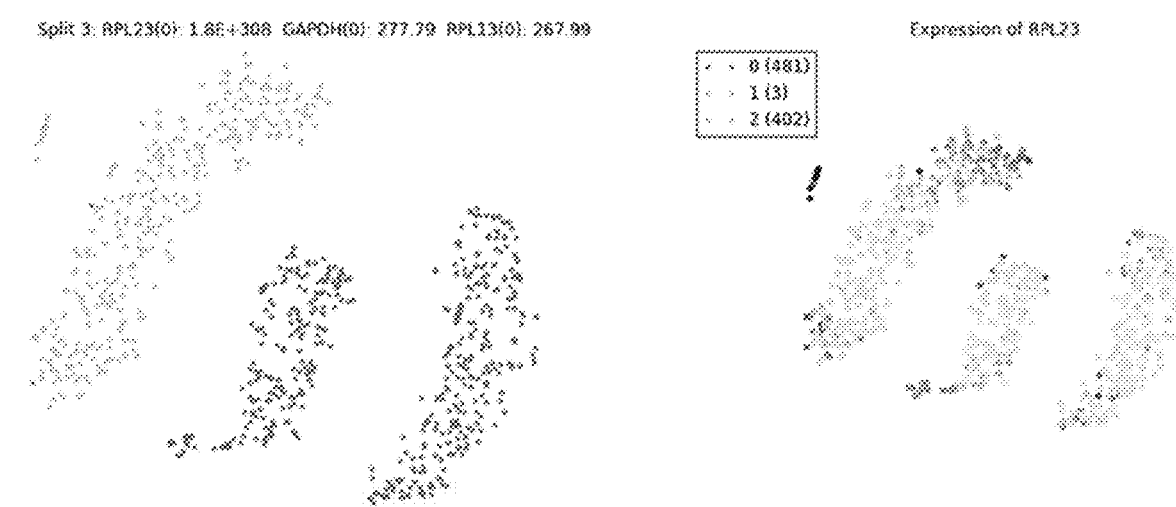
Figure 9D:
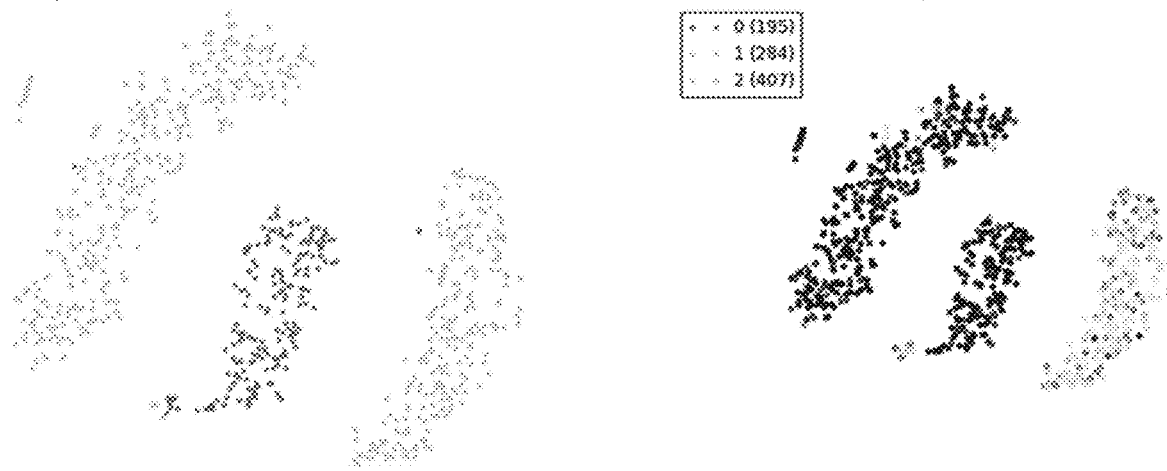
Figure 9E:
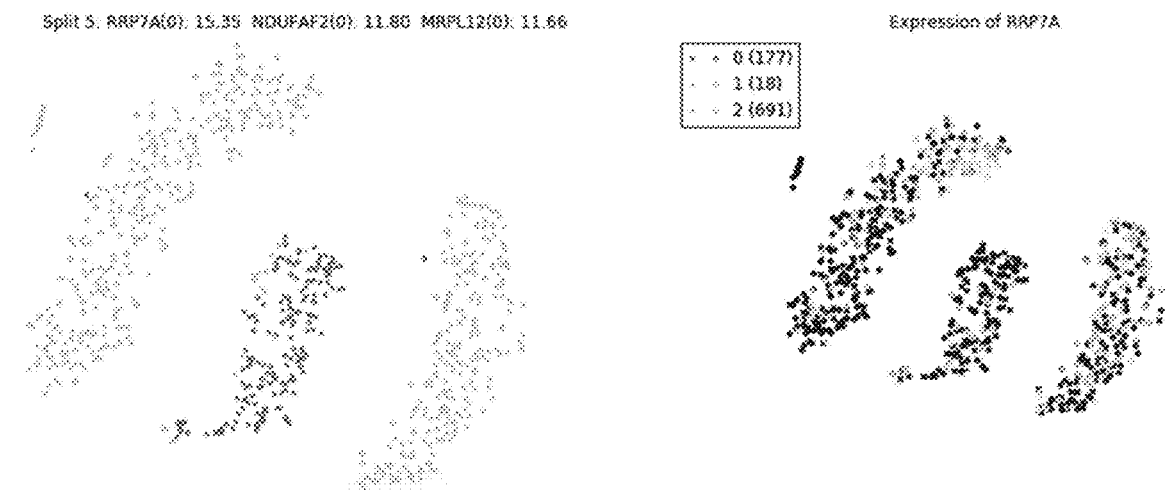
Figure 9F:
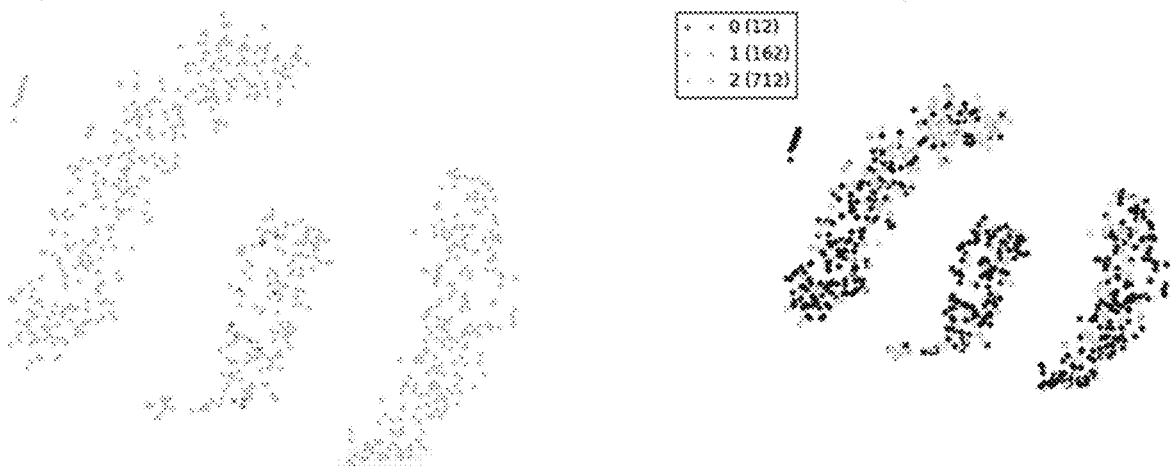
Figure 9G:
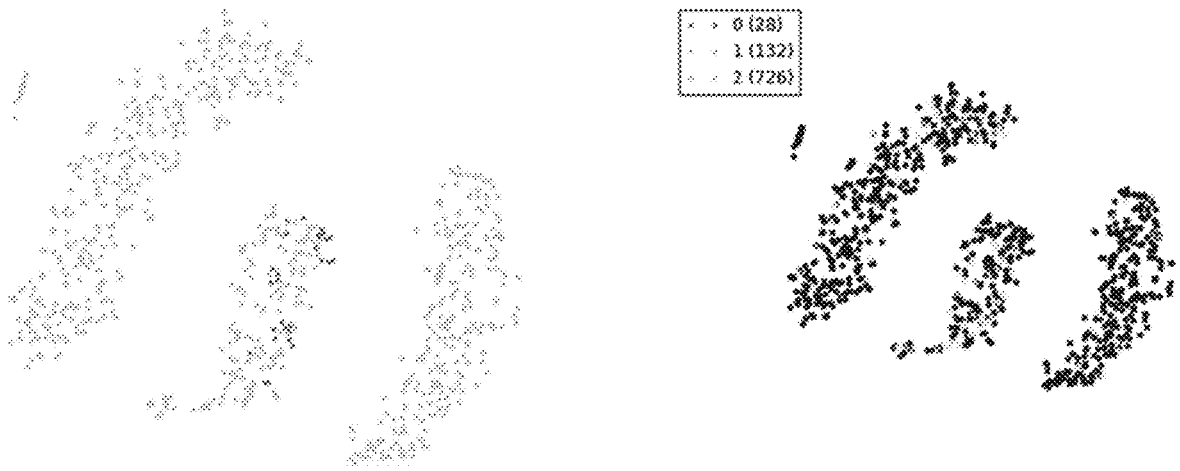
Figure 9H:
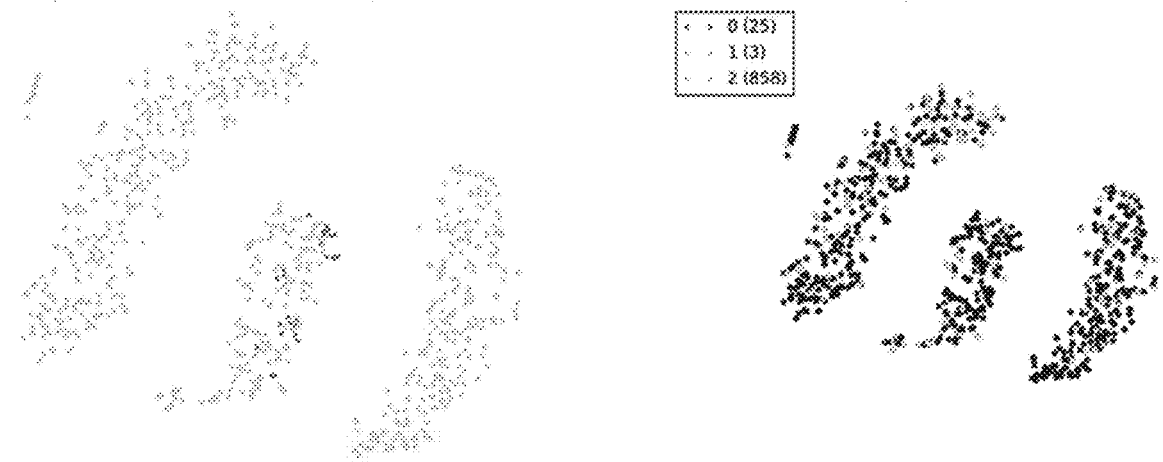
Figure 9I:
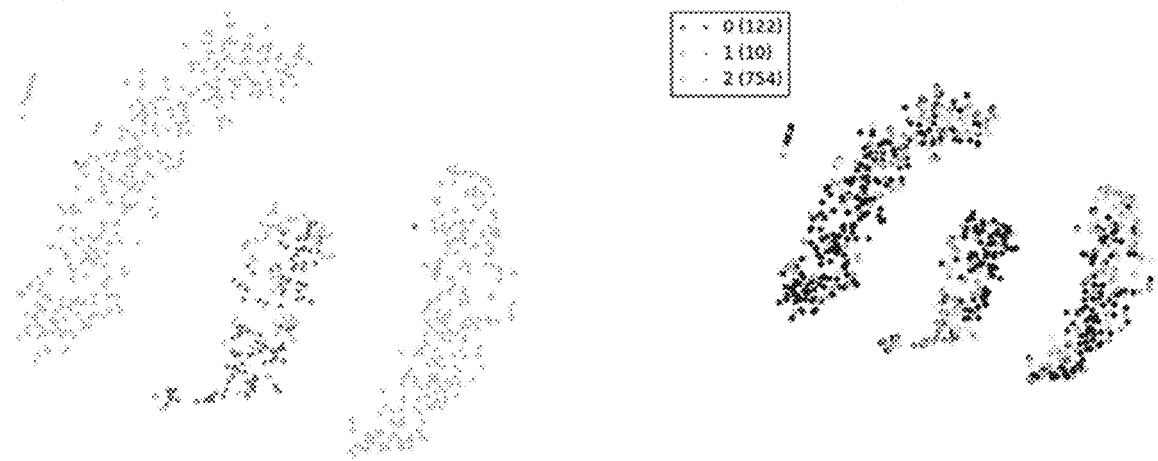
Figure 9J:
Figure 9K:
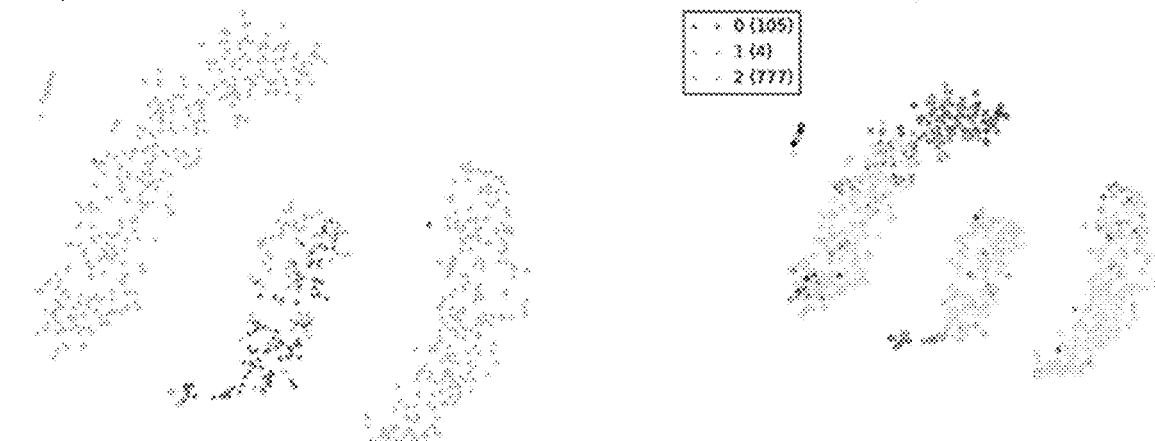
Figure 9L:
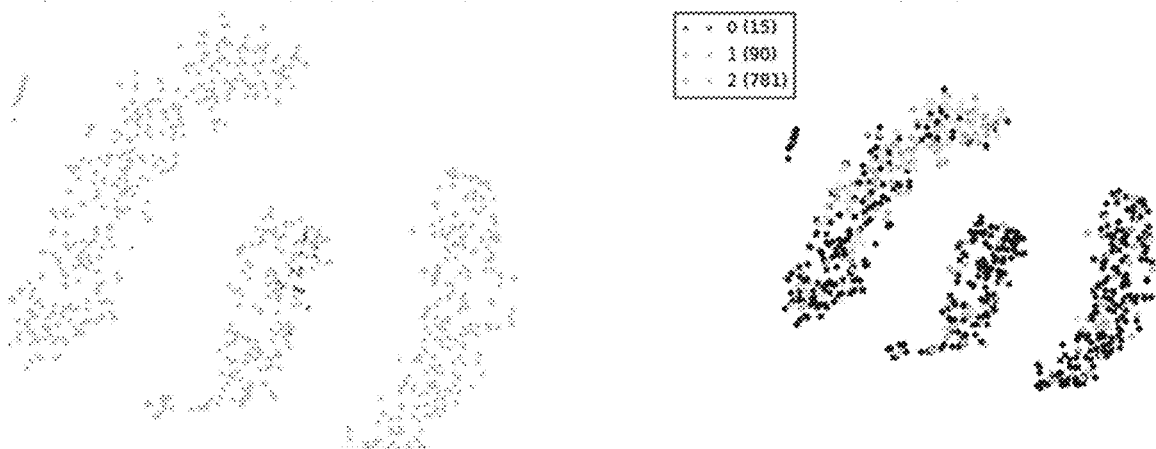
Figure 9M:
Figure 9N:
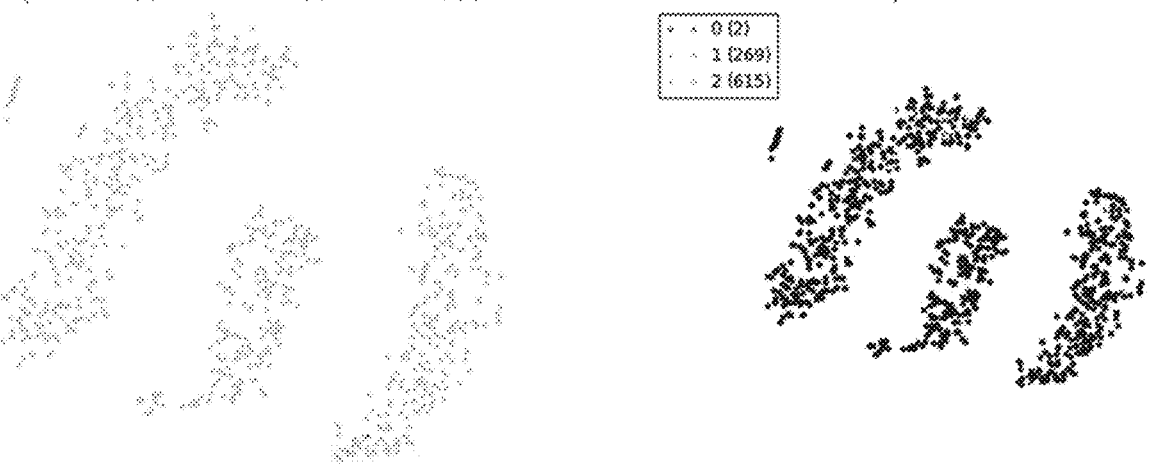
Figure 9O:
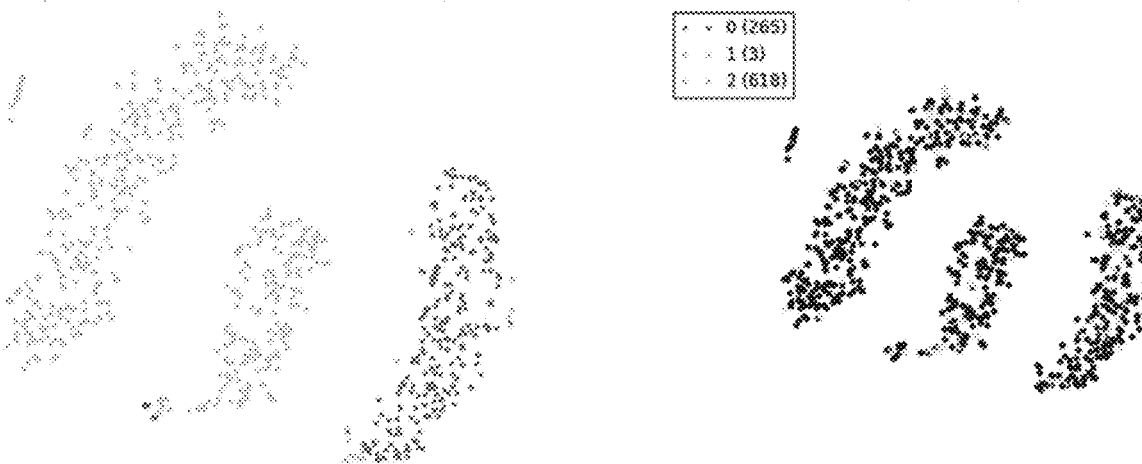
Figure 9P:
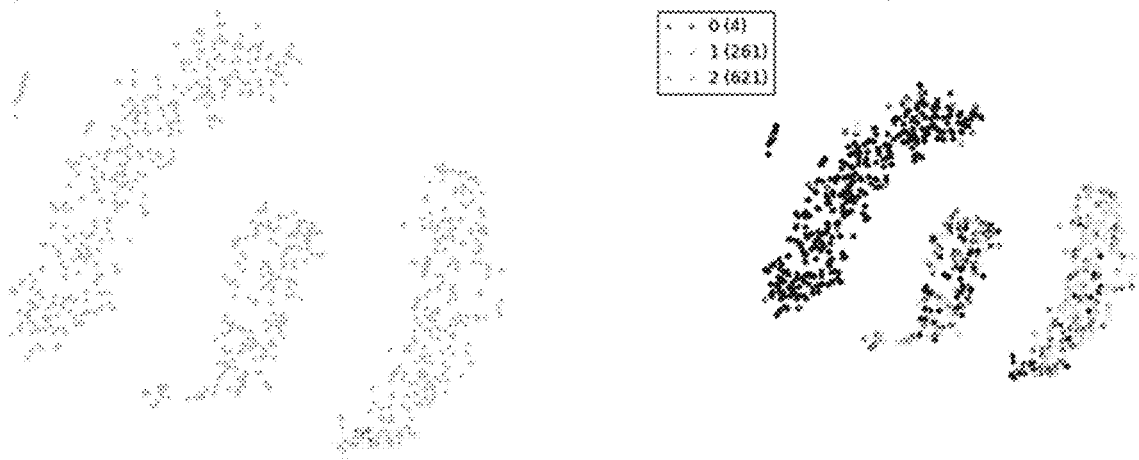
Figure 9Q:
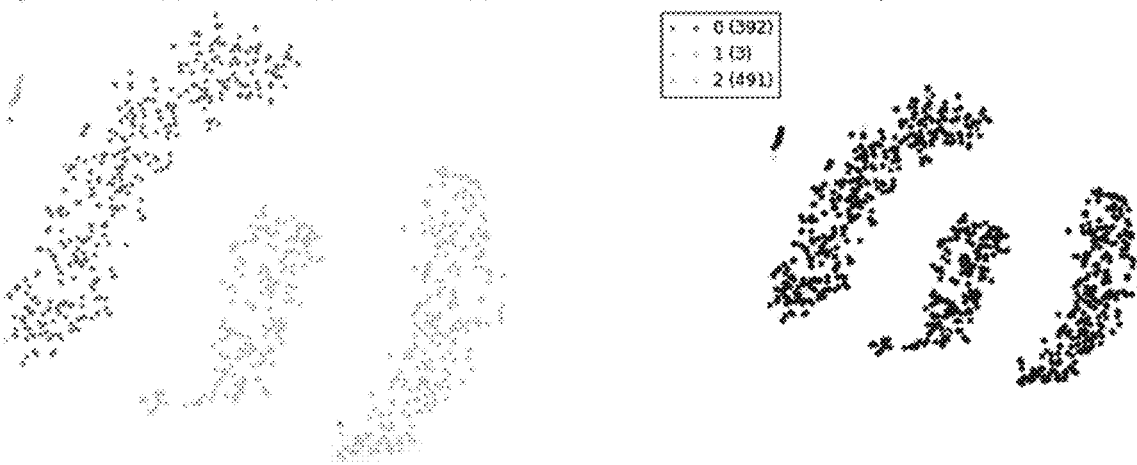
Figure 9R:
Figure 9V:
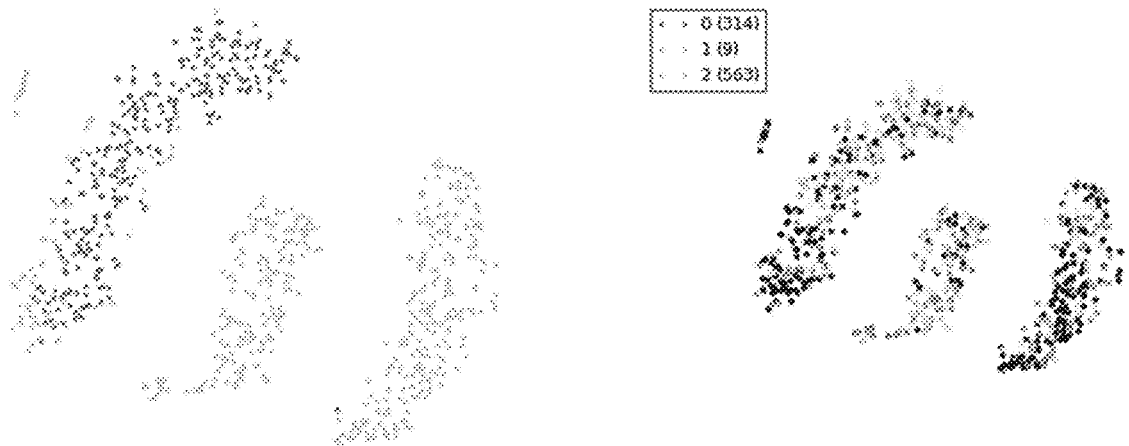
Figure 9W:
Figure 9X:
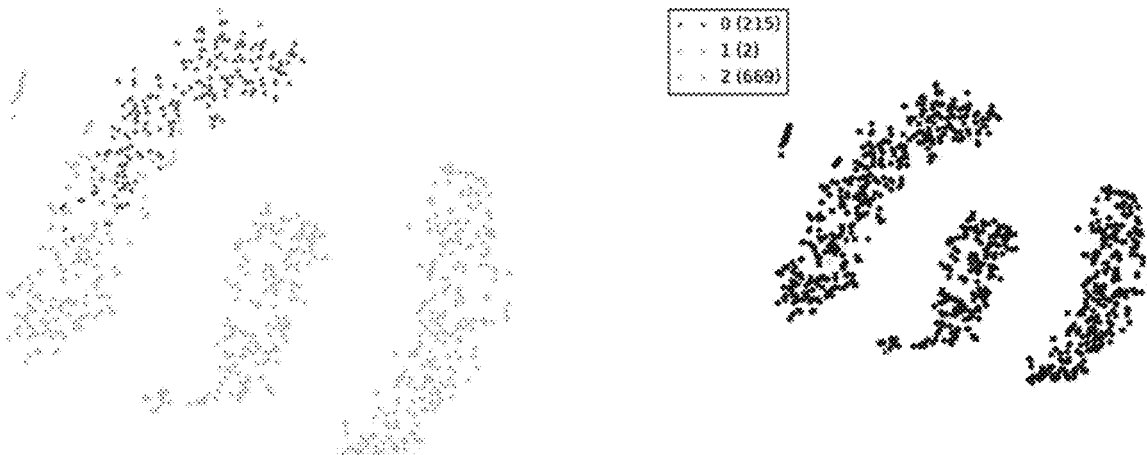

The points that were involved in each split were visualized. Each row has 2 figures. Row i describes the ith split saved. FIGS. 9A-9X are non-limiting exemplary plots of expression profiles in a two dimensional space showing how splits were decided. In each figure, the left panel indicates how the split was carried out. Blue points were not involved in the split at all. Red and green points used to be in the same cluster and were then separated. The title of the left figure indicates the split number and the 3 genes that achieved the largest t statistic (after taking an absolute value). The number associated with each gene is the −log 10 of the corresponding p value. The '0' or '1' in parenthesis next to each gene indicates the cluster that had higher mean expression of that gene. The right panel shows the log expression of the gene that achieved the largest t statistic.

In [8]: split.visualize_history(np.log(1+X),x1,x2,genes, shistory)/Users/user1/anaconda2/lib/python2.7/site-packages/matplotlib/pyplot.py:516: RuntimeWarning: More max open warning, RuntimeWarning)

The "analyze_split" function can be used to take a closer look at the genes that dictated why a particular split was kept. Use the "show_background" keyword to also display the cells not involved in the split. Use "clust" to only look at genes that are more highly expressed in a particular cluster. "num_genes" can be used to display a custom number of genes.

In [9]: # Look at split 5
split_num=5
cluster_of_interest=None
show_background=False
split.analyze_split(X,x1,x2,genes,shistory, split_num, num_genes=12,
show_background=show_background,
clust=cluster_of_interest)

Figure 10:
FIG. 10 shows a non-limiting exemplary plot of expression profiles in a two dimensional space after the fifth cycle of splitting.
Figure 11A:
FIGS. 11A-11L are non-limiting exemplary plots of expression profiles in a two dimensional space showing why certain splits in the dendrogram were kept for the fifth cycle of splitting shown in FIG. 10.
Figure 11B:
Figure 11C:
Figure 11D:
Figure 11E:
Figure 11F:
Figure 11G:
Figure 11H:
Figure 11I:
Figure 11J:
Figure 11K:
Figure 11L:
Figure 12A:
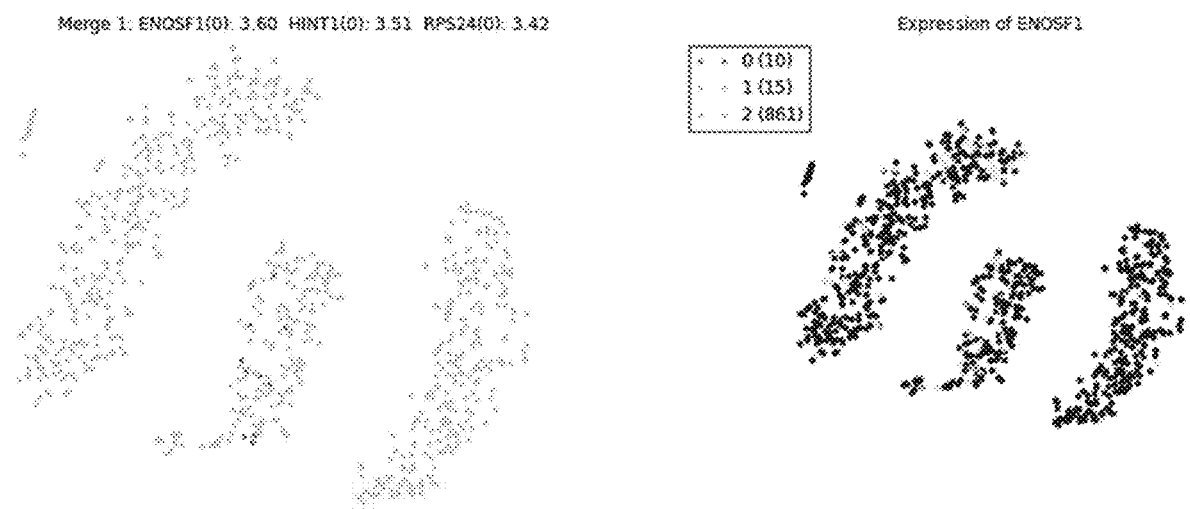
FIGS. 12A-12I are non-limiting exemplary plots of expression profiles in a two dimensional space showing how merges can be decided.
Figure 12B:
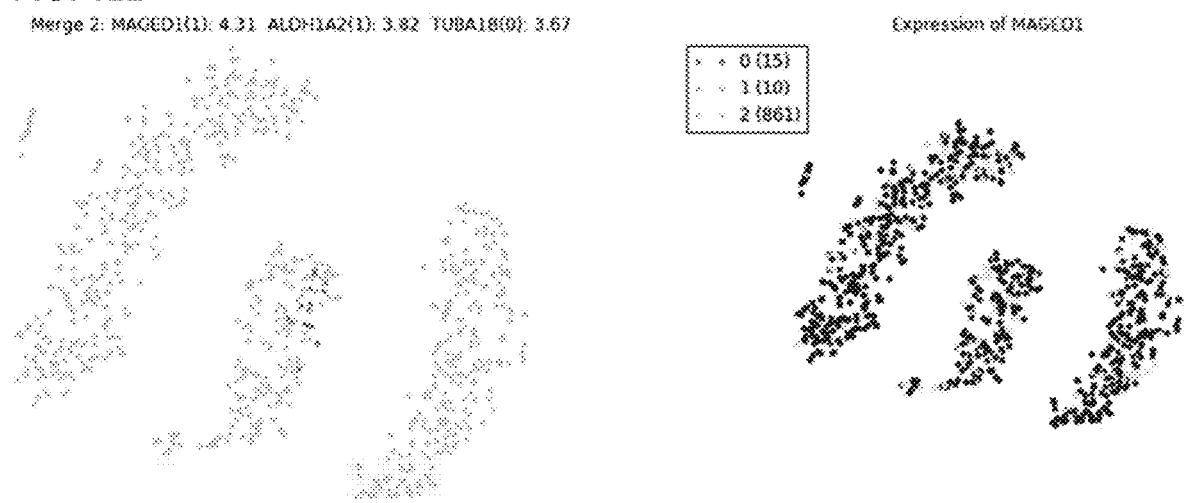
Figure 12C:
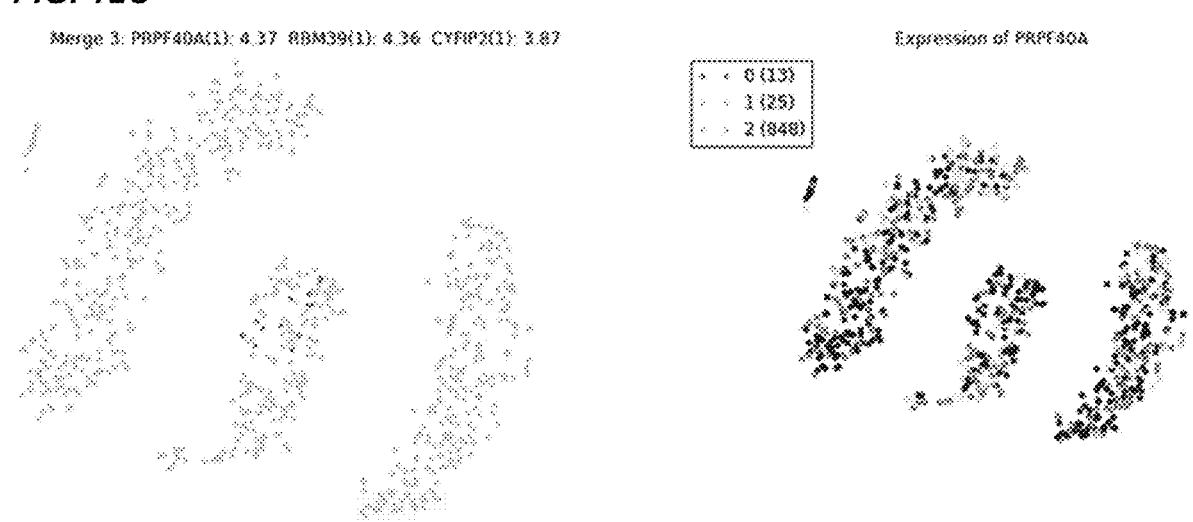
Figure 12D:
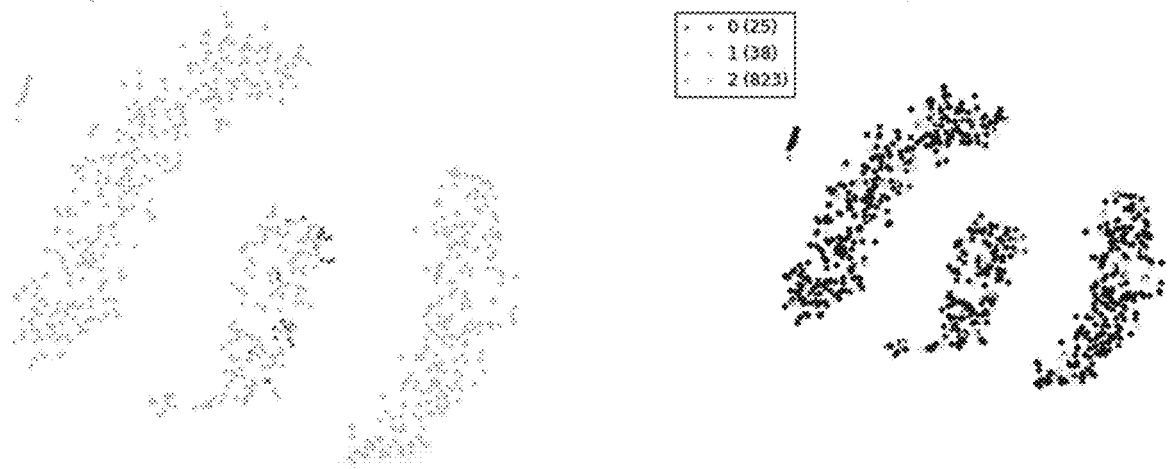
Figure 12E:
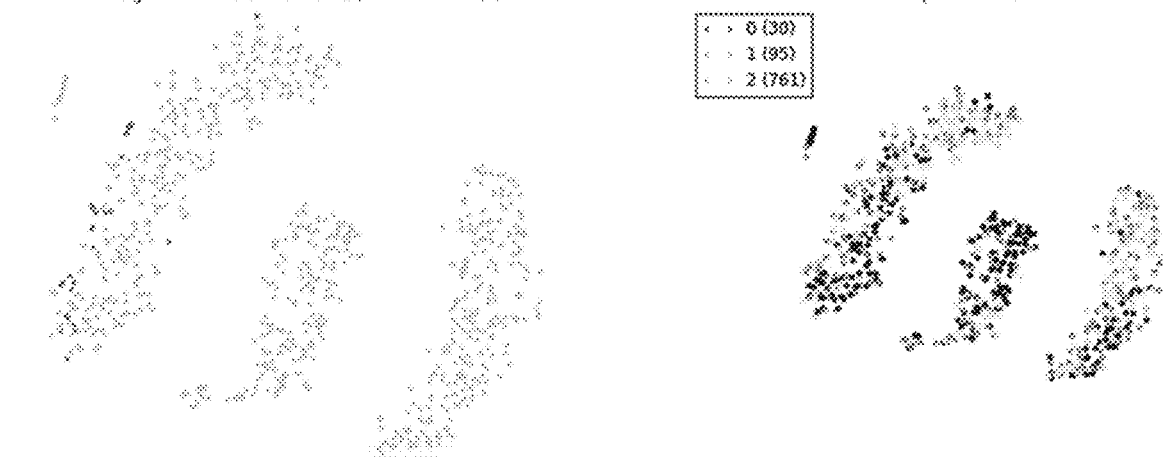
Figure 12F:
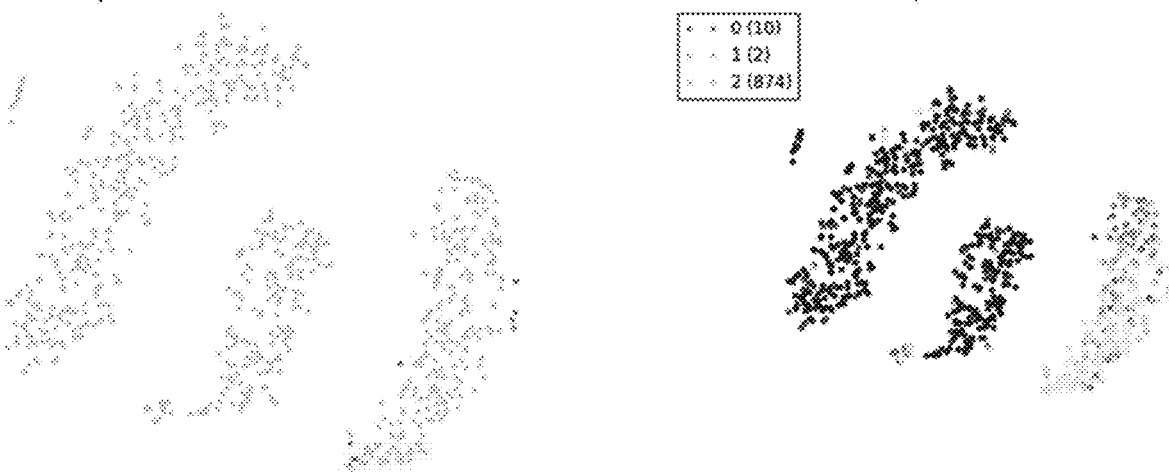
Figure 12G:
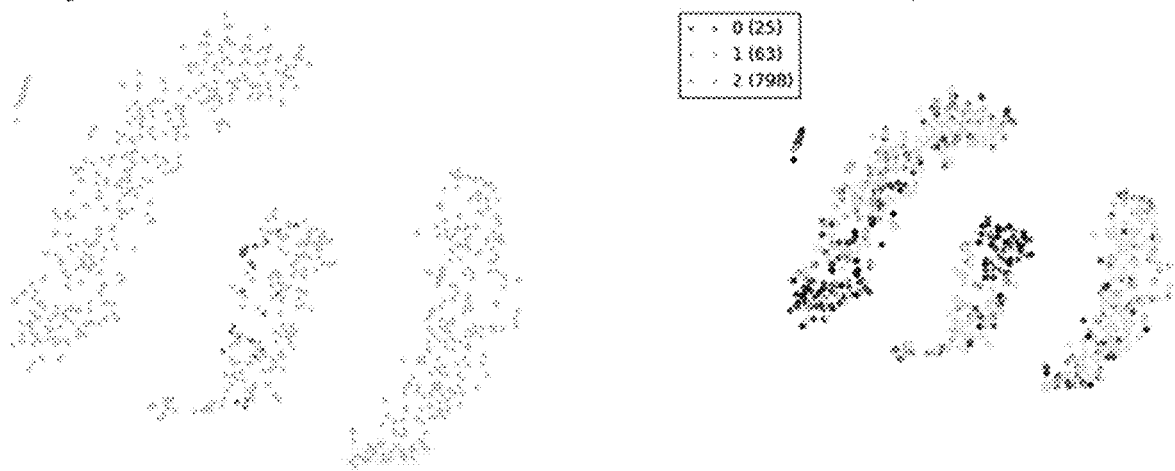
Figure 12H:
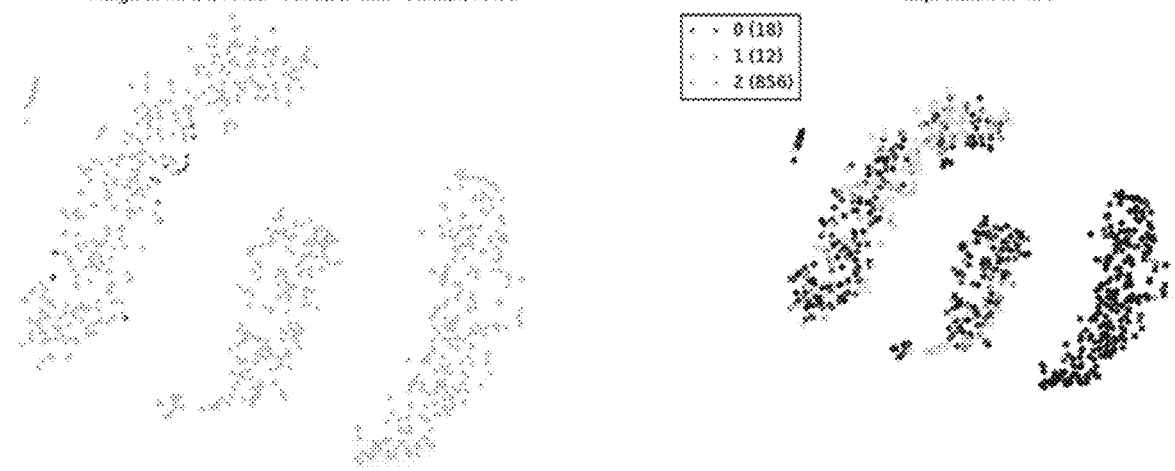
Figure 12I:
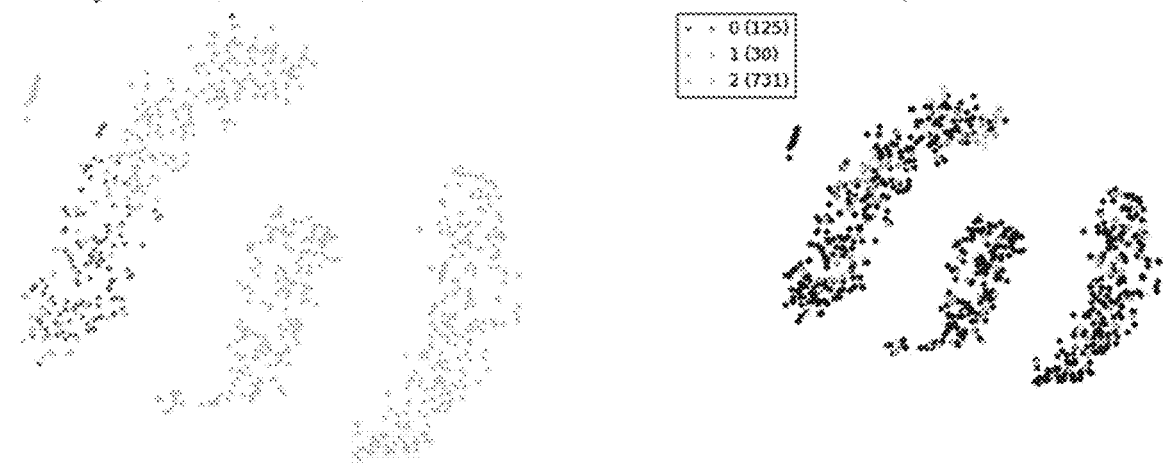

FIG. 10 shows a non-limiting exemplary plot of expression profiles in a two dimensional space after the fifth cycle of splitting. FIGS. 11A-11L are non-limiting exemplary plots of expression profiles in a two dimensional space showing why certain splits in the dendrogram were kept for the fifth cycle of splitting shown in FIG. 10.

Exploring how Merges were Decided

The function for exploring how splits were decided can be used for exploring how merging was performed.

In [10]: split.print_history(genes,mhistory)
split.visualize_history(np.log(1+X),x1,x2,genes,mhistory)
80 of 886 samples are singletons
Singleton(s) 442, 569, 700, 708, 717, 722, 727, 747, 791, 798, 817, 828, 840, 842, 846, 868, 876, 879 m
Singleton(s) 15 merged with cluster 12 (N=24) to form cluster 1 (N=25)
Singleton(s) 3, 4, 6, 7, 9, 10, 11, 13, 14, 19, 20, 21, 22, 24, 25, 26 merged with cluster 18 (N=90)
Singleton(s) 5, 29, 30, 31, 32, 33, 34, 35, 36, 37, 39, 40, 41 merged with cluster 38 (N=261) to form
Singleton(s) 28, 53, 55, 56, 58, 59, 60, 61, 63, 64, 65, 67, 68, 69, 70, 71, 72, 73, 74, 75, 79, 80, 81
Singleton(s) 54, 66 merged with cluster 78 (N=93) to form cluster 13 (N=95)
Post-merge: 25 L: 10 R: 15 Score: 3.60 Top Gene: ENOSF1 Top Gene Score: 3.60
Post-merge: 25 L: 15 R: 10 Score: 4.31 Top Gene: MAGED1 Top Gene Score: 4.31
Post-merge: 38 L: 13 R: 25 Score: 4.37 Top Gene: PRPF40A Top Gene Score: 4.37
Post-merge: 63 L: 25 R: 38 Score: 5.23 Top Gene: ALDOC Top Gene Score: 5.23
Post-merge: 125 L: 30 R: 95 Score: 6.04 Top Gene: PARP1 Top Gene Score: 6.04
Post-merge: 12 L: 10 R: 2 Score: 6.81 Top Gene: IGLC3 Top Gene Score: 6.81
Post-merge: 88 L: 25 R: 63 Score: 7.19 Top Gene: HMGB2 Top Gene Score: 7.19
Post-merge: 30 L: 18 R: 12 Score: 7.23 Top Gene: VIM Top Gene Score: 7.23
Post-merge: 155 L: 125 R: 30 Score: 9.76 Top Gene: HMGN5 Top Gene Score: 9.76

FIGS. 12A-12I are non-limiting exemplary plots of expression profiles in a two dimensional space showing how merges were decided.

In [11]: # Look at merge 2
merge_num=2
cluster_of_interest=None
show_background=False
split.analyze_split(X,x1,x2,genes,mhistory, merge_num, num_genes=4, show_background=show_background,
clust=cluster_of_interest)

Figure 13:
FIG. 13 shows a non-limiting exemplary plot of expression profiles in a two dimensional space after the second cycle of merging.
Figure 15A:
FIGS. 15A-15F are plots showing one non-limiting exemplary type of differential expression analysis.
Figure 15B:
Figure 15C:
Figure 15D:
Figure 15E:
Figure 15F:

FIG. 13 shows a non-limiting exemplary plot of expression profiles in a two dimensional space after the second cycle of merging. FIGS. 14A-14D are non-limiting exemplary plots of expression profiles in a two dimensional space showing how the second cycle of merges shown in FIG. 13 was decided.

Differential Expression

The module allows for two kinds of simple differential expression analysis. The first does a one-v-rest comparison for each cluster, visualizing the most important genes for each cluster according to a t-test for each gene. The second does a pairwise comparison for every two pairs of clusters.

In [12]:
split.save_more_highly_expressed_genes_in_one_clust(X, genes,ym,x1,x2,num_genes=3, show_plots=True)

FIGS. 15A-15F are plots showing one non-limiting exemplary type of differential expression analysis.

Figure 16A:
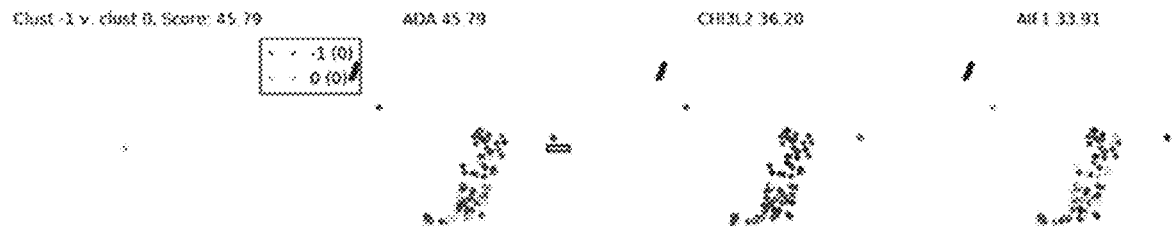
FIGS. 16A-16O are plots showing another non-limiting exemplary type of differential expression analysis.
Figure 16B:
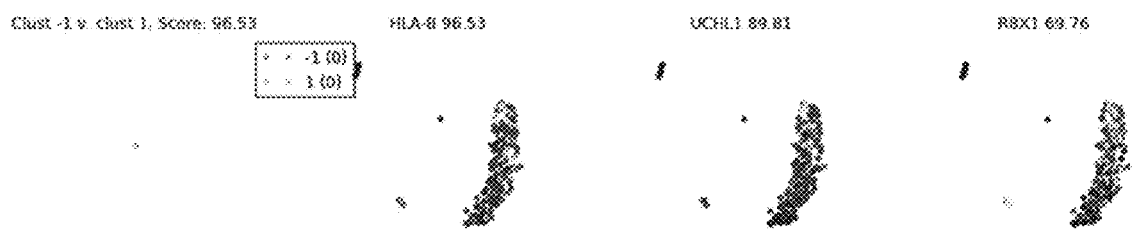
Figure 16C:
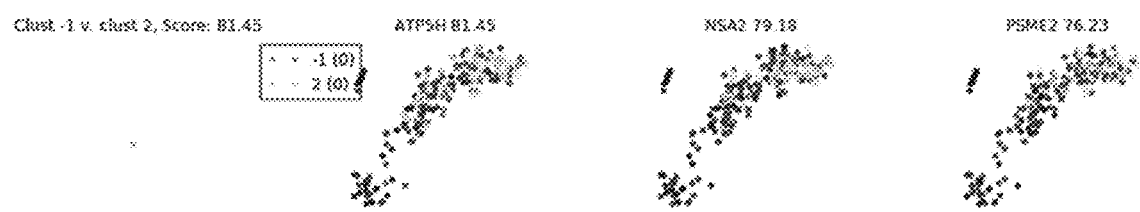
Figure 16D:
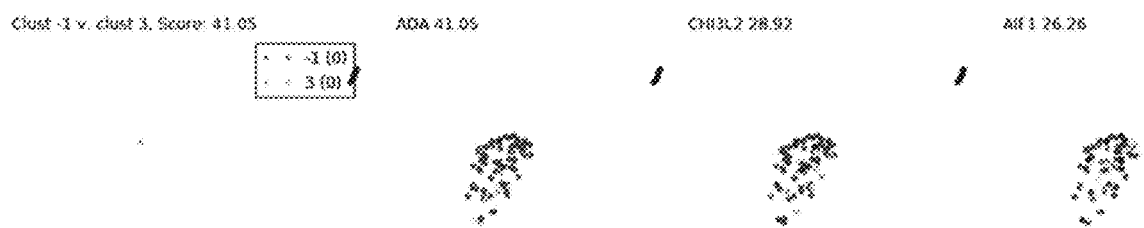
Figure 16E:
Figure 16F:
Figure 16G:
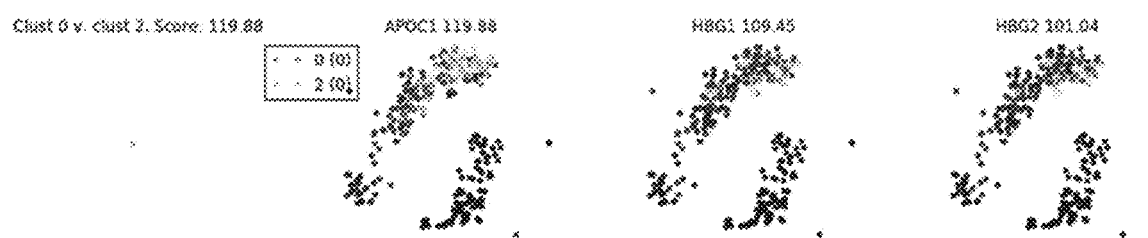
Figure 16H:
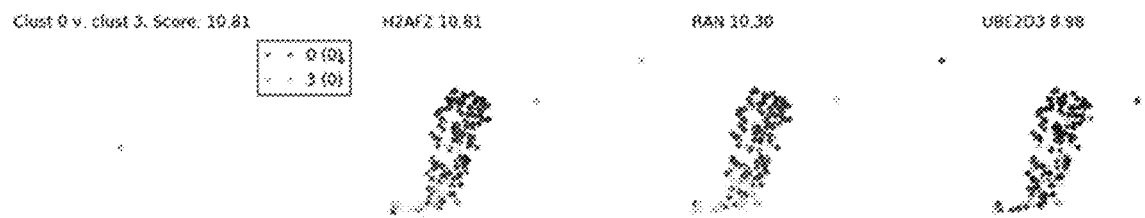
Figure 16I:
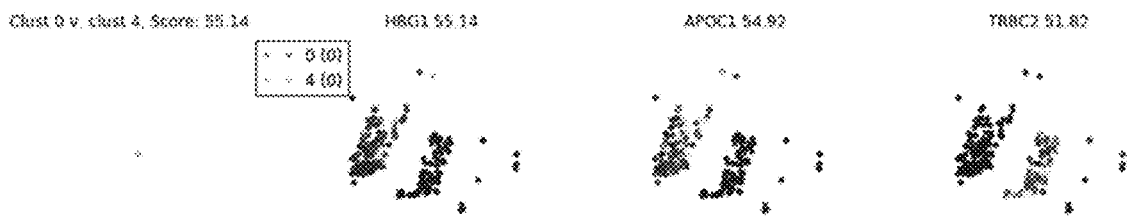
Figure 16J:
Figure 16K:
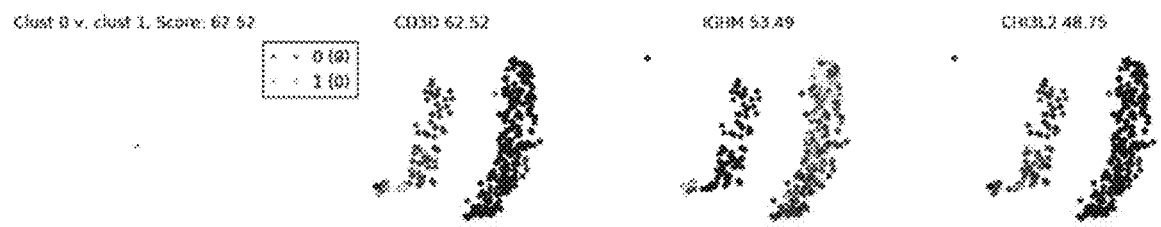
Figure 16L:
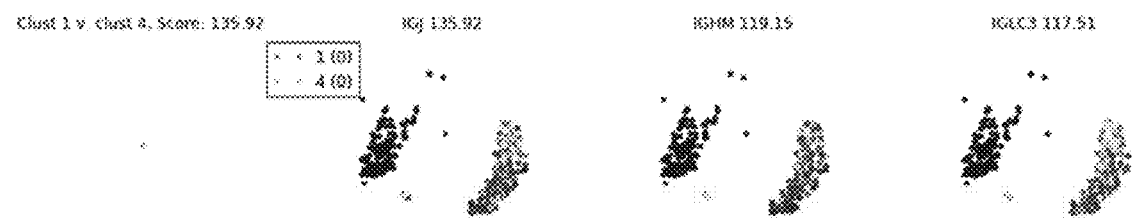
Figure 16M:
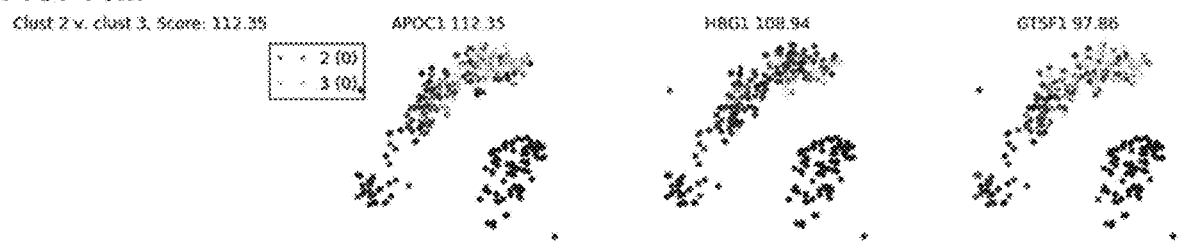
Figure 16N:
Figure 16O:
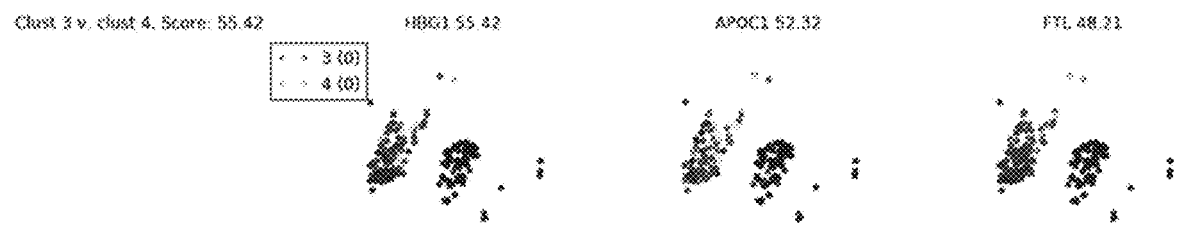
Figure 18A:
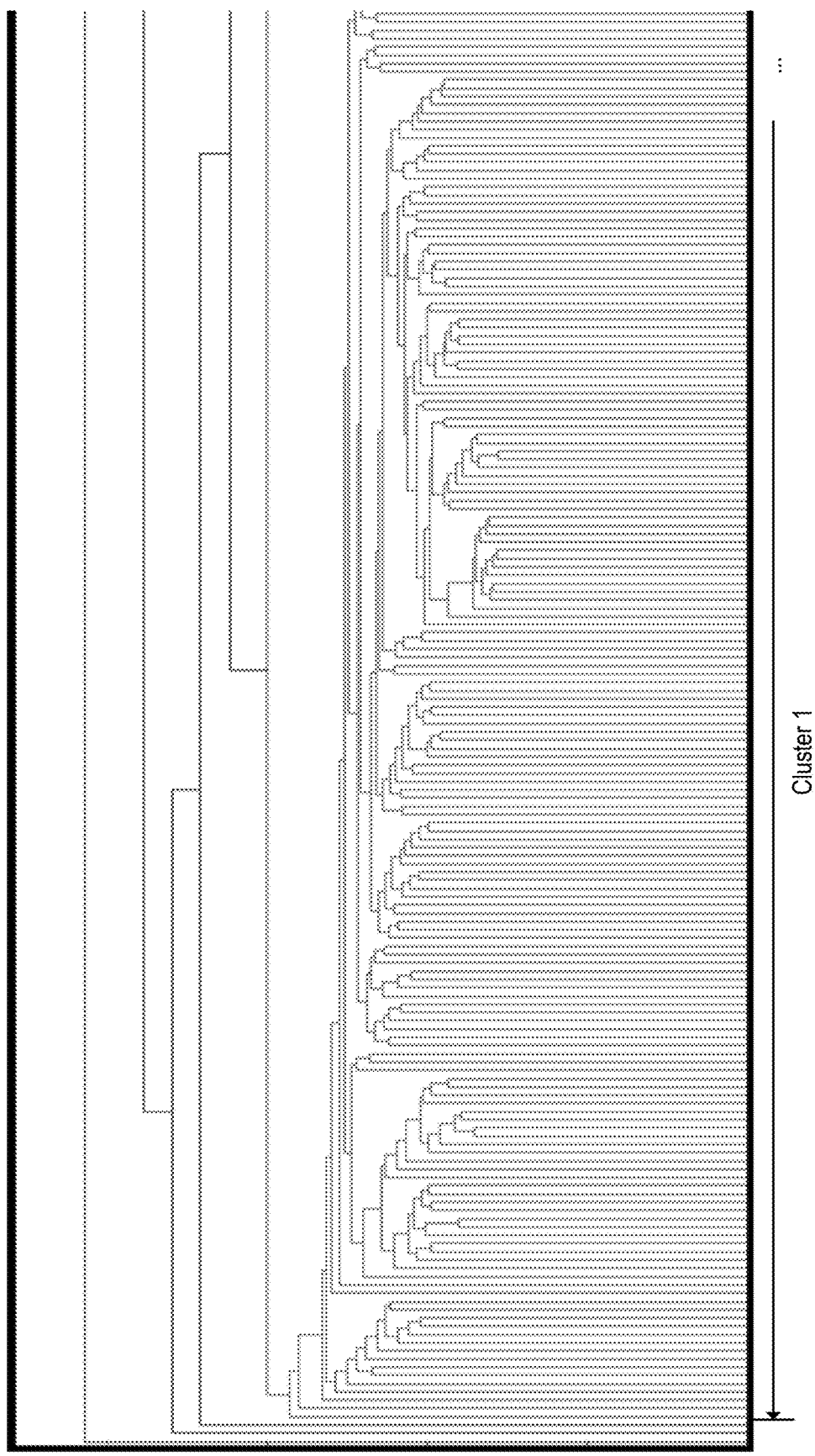
Figure 18B:
Figure 18C:
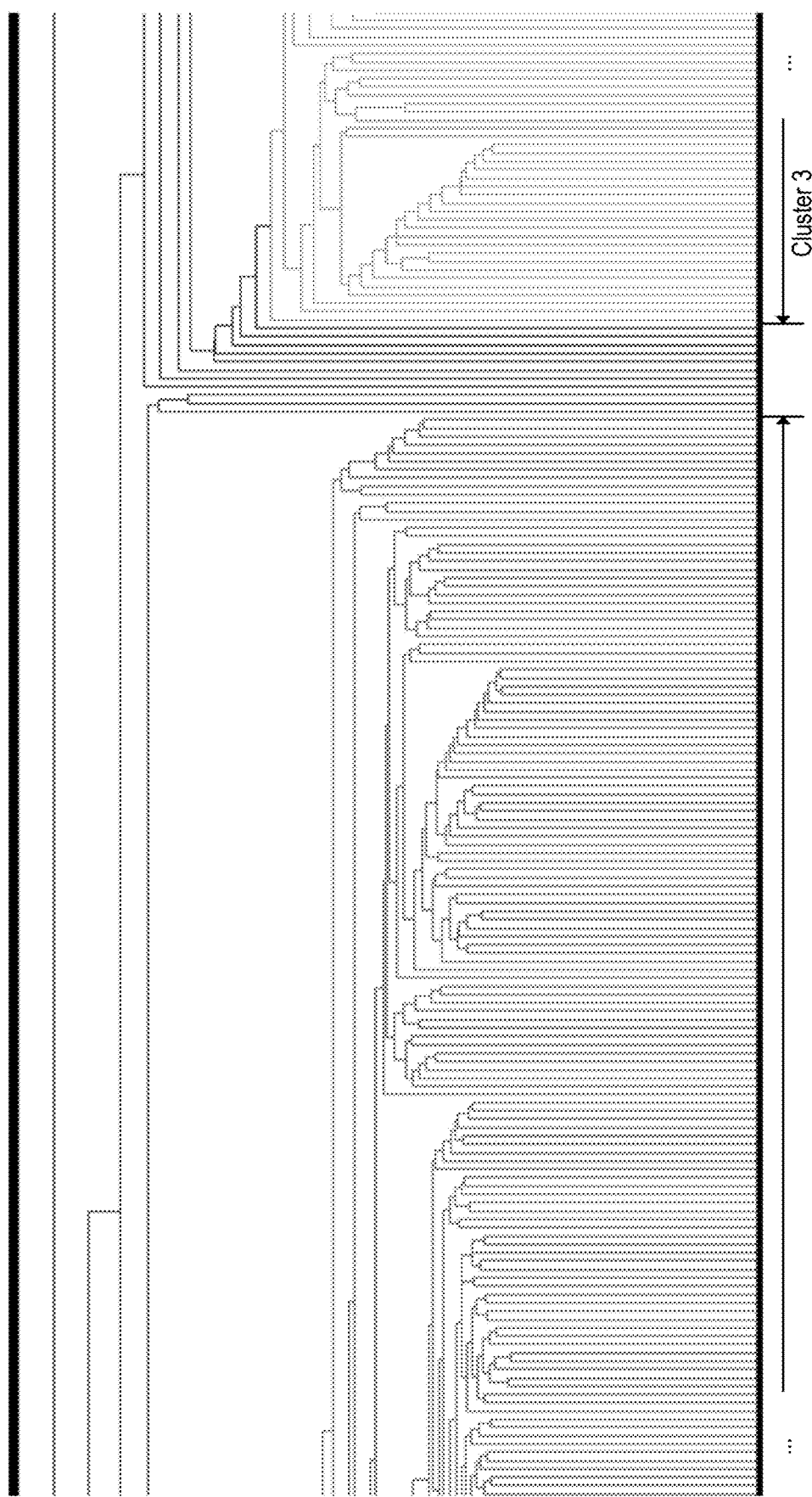
Figure 18D:
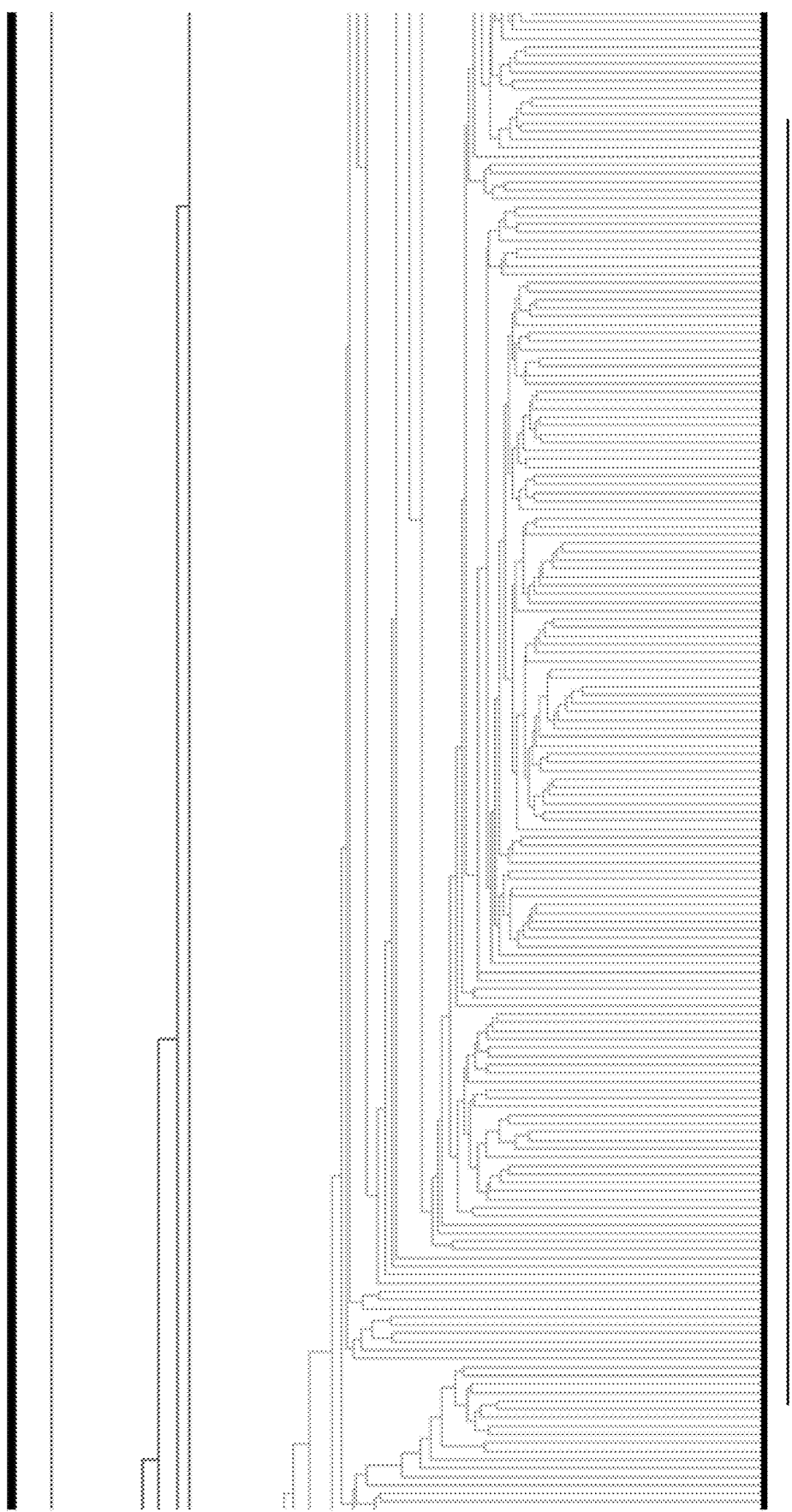
Figure 18E:
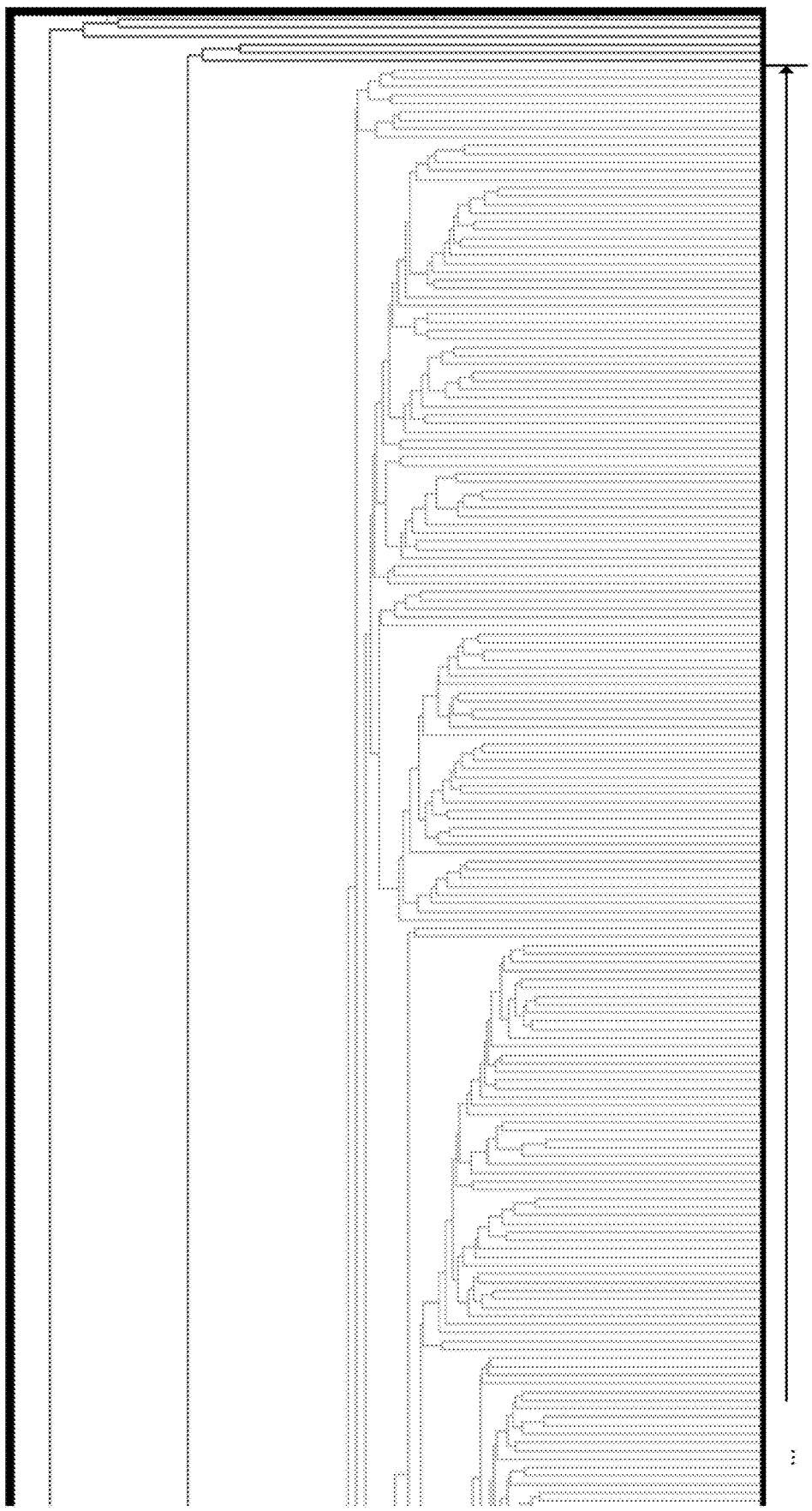

In [13]: split.pairwise_cluster_comparison(X,genes,ym, x1=x1,x2=x2, num_genes=3, show_plots=True,verbose=F
dendrosplit/utils.py:39: FutureWarning: elementwise comparison failed; returning scalar instead, but in plt.plot(x1 [y==i],x2[y==i],'.',c=RGBs[j],label=str(i)+'('+str(np. sum (y==i))+')') dendrosplit/feature selection.py:221: RuntimeWarning: divide by zero encountered in double scalars fold=g mean j/g mean i FIGS. 16A-16O are plots showing another non-limiting exemplary type of differential expression analysis.

Distance Distribution

The module also allows the user to visualize the distribution of distances within each cluster. For a given cluster, this function plots the proportion of pairwise distances (between points in the cluster) for each percentile bin of the overall set of pairwise distances (for all points in all clusters). For example, 0.3 at 1 indicates that 30% of the pairwise distances fall between the 5th and 10th percentiles of overall distances. Use this function gain a sense of how cohesive clusters are according to the original distance matrix. Intuitively, a good cluster should have points that are all close to one another. For example, a cluster with no distances in the bottom 10 bins (i.e. bottom 50 percentile) would be considered bad. Notice that as expected this is the case for cluster "−1" below, which contains the outliers.

In [14]: merge.visualize_within_cluster_distance_distributions(D, ym, show_D_dist=True)

FIGS. 17A-17G are non-limiting exemplary plots visualizing the distances between clusters.

Dendrogram

The module also allows users to generate a dendrogram and obtain the order of the cells according to the dendrogram. The dendrogram may be hard to view in an iPython notebook. In some embodiments, the dendrogram can be saved, as shown below. Users can feed in the cluster labels ("labels" keyword). If desired, the function can color the names of all samples within a cluster the same color.

In [15]: cell_order=split.plot_dendro(D, return_cell_order=True, labels=ym, save_name='/Users/user1/Desktop/dendrogram') dendrosplit/split.py:233: FutureWarning: comparison to 'None' will result in an elementwise object comp if labels !=None:

FIGS. 18 and 18A-18E show a non-limiting exemplary dendrogram.

Altogether, these data demonstrate the various tools of the disclosure for visualizing the various steps and results of recursive splitting and merging followed by merging.

Example 3

Parameter Sweeping for Clustering by Recursive Dendrogram Splitting and Testing Followed by Merging This example describes parameter sweeping for optimizing parameters for recursive splitting and testing followed by merging.

During the splitting step of the method, two hyperparameters can be tuned: score threshold and disband percentile. What different clusters can be generated with different hyperparameters can be explored. Several (post-split pre-merge) clustering results can be obtained rapidly by exploiting the fact that the clusters generated with a smaller score threshold (smaller threshold results in more clusters) partition the clusters generated with a larger score threshold. First, run the splitting step with a very low threshold. Second, use the get clusters from history( ) function.

An example for sweeping through various score threshold values is shown below. The same can be done with disband percentile values.

In [16]: ys,shistory=split.dendrosplit((D,X), preprocessing='precomputed',
score_threshold=2, verbose=False, disband_percentile=50) ys_sweep=[ ]
thresholds=range(5,100,5)
for threshold in thresholds:
ys_sweep.append(split.get_clusters_from_history(D,shistory,threshold,50)) plt.figure( )
split.plot_labels_legend(x1,x2,split.str_labels_to_ints(ys_sweep[−1]))
plt.title('Clustering result using a threshold of %.3f'% (threshold))

Figure 19A:
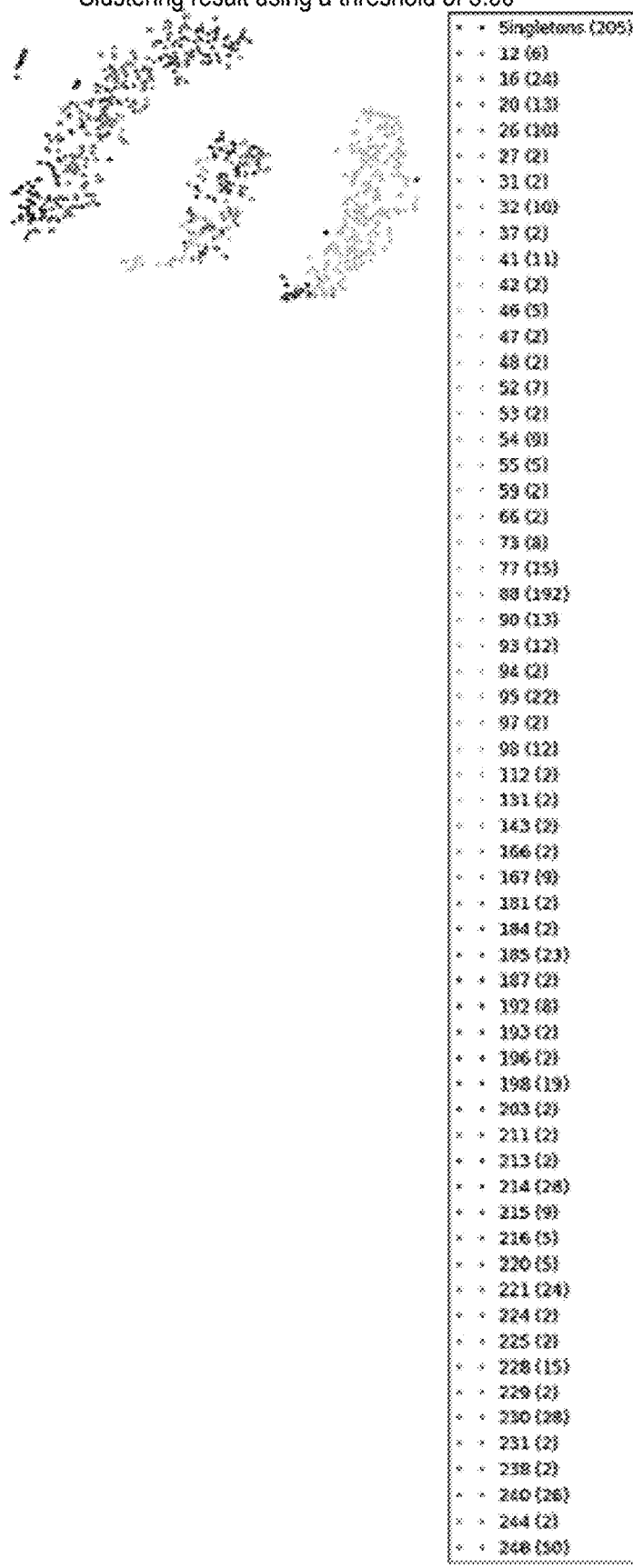
FIGS. 19A-19S are non-limiting exemplary plots showing parameter sweeping.
Figure 19B:
Figure 19C:
Figure 19D:
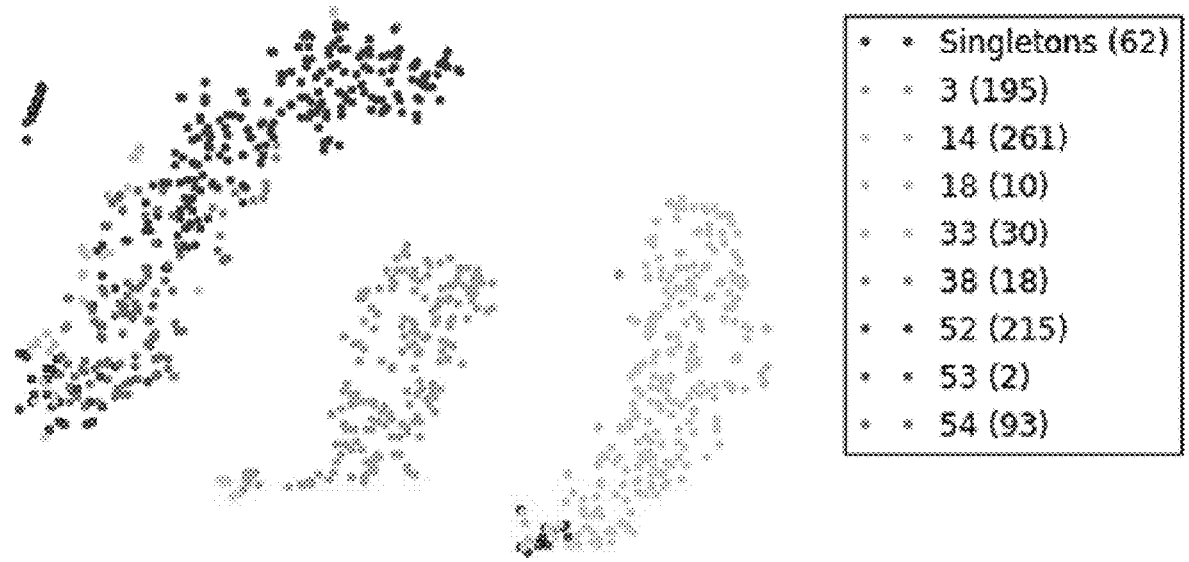
Figure 19E:
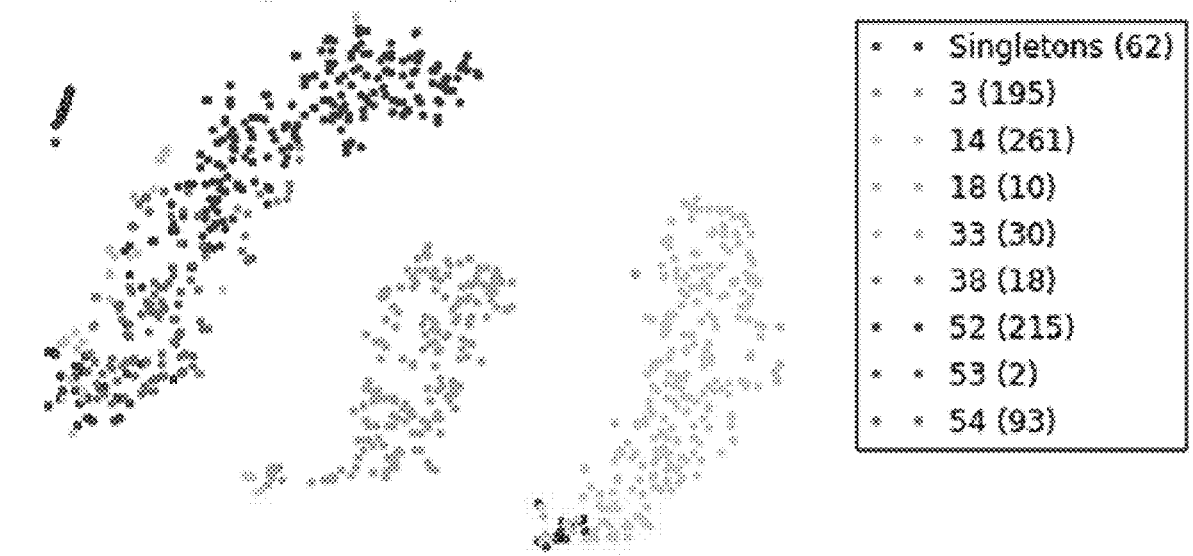
Figure 19F:
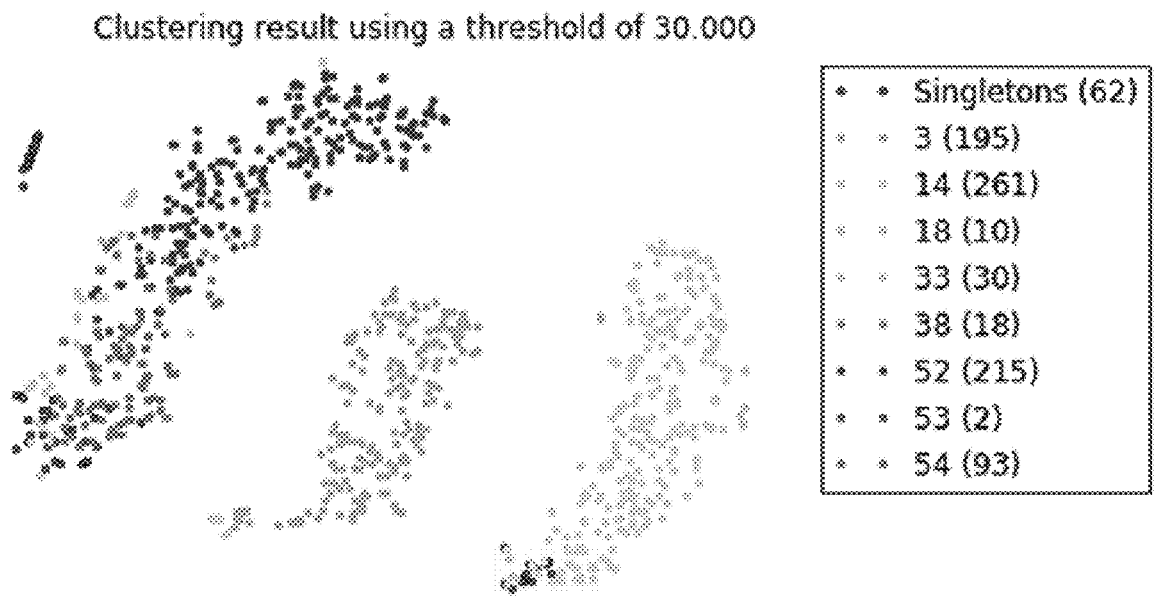
Figure 19G:
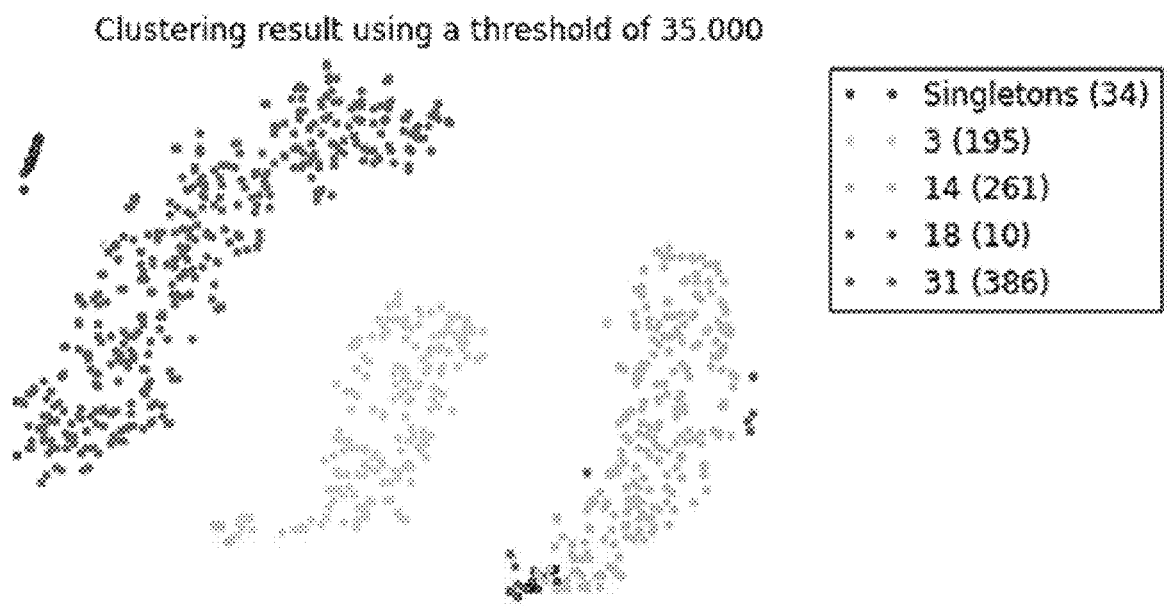
Figure 19H:
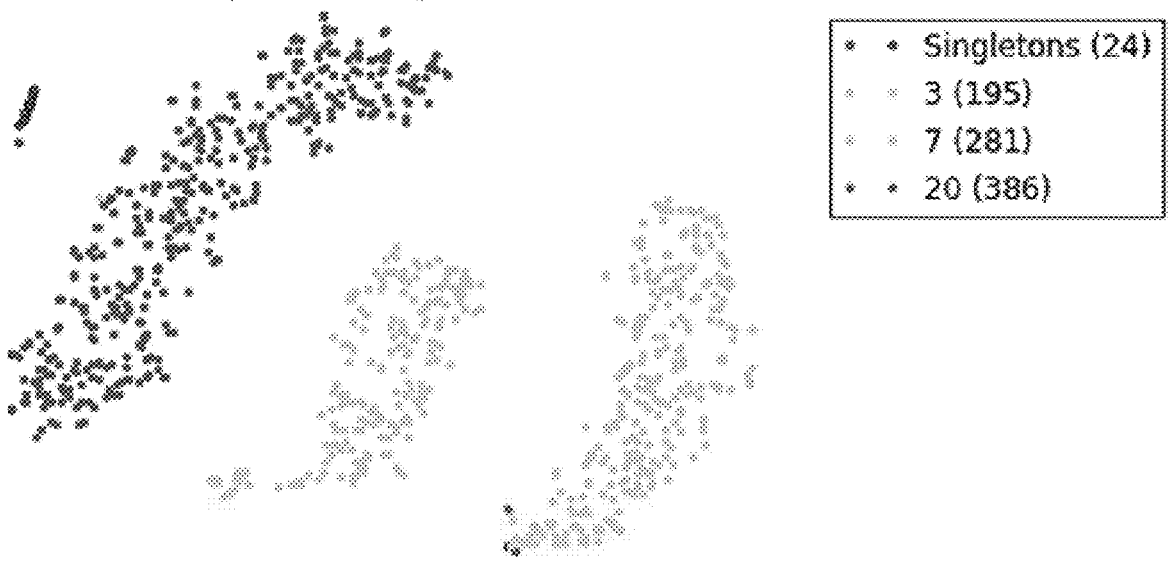
Figure 19I:
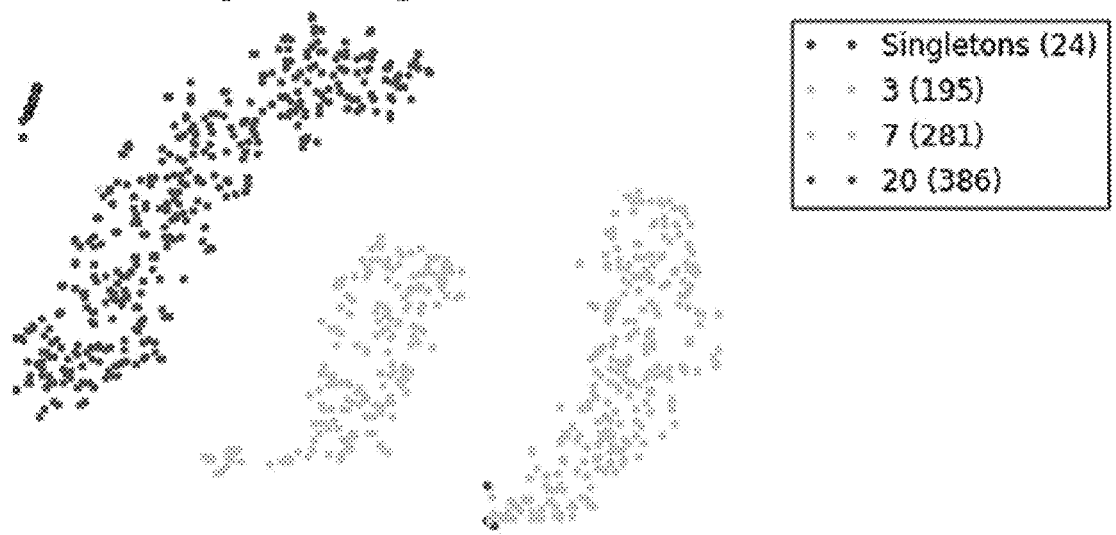
Figure 19J:
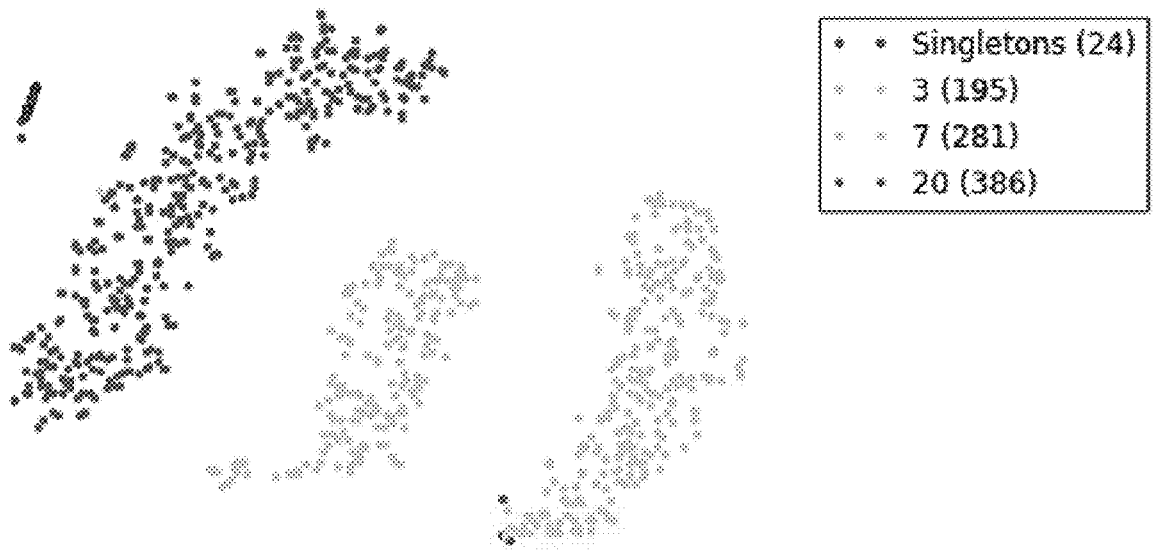
Figure 19K:
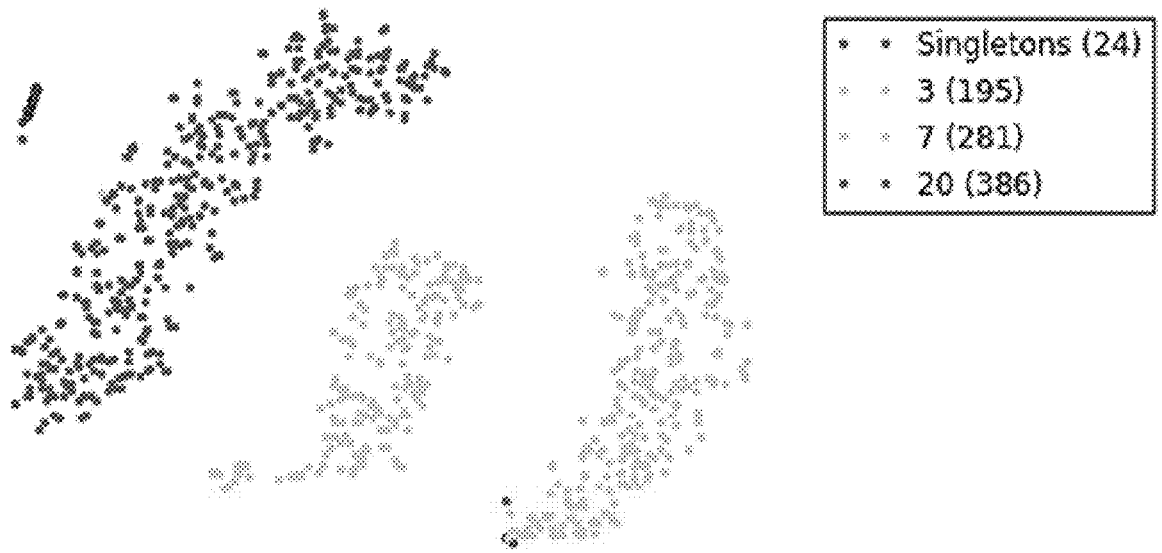
Figure 19L:
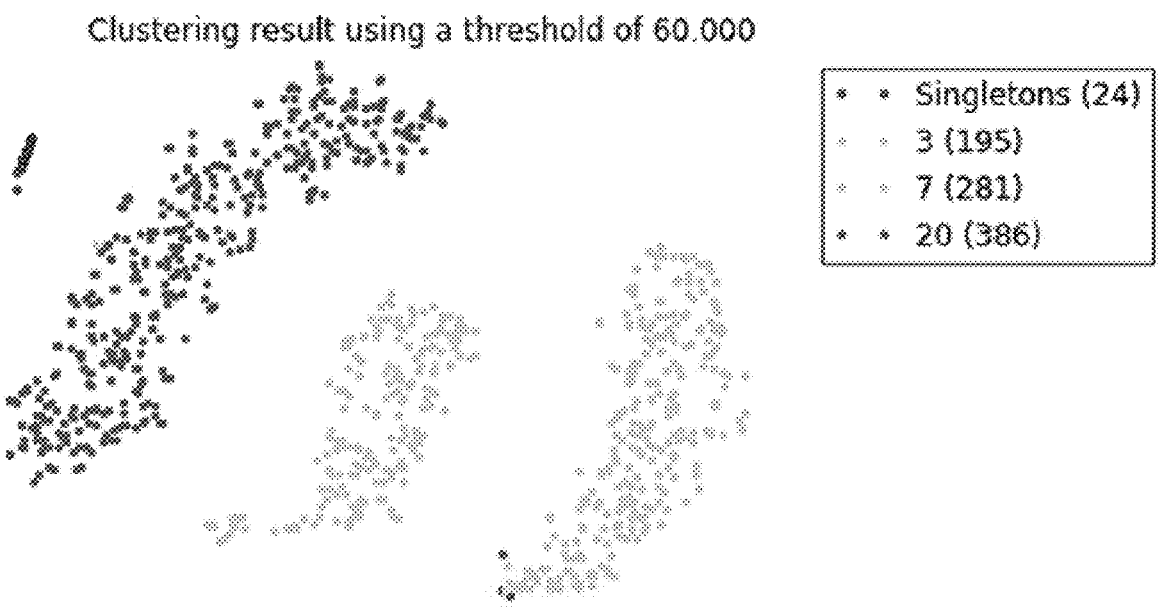
Figure 19M:
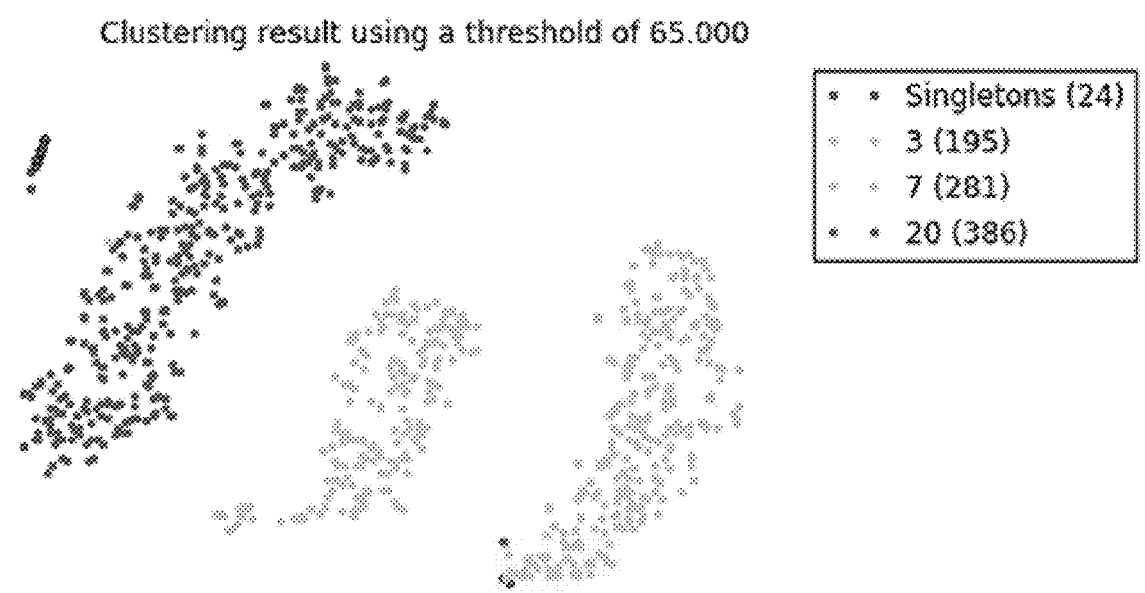
Figure 19N:
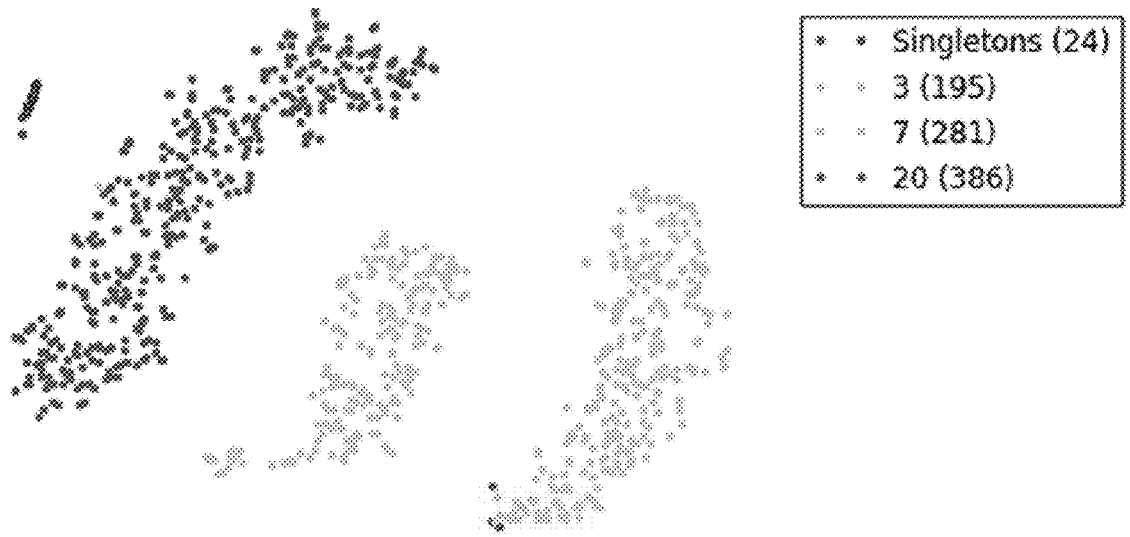
Figure 19O:
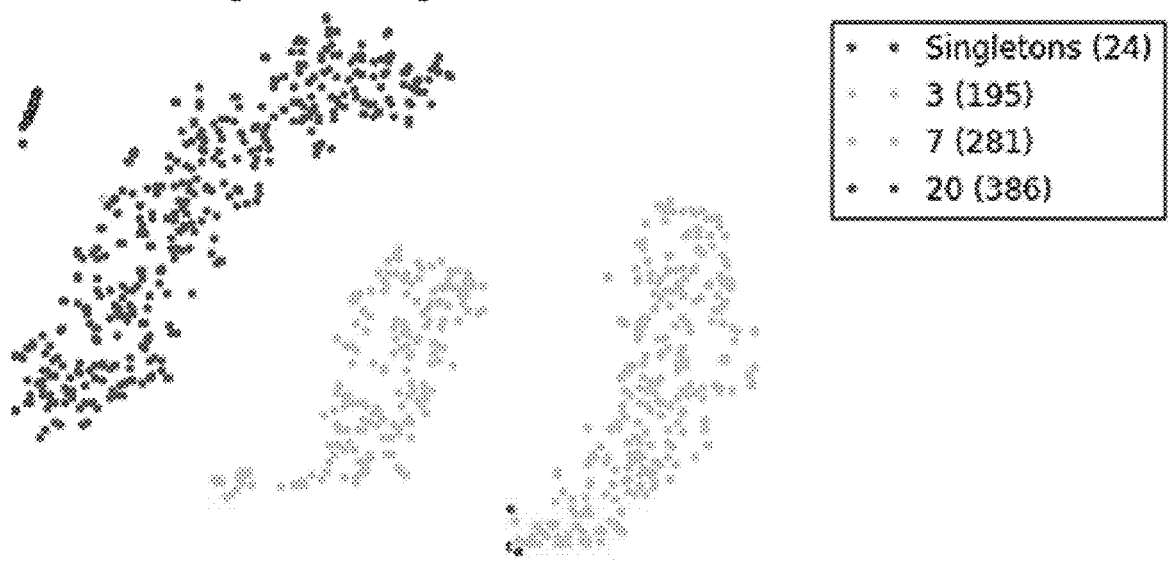
Figure 19P:
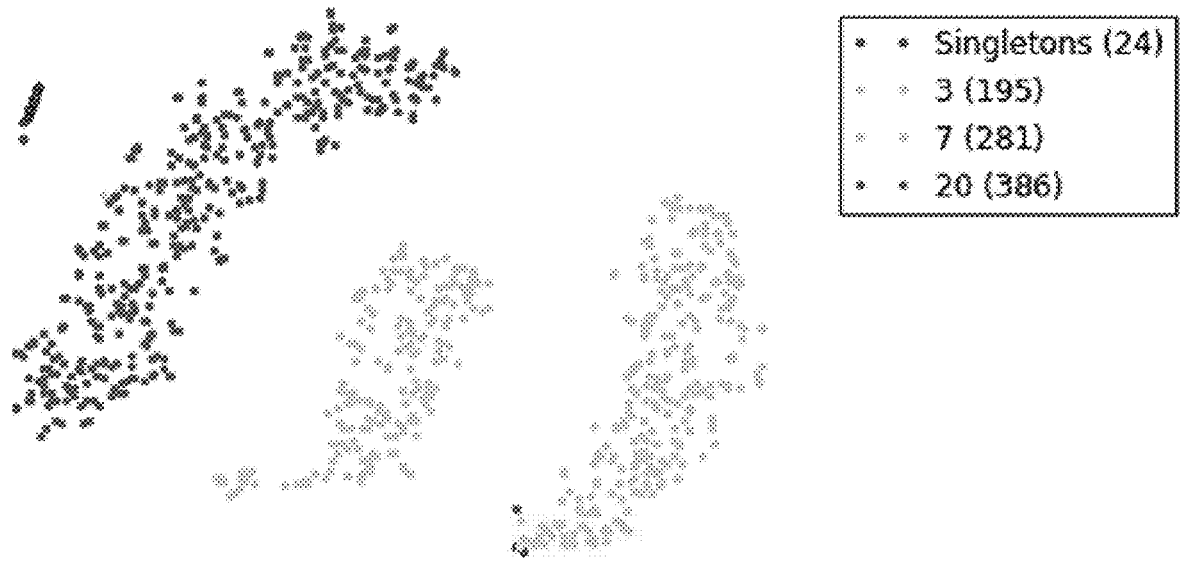
Figure 19Q:
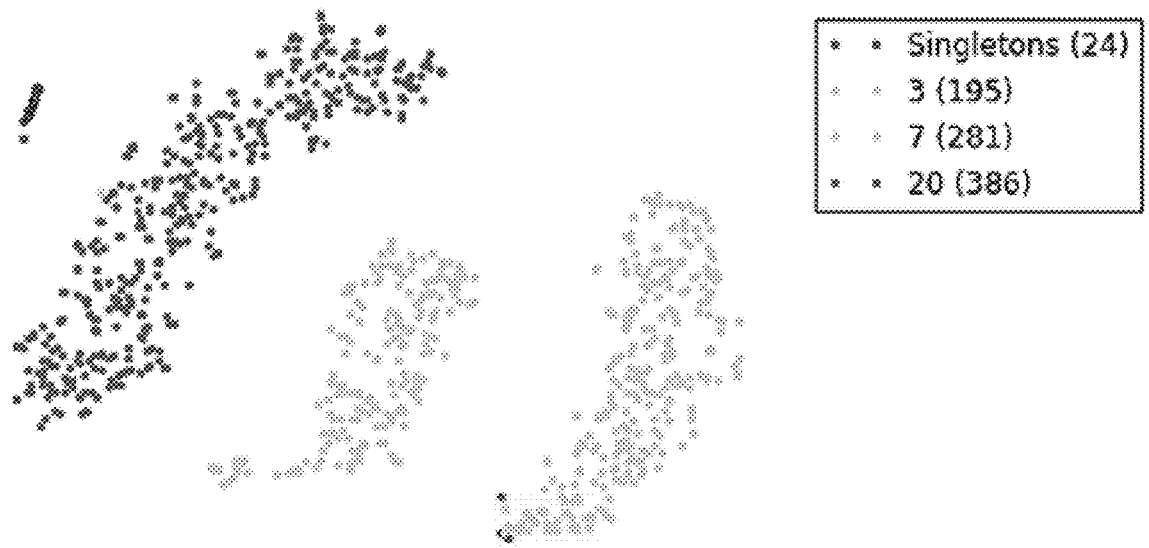
Figure 19R:
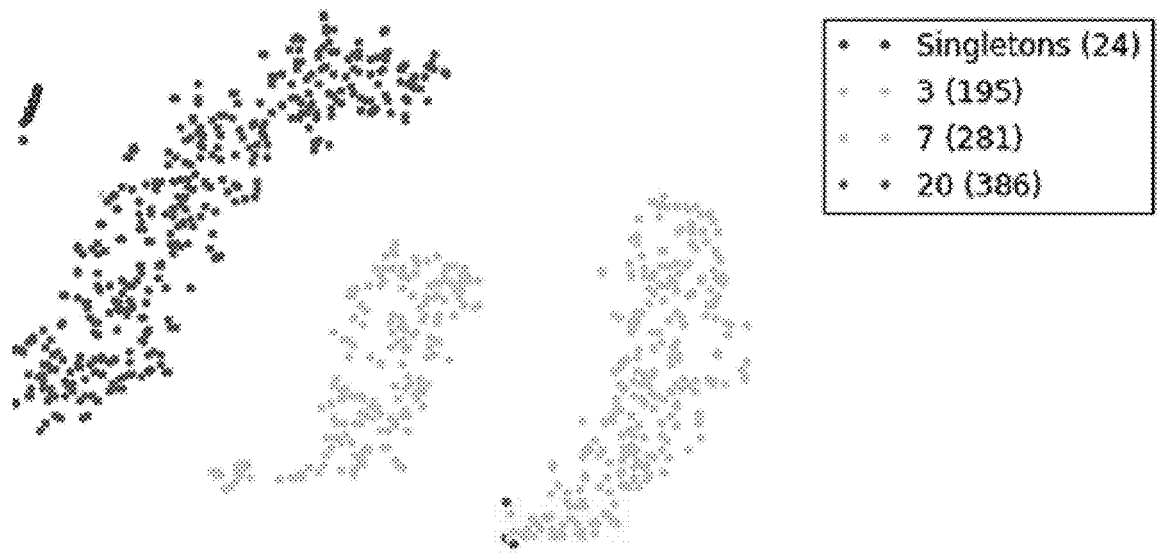
Figure 19S:
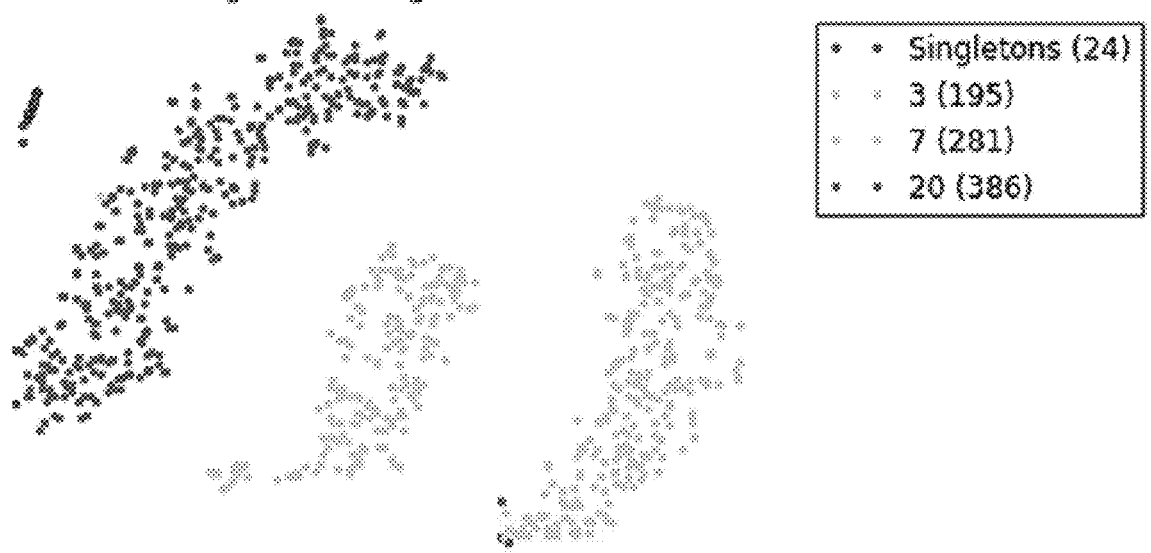

FIGS. 19A-19S are non-limiting exemplary plots showing parameter sweeping.

By sweeping parameters, how the number of clusters changes as a function of the threshold can be investigated. This may give users insights on how to select an optimal threshold for a particular application.

In [17]: def count_nonsingleton_clusters(y):
return sum([1 for i in np.unique(y) if np.sum(y==i) !=1])
plt.plot(thresholds,[count_nonsingleton_clusters(i) for i in ys_sweep]) plt.grid( )
plt.xlabel('thresholds (−log 10(p-value))')
plt.ylabel('number of nonsingletone clusters')
Out[17]: <matplotlib.text.Text at 0x117fb3290>

Figure 20:
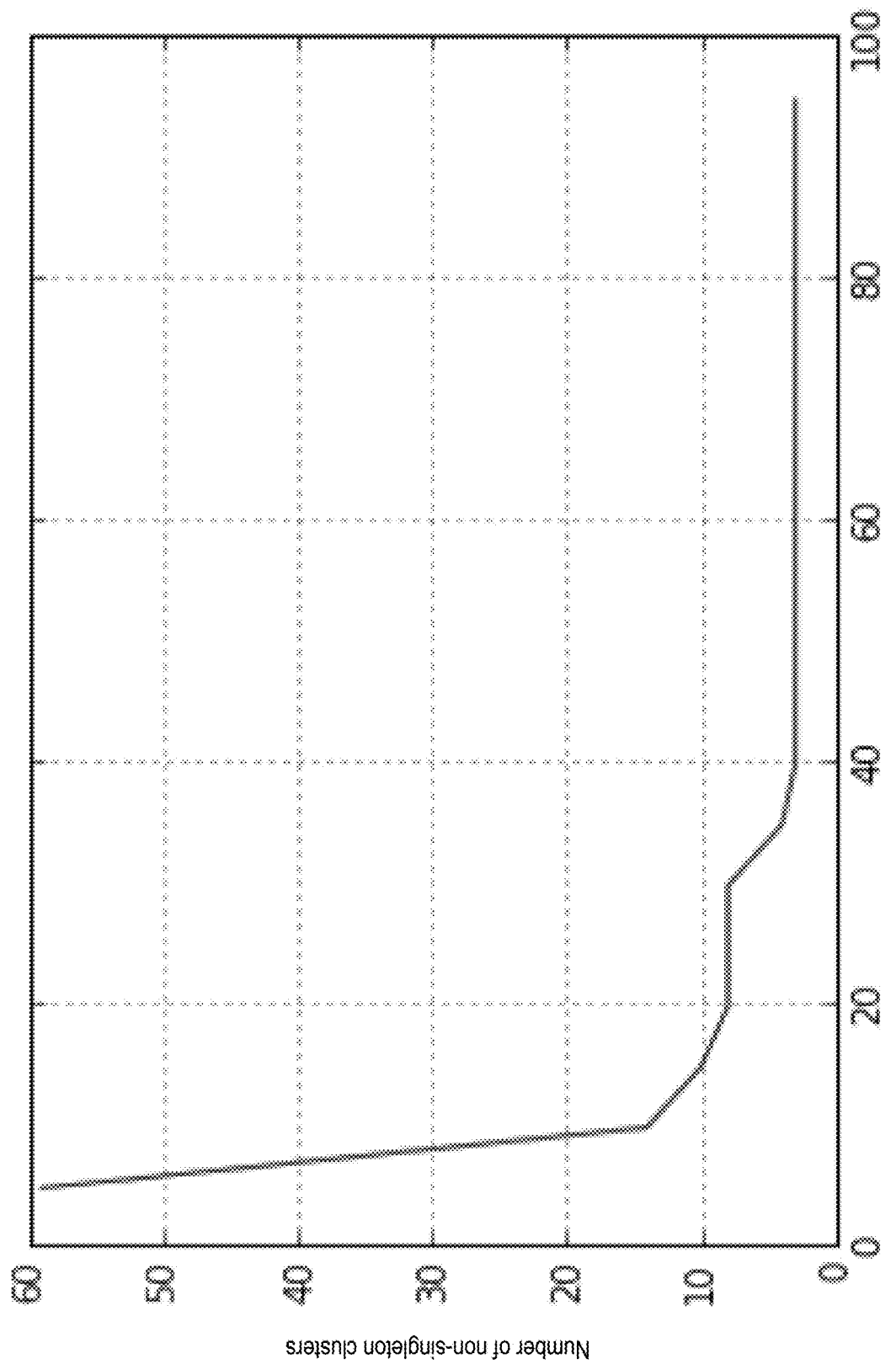
FIG. 20 is a non-limiting exemplary plot showing how parameter sweeping can be used to identify a threshold.
Figure 21E:
Figure 21F:
Figure 21G:
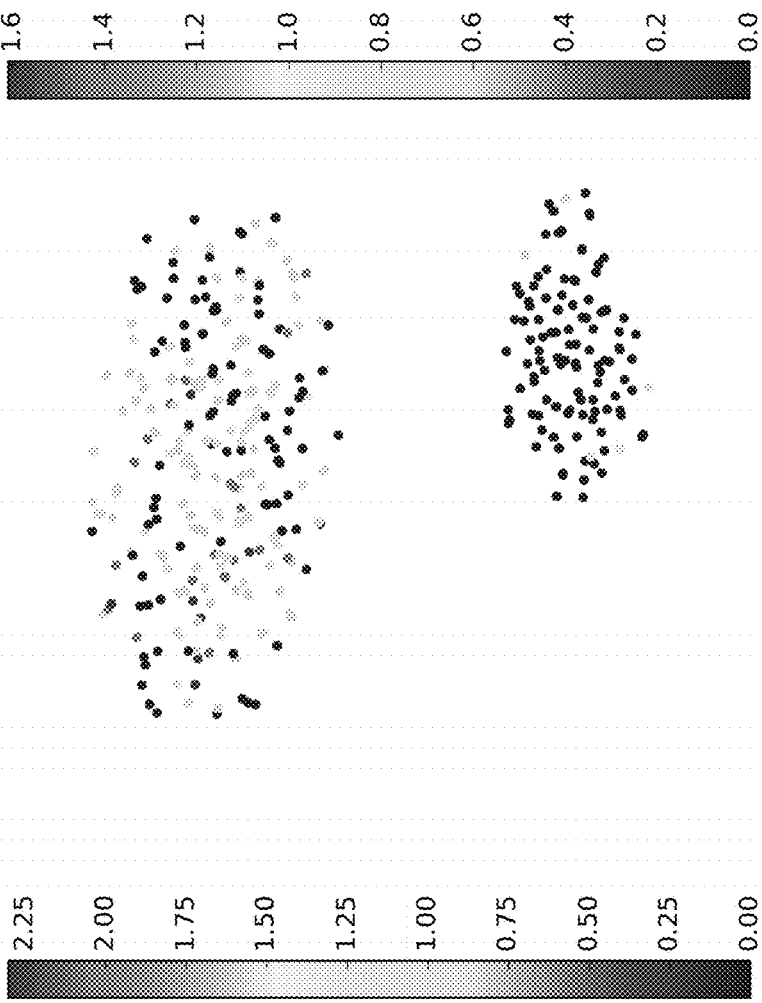
Figure 21H:
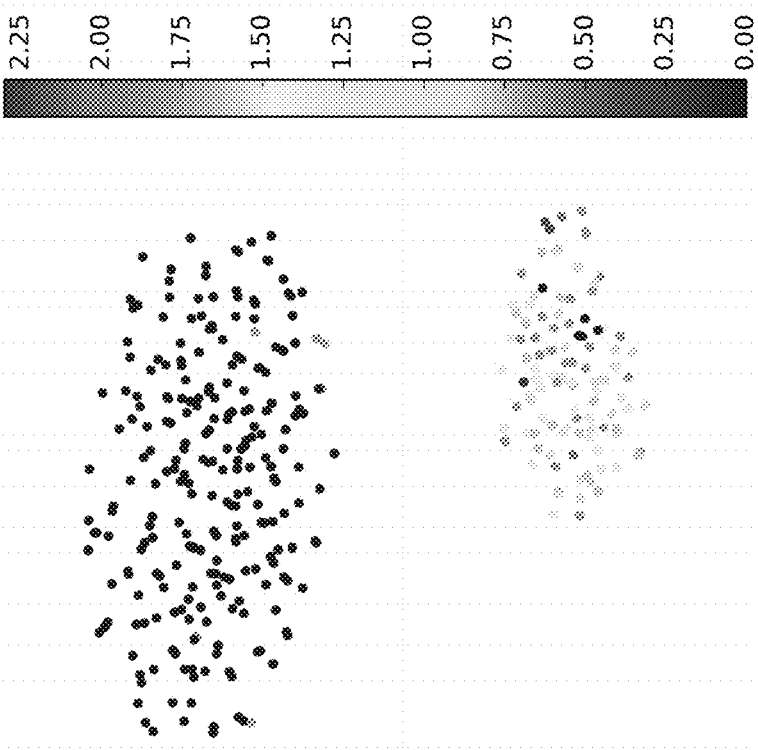
Figure 21J:
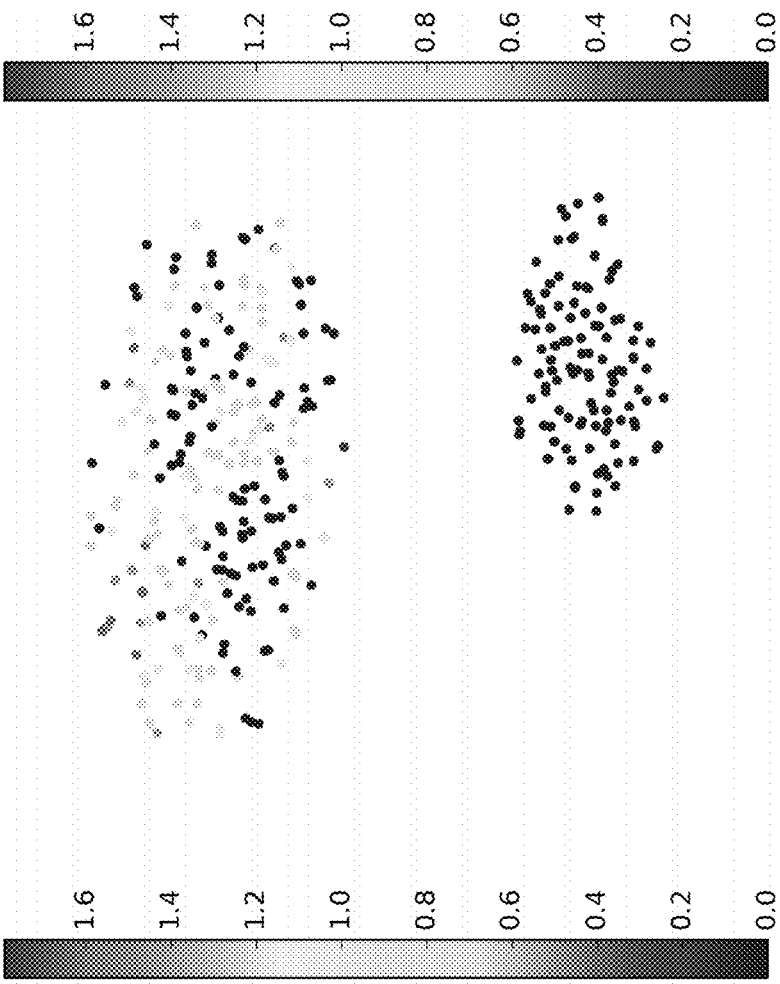
Figure 21I:
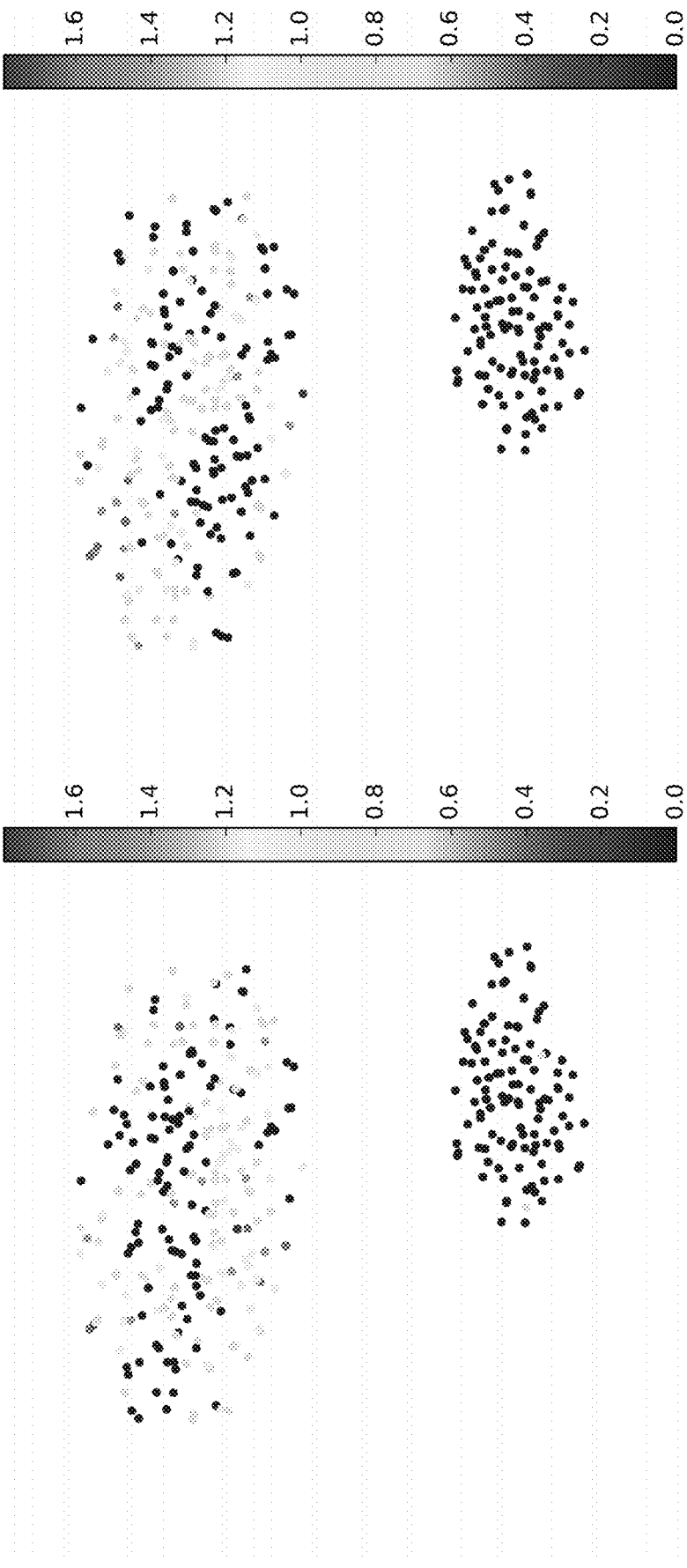

FIG. 20 is a non-limiting exemplary plot showing how parameter sweeping can be used to identify a threshold. Because a large number of clusters of expression profiles were identified with a threshold of only 5, fewer clusters of expression profiles were identified with larger thresholds (e.g., 40 shown in FIG. 19H).

Altogether, these data demonstrate optimizing hyperparameters by parameter sweeping for recursive splitting and testing followed by merging.

Example 4

Clustering by Recursive Dendrogram Splitting and Testing Followed by Merging

This example describes a clustering method by recursive splitting (e.g., recursive dendrogram splitting) and testing followed by merging. At each cluster or node of the dendrogram (except for the leaf nodes), the intra-cluster median correlation of the two sub-clusters was higher than the inter-cluster median correlation in this example.

During the splitting and testing phase of the expression profiles of 357 cells, starting from the top of the dendrogram, the tree was split into two candidate subtrees. The split corresponded to a cluster being split into two candidate sub-clusters, under the constraint that the intra-cluster median correlation of the two sub-clusters should be higher than the inter-cluster median correlation. The quality of the split was scored. If the subclusters were deemed to be sufficiently different, the phase continued to each subtree. If not, the method terminated for this portion of the dendrogram. This phase produced a set of labels for the dataset.

FIGS. 21A-21J are non-limiting exemplary plots showing the results of the first split. During the first split, twenty genes (shown in Table 1) were determined to be expressed different in the 357 cells.

TABLE 1

Twenty genes were determined to be expressed differently in the 357 cells during the first split.

| Split | Gene | p-Value | Larger Cluster |
|---|---|---|---|
| 1 | IGLC3\|ENST00000390325.2\|Reference__end | 201.35 | 0 |
| 1 | JCHAIN\|NM__144646.3\|Reference__end | 105.57 | 0 |
| 1 | ADA\|NM__000022.3\|Reference__end | 89.27 | 1 |
| 1 | TCL1A\|NM__021966.2\|Reference__end | 81.19 | 0 |
| 1 | CD74\|NM__004355.3\|Reference__end | 62.65 | 0 |
| 1 | CD3D\|NM__000732.4\|Reference__end | 50.32 | 1 |
| 1 | POU2AF1\|NM__006235.2\|Reference__end | 39.94 | 0 |
| 1 | CD52\|NM__001803.2\|Reference__end | 39.1 | 0 |
| 1 | QPCT\|NM__012413.3\|Reference__end | 38.87 | 0 |
| 1 | HLA-DRA\|NM__019111.4\|Reference__end | 26.64 | 0 |
| 1 | CD22\|NM__001771.3\|Reference__end | 25.96 | 0 |
| 1 | IRF8\|NM__002163.2\|Reference__end | 21.25 | 0 |
| 1 | MS4A1\|NM__021950.3\|PolyA__1 | 19.99 | 0 |
| 1 | CD37\|NM__001774.2\|Reference__end | 18.49 | 0 |
| 1 | LEF1\|NM__016269.4\|Reference__end | 17.63 | 1 |
| 1 | MME\|NM__000902.3\|Reference__end | 15.59 | 0 |
| 1 | BCL6\|NM__001706.4\|Reference__end | 13.39 | 0 |
| 1 | CD27\|NM__001242.4\|Reference__end | 11.02 | 0 |
| 1 | IL32\|NM__004221.4\|Reference__end | 10.86 | 1 |
| 1 | CD38\|NM__001775.3\|Reference__end | 10.65 | 0 |

Figure 22:
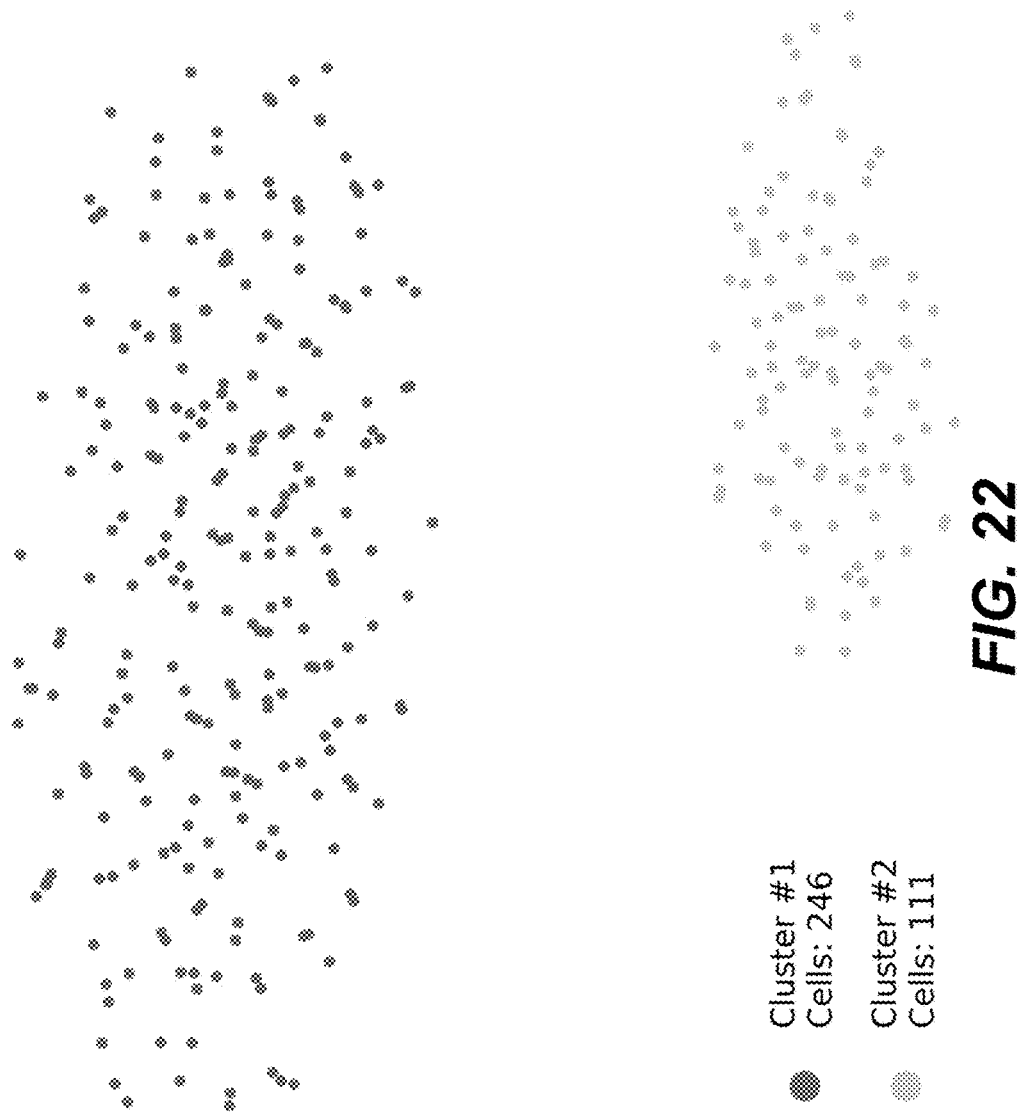
FIG. 22 is a non-limiting exemplary plot illustrating the splitting result of expression profiles in a two dimensional space
Figure 23A:
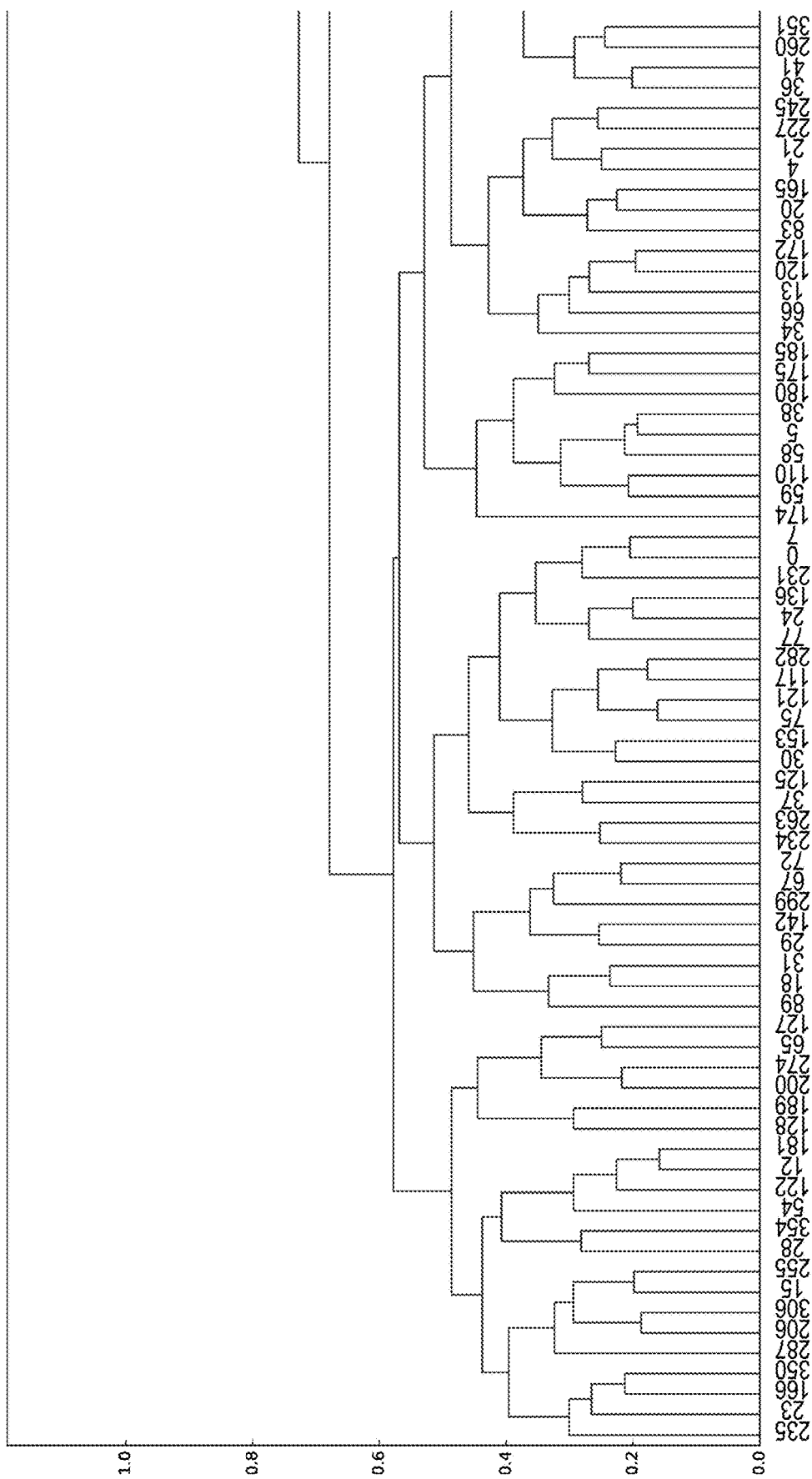
Figure 23B:
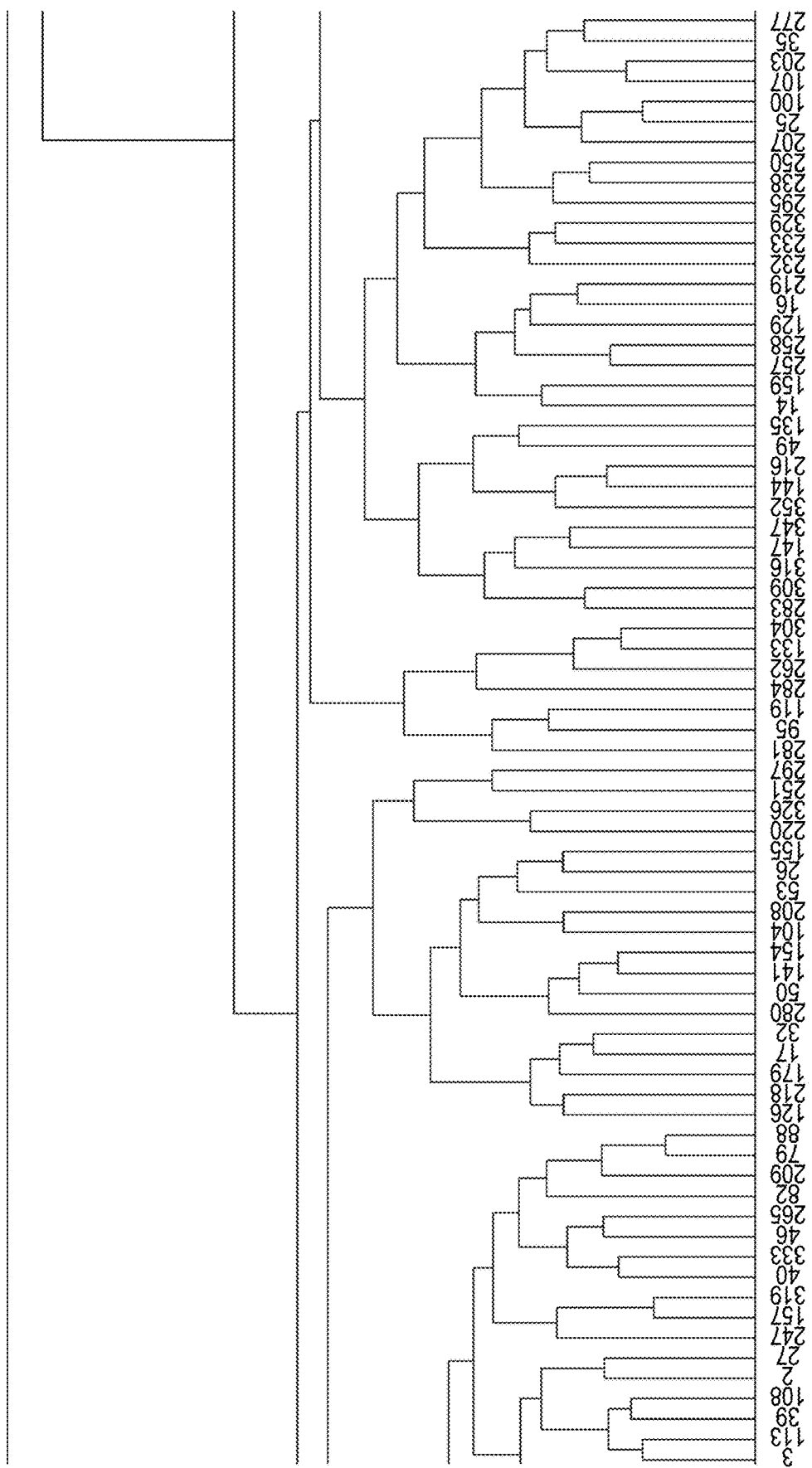
Figure 23C:
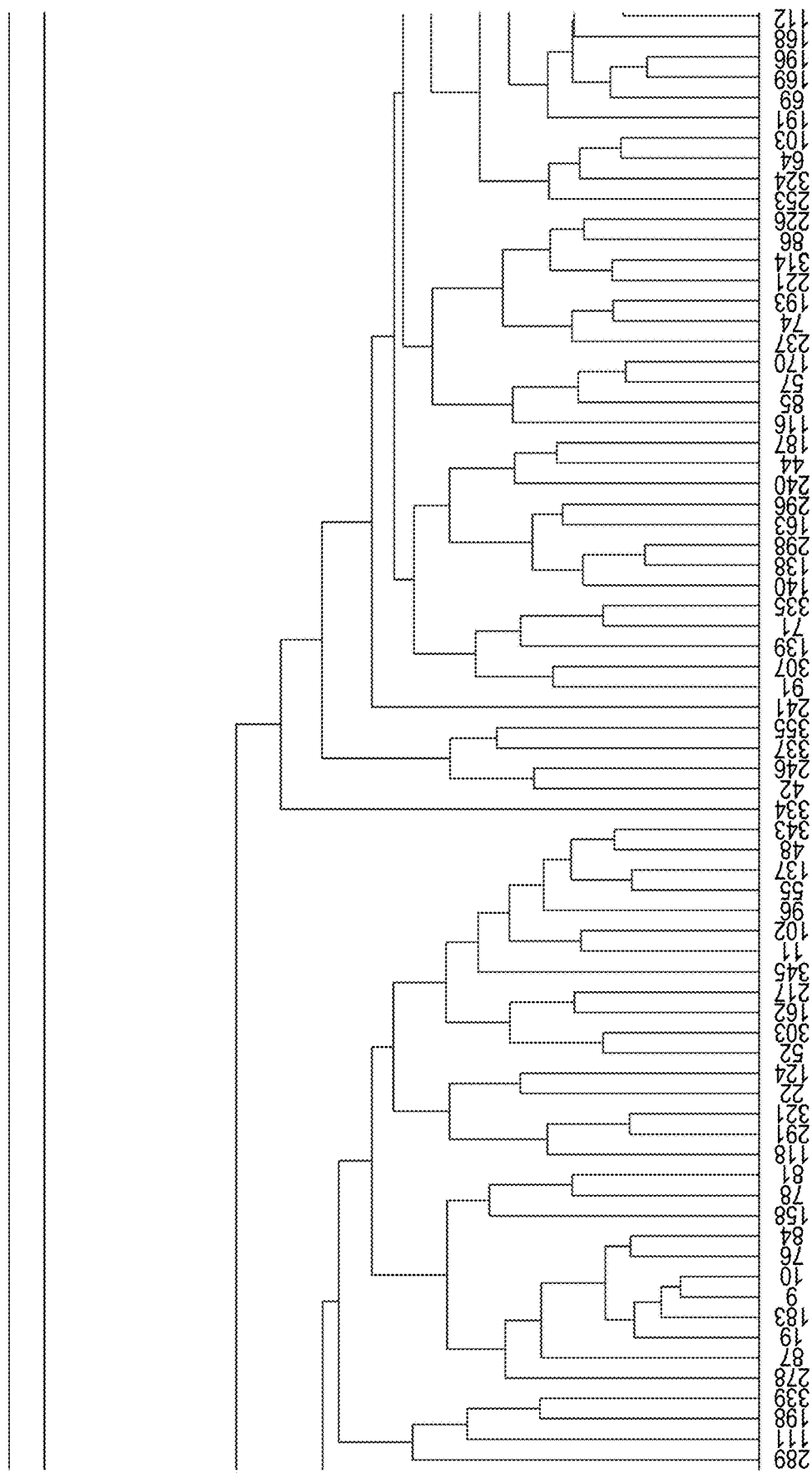
Figure 23D:
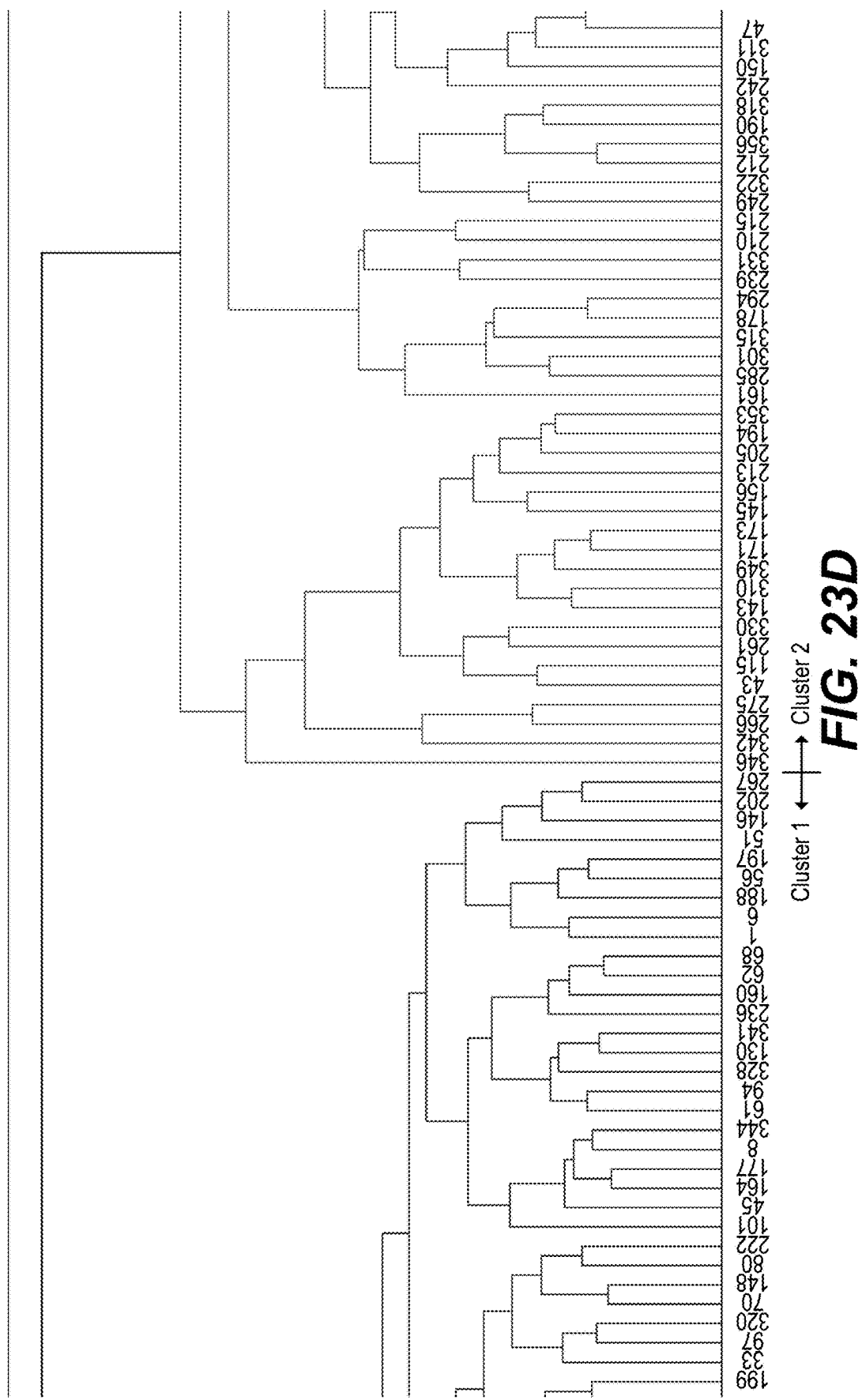
Figure 23E:
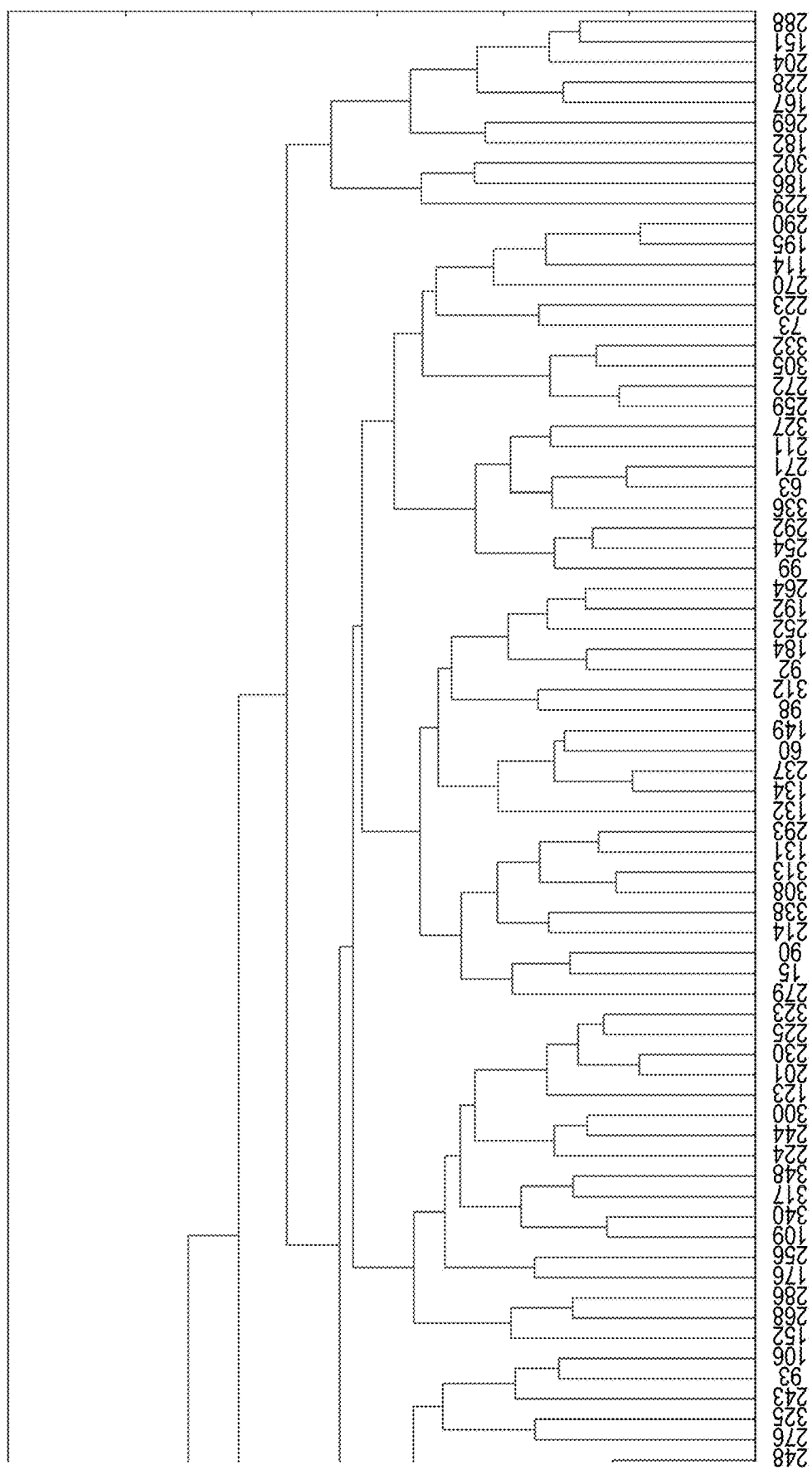
Figure 24:
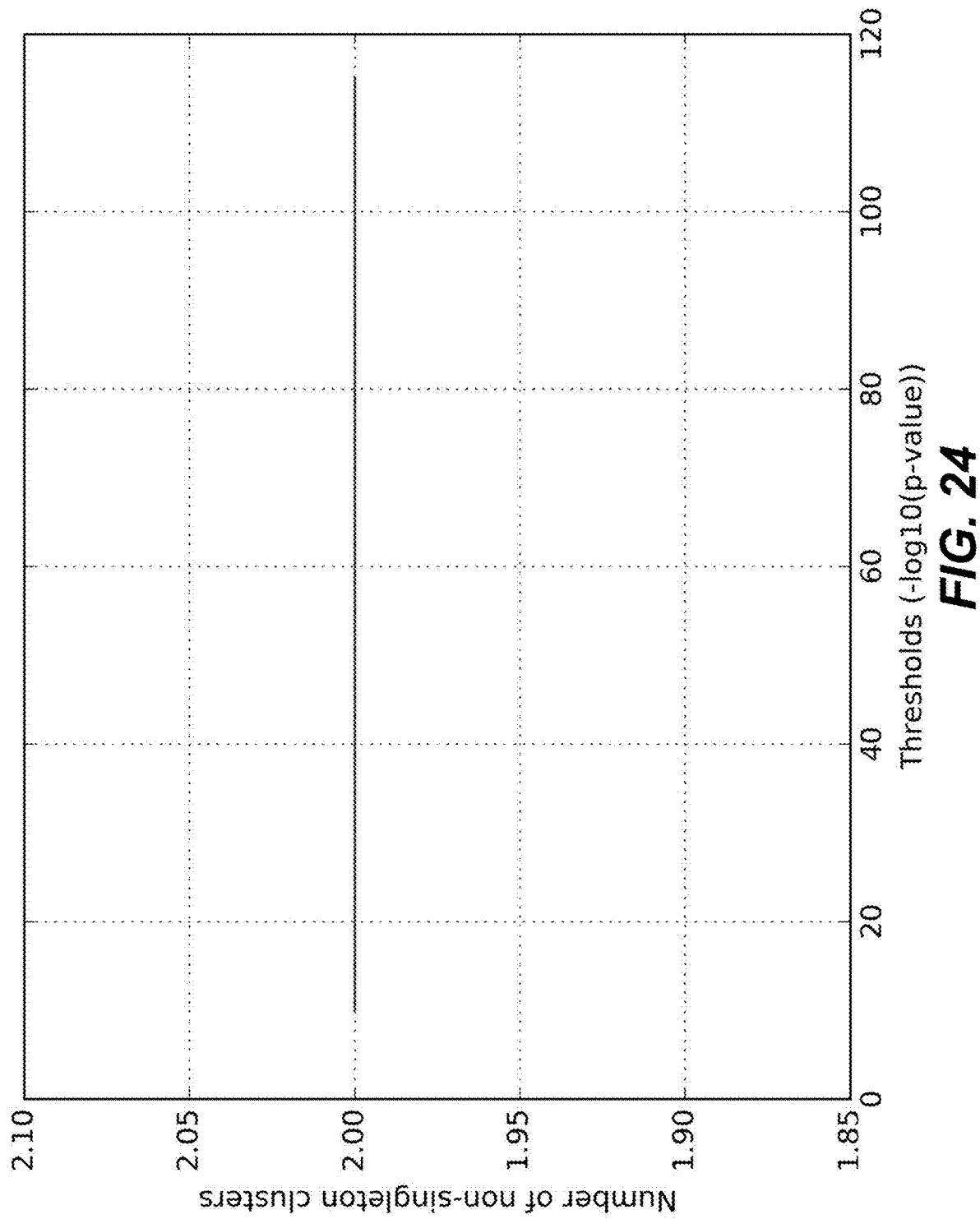
FIG. 24 is another non-limiting exemplary plot showing parameter sweeping.

FIG. 22 is a non-limiting exemplary t-distributed stochastic neighbor embedding (t-SNE) plot illustrating the splitting result of the expression profiles of 357 cells, showing that the 357 cells were classified into two clusters with a threshold of 10. FIGS. 23 and 23A-23E show a non-limiting exemplary dendrogram showing expression profiles classified into two clusters based on the features shown in Table 2 (cluster 0 in Table 1 corresponds to cluster 1 in Table 2, and cluster 1 in Table 2 corresponds to cluster 2 in Table 2). FIG. 24 is a non-limiting exemplary plot showing parameter sweeping. Because two clusters of expression profiles were identified with a threshold of only 10, the same two clusters of expression profiles were identified with larger thresholds (Compare FIG. 24 with FIG. 20).

TABLE 2

Pairwise cluster features of the two clusters ordered by p-Value.

| Comparison | Gene | p-Value | Larger Cluster | Fold Change of Expression for Larger Cluster |
|---|---|---|---|---|
| Cluster1 vs Cluster2 | IGLC3\|ENST00000390325.2\|Reference_end | 201.35 | 1 | 183.947 |
| Cluster1 vs Cluster2 | JCHAIN\|NM_144646.3\|Reference_end | 105.572 | 1 | 50.085 |
| Cluster1 vs Cluster2 | ADA\|NM_000022.3\|Reference_end | 89.274 | 2 | 11.82 |
| Cluster1 vs Cluster2 | TCL1A\|NM_021966.2\|Reference_end | 81.191 | 1 | 134.689 |
| Cluster1 vs Cluster2 | CD74\|NM_004355.3\|Reference_end | 62.653 | 1 | 173.268 |
| Cluster1 vs Cluster2 | CD3D\|NM_000732.4\|Reference_end | 50.32 | 2 | 109.703 |
| Cluster1 vs Cluster2 | POU2AF1\|NM_006235.2\|Reference_end | 39.943 | 1 | 19.778 |
| Cluster1 vs Cluster2 | CD52\|NM_001803.2\|Reference_end | 39.105 | 1 | 50.988 |
| Cluster1 vs Cluster2 | QPCT\|NM_012413.3\|Reference_end | 38.87 | 1 | INF |
| Cluster1 vs Cluster2 | HLA-DRA\|NM_019111.4\|Reference_end | 26.642 | 1 | 71.744 |
| Cluster1 vs Cluster2 | CD22\|NM_001771.3\|Reference_end | 25.96 | 1 | 64.976 |
| Cluster1 vs Cluster2 | IRF8\|NM_002163.2\|Reference_end | 21.245 | 1 | INF |
| Cluster1 vs Cluster2 | MS4A1\|NM_021950.3\|PolyA_1 | 19.993 | 1 | INF |
| Cluster1 vs Cluster2 | CD37\|NM_001774.2\|Reference_end | 18.492 | 1 | INF |
| Cluster1 vs Cluster2 | LEF1\|NM_016269.4\|Reference_end | 17.63 | 2 | 4.807 |
| Cluster1 vs Cluster2 | MME\|NM_000902.3\|Reference_end | 15.585 | 1 | 37.451 |
| Cluster1 vs Cluster2 | BCL6\|NM_001706.4\|Reference_end | 13.393 | 1 | INF |
| Cluster1 vs Cluster2 | CD27\|NM_001242.4\|Reference_end | 11.018 | 1 | INF |
| Cluster1 vs Cluster2 | IL32\|NM_004221.4\|Reference_end | 10.862 | 2 | INF |
| Cluster1 vs Cluster2 | CD38\|NM_001775.3\|Reference_end | 10.649 | 1 | INF |

Altogether, these data demonstrate clustering by recursive splitting and testing followed by merging. In this example, at each cluster or node of the dendrogram (except for the leaf nodes), the intra-cluster median correlation of the two sub-clusters was higher than the inter-cluster median correlation.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for identifying targets to distinguish cell types, comprising:
   (a) receiving a target counts data structure, wherein the target counts data structure comprises expression profiles of a plurality of cells, and wherein the expression profiles of the plurality of cells comprise a number of each target of a plurality of targets for each cell of the plurality of cells, wherein the targets comprise RNA targets;
   (b) hierarchically clustering the expression profiles of the plurality of cells based on the target counts data structure and distances between the expression profiles of the plurality of cells to generate a dendrogram representing the expression profiles of the plurality of cells, wherein the dendrogram comprises a plurality of nodes, wherein the plurality of nodes comprises a root node, a plurality of leaf nodes, and a plurality of non-root, non-leaf nodes, wherein each leaf node of the plurality of leaf nodes represents an expression profile of a different cell of the plurality of cells, and wherein the root node represents the expression profiles of the plurality of cells, wherein each of the plurality of leaf nodes and the plurality of non-root, non-leaf nodes is associated with a parent node, and wherein each of the root node and the plurality of non-root, non-leaf nodes is associated with a left child node and a right child node and represents expression profiles represented by the left child node and the right child node of the node;
   (c) while traversing through each node of the plurality of nodes of the dendrogram from the root node of the dendrogram to the plurality of leaf nodes of the dendrogram:
      (1) determining whether a splitting of the node into child nodes of the node is valid or invalid by:
         determining the splitting to be valid if the distance between the left child node and the right child node is above a splitting threshold; and
         determining the splitting to be invalid if the distance between the left child node and the right child node is not above the splitting threshold,
         wherein the distance between the left child node and the right child node is represented by a p-value derived from independent statistical tests performed on each target of the plurality of targets between expression profiles represented by the left child node and the right child node; and
      (2) for each node for which the splitting of the node into the child nodes of the node is determined to be invalid, adding the node to a merging cluster set;
   (d) iteratively, for each first node in the merging cluster set, determining a distance between the first node in the merging cluster set and a second node in the merging cluster set that is closest to the first node, and for each first node for which the distance between the first node and the second node is determined to be within a merging distance threshold, merging the first node with the second node to generate a merged node comprising expression profiles represented by the first node and the second node; and
   (e) for each node in the merging cluster set, identifying targets for distinguishing cell types based on expression profiles of the plurality of targets of cells represented by the node.

2. The method of claim 1, wherein the target counts data structure comprises a target counts matrix, wherein each row or each column of the target counts matrix comprises a number of each target of a plurality of targets for a different individual cell of the plurality of cells.

3. The method of claim 1, wherein each target of the plurality of targets is a barcoded target comprising a barcode comprising a cell label and a molecular label, wherein barcoded targets from targets of different cells of the plurality of cells have different cell labels, and wherein barcoded targets created from targets of a cell of the plurality of cells have different molecular labels, and wherein the number of each target of the plurality of targets for each cell is based on a number of different molecular labels comprised in the barcode for each target.

4. A method for identifying targets to distinguish cell types, comprising:
   (a) receiving expression profiles of a plurality of cells, wherein the expression profiles comprise a number of each target of a plurality of targets for each cell of the plurality of cells, wherein the targets comprise RNA targets;
   (b) clustering the expression profiles of the plurality of cells to generate a plurality of clusters of expression profiles based on the distances between the expression profiles of the plurality of cells, wherein each cluster has one or more associations with one or both of (1) a parent cluster and (2) two or more child clusters, wherein the parent cluster represents expression profiles of one or more cells of the plurality of cells represented by the cluster, and wherein the cluster represents expression profiles represented by the two or more child clusters,
      wherein each of the plurality of leaf clusters and the plurality of non-root, non-leaf clusters has an association with a parent cluster,
      wherein each of the root cluster and the plurality of non-root, non-leaf clusters has associations with a left child cluster and a right child cluster and represents expression profiles represented by the left child cluster and the right child cluster of the cluster, and
      wherein the root cluster represents the expression profiles of the plurality of cells;
   (c) for each cluster with two or more child clusters, adding the cluster to a merging cluster set upon determining that associations between the cluster with the two or more child clusters are invalid, wherein the associations between the cluster with the two or more child clusters is determined to be invalid when the distance between the left child cluster and the right child cluster is not above an association threshold, wherein the distance between the left child cluster and the right child cluster is represented by a p-value derived from independent statistical tests performed on each target of the plurality of targets between expression profiles represented by the left child cluster and the right child cluster; and (d) iteratively, for each first cluster in the merging cluster set, determining a distance between the first cluster in the merging cluster set and a second cluster in the merging cluster set that is closest to the first cluster, and for each first cluster for which the distance between the first cluster and the second cluster is within a merging distance threshold, merging the first cluster and the second cluster to generate a merged cluster, wherein the merged cluster comprises expression profiles of the first cluster and the second cluster; and (e) for each cluster in the merging cluster set, identifying targets for distinguishing cell types based on expression profiles of the plurality of targets of cells represented by the cluster.

5. The method of claim 4, wherein receiving expression profiles of the plurality of cells comprises receiving a target counts data structure.

6. The method of claim 4, wherein clustering the expression profiles of the plurality of cells into the plurality of clusters of expression profiles based on the distances between the expression profiles of the plurality of cells comprises:
hierarchically clustering the expression profiles of the plurality of cells to generate a dendrogram representing the expression profiles of the plurality of cells based on the distances between the expression profiles of the plurality of cells, wherein the dendrogram comprises the plurality of clusters, wherein the plurality of clusters comprise a root cluster, a plurality of leaf clusters, and a plurality of non-root, non-leaf clusters.

7. The method of claim 4, comprising, prior to clustering the expression profiles of the plurality of cells to generate the plurality of clusters of expression profiles based on the distances between the expression profiles of the plurality of cells in (b):
(i) determining a distance data structure of the expression profiles of the plurality of cells.

8. The method of claim 4, wherein clustering the expression profiles of the plurality of cells based on distances between the expression profiles of the plurality of cells in (b) comprises:
assigning each expression profile of the plurality of cells to a different leaf cluster in the plurality of clusters; and
iteratively combining a first cluster and a second cluster of the plurality of clusters to generate a parent cluster of the first cluster and the second cluster if the second cluster is the closest cluster of the plurality of cluster to the first cluster.

9. The method of claim 4, wherein the statistical test comprises a Welch's t-test.

10. The method of claim 4, wherein the distance between the left child cluster and the right child cluster is determined based on the maximum p-value of the statistical test performed on the each target of the plurality of targets between each expression profile represented by the left child cluster and each expression profile represented by the right child cluster.

11. The method of claim 4, wherein for each cluster in the merging cluster set, identifying the targets for distinguishing the cell types based on the expression profiles of the plurality of targets of the cells represented by the cluster comprises:
determining a difference, between expression profiles represented by the cluster and expression profiles represented by another cluster in the merging cluster set, in numbers of molecular labels with distinct sequences associated with the targets for distinguishing the cell types is greater than a significance threshold.

12. The method of claim 4, comprising, prior to merging the first cluster with the second cluster to generate the merged cluster in (d):
merging each third cluster in the merging cluster set representing an expression profile of a single cell with a fourth cluster in the merging cluster set if a distance between the third cluster and the fourth cluster is within a cluster distance threshold.

13. The method of claim 4, comprising classifying the plurality of cells based on the clusters in the merging cluster set that represent expression profiles of the cells.

14. The method of claim 4, wherein each target of the plurality of targets is a barcoded target comprising a barcode comprising a cell label and a molecular label, wherein barcoded targets from targets of different cells of the plurality of cells have different cell labels, and wherein barcoded targets created from targets of a cell of the plurality of cells have different molecular labels, and wherein the number of each target of the plurality of targets for each cell is based on a number of different molecular labels comprised in the barcode for each target.

15. The method of claim 6, wherein for each cluster with two or more child clusters, if associations between the cluster with the two or more child clusters are invalid, adding the cluster to a merging cluster set comprises:
while traversing through each cluster of the dendrogram from the root cluster of the dendrogram to the plurality of leaf clusters of the dendrogram:
(1) determining whether associations of the cluster with child clusters of the cluster are valid or invalid; and
(2) if the associations are invalid, adding the cluster to a merging cluster set.

16. The method of claim 15, comprising, at each cluster when traversing the plurality of clusters of the dendrogram:
if the associations are valid, continuing traversing from the cluster to the left child cluster and the right child cluster of the cluster; and
if the associations are invalid, discontinuing traversing from the cluster to the left child cluster and the right child cluster of the cluster.

17. The method of claim 15, comprising, at each cluster when traversing the plurality of clusters of the dendrogram:
(3) adding the cluster to the merging cluster set if the cluster represents an expression profile of a single cell.

18. The method of claim 15, comprising, at each cluster when traversing the plurality of clusters of the dendrogram: assigning a cluster label to the cluster.

19. The method of claim 18,
wherein, if the cluster represents an expression profile of a single cell, the cluster label of the cluster comprises a single cell designation,
otherwise, if the cluster is the left child cluster of the parent cluster, the cluster label of the cluster comprises the cluster label of the parent cluster and a left designation, and otherwise, the cluster label of the cluster comprises the cluster label of the parent cluster and a right designation.

20. The method of claim 7, wherein the distance data structure comprises a distance matrix of the expression profiles of the plurality of cells.

21. The method of claim 7, wherein the distances between the expression profiles of the plurality of cells are pairwise correlation distances between the expression profiles of the plurality of cells.

22. The method of claim 7, comprising, prior to determining the distance data structure in (i), log-transforming the target counts data structure into a log-transformed target counts data structure,
   wherein determining the distance data structure of elements of the target counts data structure comprises determining the distance data structure of the log-transformed target counts data structure, and
   wherein clustering the expression profiles of the plurality of cells to generate the plurality of clusters of expression profiles based on the distances between the expression profiles of the plurality of cells in (b) comprises: clustering the expression profiles of the plurality of cells based on the log-transformed target counts data structure and the distance data structure to generate the plurality of clusters.

23. The method of claim 20, wherein each diagonal element of the distance matrix has a value of zero.

24. The method of claim 20, wherein clustering the expression profiles of the plurality of cells to generate the plurality of clusters of expression profiles based on the distances between the expression profiles of the plurality of cells in (b) comprises:
   clustering the expression profiles of the plurality of cells to generate the plurality of clusters of expression profiles based on the distance matrix.

25. The method of claim 22, wherein log-transforming the target counts data structure into the log-transformed target counts data structure comprises increasing the value of each element of the target counts data structure by an increment.

26. The method of claim 8, wherein the distance between the first cluster and the second cluster is the maximum distance between any expression profile represented by the first cluster and any expression profile represented by the second cluster.

27. The method of claim 8, wherein an intra-cluster correlation of the first cluster and an intra-cluster correlation of the second cluster are higher than an inter-cluster correlation of the first cluster and the second cluster.

28. The method of claim 8, wherein an indication of an intra-cluster correlation of the first cluster and an intra-cluster correlation of the second cluster is higher than an inter-cluster correlation of the first cluster and the second cluster.

29. The method of claim 27,
   wherein the intra-cluster correlation of the first cluster is based on at least one of:
      an intra-cluster maximum correlation of the first cluster,
      an intra-cluster average correlation of the first cluster,
      an intra-cluster median correlation of the first cluster,
      an intra-cluster minimum correlation of the first cluster, and
      any combinations thereof,
   wherein the intra-cluster correlation of the second cluster is based on at least one of:
      an intra-cluster maximum correlation of the second cluster,
      an intra-cluster average correlation of the second cluster,
      an intra-cluster median correlation of the second cluster,
      an intra-cluster minimum correlation of the second cluster, and
      any combinations thereof, and
   wherein the inter-cluster correlation of the first cluster and the second cluster is based on at least one of:
      an inter-cluster maximum correlation of the first cluster and the second cluster,
      an inter-cluster average correlation of the first cluster and the second cluster,
      an inter-cluster median correlation of the first cluster and the second cluster,
      an inter-cluster minimum correlation of the first cluster and the second cluster, and
      any combinations thereof.

30. The method of claim 28,
   wherein the indication of the intra-cluster correlation of the first cluster and the intra-cluster correlation of the second cluster is based on at least one of:
      an intra-cluster maximum correlation of the first cluster and the second cluster,
      an intra-cluster average correlation of the first cluster and the second cluster,
      an intra-cluster median correlation of the first cluster and the second cluster,
      an intra-cluster minimum correlation of the first cluster and the second cluster, and
      any combinations thereof.

* * * * *